(12) United States Patent
Kim et al.

US006838556B2

(10) Patent No.: US 6,838,556 B2
(45) Date of Patent: Jan. 4, 2005

(54) PROMOTERS FOR REGULATED GENE EXPRESSION

(75) Inventors: Jungsuh P. Kim, Palo Alto, CA (US); Douglas B. Starr, Mountain View, CA (US); Albert W. Tam, San Francisco, CA (US); Megan E. Laurance, San Francisco, CA (US); Emil F. Michelotti, Foster City, CA (US); Mark D. Velligan, Montara, CA (US); Derek R. Latour, Hayward, CA (US); Rita L. Thomas, San Jose, CA (US); Ana Kongpachith, Union City, CA (US); Liana T. Sheppard, Redwood City, CA (US); Moon Young Kim, Redwood City, CA (US); Thomas W. Bruice, Carlsbad, CA (US)

(73) Assignee: Genelabs Technologies, Inc., Redwood City, CA (US)

( * ) Notice: Subject to any disclaimer, the term of this patent is extended or adjusted under 35 U.S.C. 154(b) by 34 days.

(21) Appl. No.: 09/875,453

(22) Filed: Jun. 6, 2001

(65) Prior Publication Data

US 2003/0027320 A1 Feb. 6, 2003

Related U.S. Application Data

(60) Provisional application No. 60/209,549, filed on Jun. 6, 2000.

(51) Int. Cl.$^7$ .............................................. C12N 15/11
(52) U.S. Cl. ...................................... 536/24.1
(58) Field of Search ............................... 536/24.1, 23.1

(56) References Cited

U.S. PATENT DOCUMENTS 6,156,876 A * 12/2000 Beach ......................... 530/350

FOREIGN PATENT DOCUMENTS

| WO | WO 00/52179 | 9/2000 |
| WO | WO 01/94600 | 12/2001 |

OTHER PUBLICATIONS

Hinz, M. et al., "NF–kB Function in Growth Control: Regulation of Cyclin D1 Expression and $G_0/G_1$–to–S–Phase Transition," *Mol. Cell. Biol.* 19:(4) 2690–2698 (1999).

Kitazawa, S. et al., "Transcriptional Regulation of Rat Cyclin D1 Gene by GpG Methylation Status in Promotor Region," *J. Biol. Chem.* 274: (40) 28787–28793 (1999).

Laurance, M.E. et al., "Specific down–regulation of an engineered human cyclin D1 promoter by a novel DNA–b-inding ligand in intact cells," *Nucleic Acids Res.* : 29:(3) 652–661 (2001).

Lee, R.J., et al., "pp60$^{v-src}$ Induction of Cyclin D1 Requires Collaborative Interactions between the Extracellular Signal–regulated Kinase, p38, and Jun Kinase Pathways," *J. Biol. Chem.* 274:(11) 7341–7350 (1999).

Shtutman, M., et al., "The cyclin D1 gene is a target of the β–catenin/LEF–1 pathway," *Proc. Natl. Acad. Sci. USA* 96:5522–5527 (1999).

Tetsu, O., et al., "β–Cetenin regulates expression of cyclin D1 in colon carcinoma cells," *Nature*, 398:422–426 (1999).

* cited by examiner

*Primary Examiner*—Terry McKelvey
(74) *Attorney, Agent, or Firm*—Perkins Coie LLP

(57) ABSTRACT

This invention provides nucleic acid sequences, vectors and host cells comprising regulatory regions associated with various promoters including a cyclin D1 promoter, a CD40L promoter, three HBV promoters (core, pre-S1 and HBV-X), a vancomycin-resistant enterococci (VRE) promoter, an androgen receptor promoter, a Her2 promoter, and β-lactamase promoter. The invention further provides methods of regulating gene expression comprising the regulatory regions of such promoters.

1 Claim, 14 Drawing Sheets

GCACGTCGCATGGAGACCACCGTGAACGCCCACCAAATAT

** *** **************** *
TGCCCAAGGTCTTACATAAGAGGACTCTTGGACTCTCAGC
                            HNF4

***************** ****

AATGTCAACGACCGACCCTTGAGGCATACTTCAAAGACTGT
  HNF3-1                          HNF

* ****  **************** ********
TTGTTTTAAAGACTGGGAGGAGTTGGGGGAGGAGATTAGGT
  3-2

*** * * *******
TAAAGGTCTCTTTGTACTAGGAGGCTGTAGGCATAAATTGGT

***
CTGCGCACCAGCACCATGCAACTTTTTTCACCTCTGCCTAA
                         Pre-genomic

***** *
TCATCTCTTG

* nucleotide conserved at >95% among 75 HBV strains

Fig. 1A

2701 TTATTATCCAGAACATCTA<u>GTTAATCATTACT</u>TCCAAACTAGA<u>CACTATTTACAC</u>ACTCT
                           HNF1                                HNF3

2761 ATGG<u>AAGGCGGGT</u>ATAT<u>TATATAA</u>GAGAGAAACAACACATAGCGCCTCATTTTGTGGGTC
       Sp1          TBP                                    RNA Start 2821 ACCATATTCTTGGGAACAAGATCTACAGC<u>ATGGGGC</u>
                                  PreS1 protein start

Fig. 1B

1081 CTA AGC AGG CTT TCA CTT TCT CGC CAA CTT ACA AGG CCT TTC TGT GTA AAC AAT
                            NF1(1100-1119)
                                                    2c (1119-1134)

1135 ACC TGA ACC TTT ACC CCG TTG CCC GGC AAC GGC CAG GTC TGT GCC AAG TGT TTG
                    EF-C(1148-1168)

1189 CTG ACG CAA CCC CCA CTG GCT GGG GCT TGG TCA TGG GCC ATC AGC GCA TGC GTG
        E(1180-1202)                   NF1(1209-1236)           X-PBP(1229-1245)

1243 GAA CCT TTT CGG CTC CTC TGC CGA TCC ATA CTG CGG AAC TCC TAG CCG CTT GTT

1297 TTG CTC GCA GCA GGT CTG GAG CAA ACA TTA TCG GGA CTG ATA ACT CTG TTG TCC

1351 TAT CCC GCA AAT ATA CAT CGT TTC CAT GGC TGC TAG 1386

Fig. 3

```
                CAGCTGGG  CCGCCCTTGT  GCGCGGGCTG  ATGCTCTGAG  GCTTGGCTAT
GCGGGGGCCA  ACGCGATTGT  GGGTGCTCGG  GGAGTGGGGG  GGGGCACGAC  CGTAGGTGCT
CCCTGCTGGG  GCAACCCATC  GCTCCCCATG  CGGAATCCGG  GGGTAATTAC  CCCCCCAGGA
CCCGGAATAT  TAGTAATCCT  AATTCCCGGC  GGGGGAGGGG  GCGCGGGAGG  AATTCACCCT
GAAAGGTGGG  GGTGGGGGGG  GTCGCATCTT  GCTGTGAGCA  CCCTGGCGAA  GGGGAGAGGG
CTTTTTCTAT  CAGTTTTCTT  TGAGCTTTTA  CTGTTAAGAG  GGTACGGTGG  TTTGATGACA
CTGAACTATA  TTCAAAAGGA  AGTAAATGAA  CAGTTTTCTT  AATTTGGGGC  AGGTACTGTA
AAAATAAAAA  CAAAAGTTAA  GACAGTAAAA  TGTCCTTTTA  TTTTTTAATG  CACCAAAGAG
ACAGAACCTG  TAATTTTAAA  AACTGTGTAT  TTTAATTTAC  ATCTGCTTAA  GTTTGCGATA
ATATTGGGGA  CCCTCTCATG  TAACCACGAA  CACCTATCGA  TTTTGCTAAA  AATCAGATCA
GTACACTCGT  TTGTTTAATT  GATAATTGTT  CTGAATTATG  CCGGCTCCTG  CCAGCCCCCT
CACGCTCACG  AATTCAGTCC  CAGGGCAAAT  TCTAAAGGTG  AAGGGACGTC  TACACCCCCA
ACAAAACCAA  TTAGGAACTT  CGGTGGTCTT  GTCCCAGGCA  GAGGGGACTA  ATATTTCCAG
CAATTTAATT  TCTTTTTTAA  TTAAAAAAAA  TGAGTCAGAA  TGGAGATCAC  TGTTTCTCAG
CTTTCCATTC  AGAGGTGTGT  TTCTCCCGGT  TAAATTGCCG  GCACGGGAAG  GGAGGGGGTG
CAGTTGGGGA  CCCCCGCAAG  GACCGACTGG  TCAAGGTAGG  AAGGCAGCCC  GAAGAGTCTC
CAGGCTAGAA  GGACAAGATG  AAGGAAATGC  TGGCCACCAT  CTTGGGCTGC  TGCTGGAATT
TTCGGGCATT  TATTTTATTT  TATTTTTTGA  GCGAGCGCAT  GCTAAGCTGA  AATCCCTTTA
ACTTTTAGGG  TTACCCCCTT  GGGCATTTGC  AACGACGCCC  CTGTGCGCCG  GAATGAAACT
TGCACAGGGG  TTGTGTGCCC  GGTCCTCCCC  GTCCTTGCAT  GCTAAATTAG  TTCTTGCAAT
TTACGTGT    TAATGAAAAT  GAAAGAAGAT  GCAGTCGCTG  AGATTCTTTG  GCCGTCTGTC
CGCCCGTGGG  TGCCCTCGTG  GCGTTCTTGG  AAATGCGCCC  ATTCTGCCGG  CTTGGATATG
GGGTGTCGCC  GCGCCCCAGT  CACCCCTTCT  CGTGGTCTCC  CCAGGCTGCG  TGCTGTGCCG
GCCTTCCTAG  TTGTCCCCTA  CTGCAGAGCC  ACCTCCACCT  CACCCCCTAA  ATCCCGGGGG
ACCCACTCGA  GGCGGACGGG  GCCCCCTGCA  CCCCTCTTCC  CTGGCGGGGA  GAAAGGCTGC
AGCGGGGCGA  TTTGCATTTC  TATGAAAACC  GGACTACAGG  GGCAACTCCG  CCGCAGGGCA
GGCGCGGCGC  CTCAGGGATG  GCTTTTGGGC  TCTGCCCCTC  GCTGCTCCCG  GCGTTTGGCG
CCCGCGCCCC  CTCCCCCTGC  GCCCGCCCCC  GCCCCCCTCC  CGCTCCCATT  CTCTGCCGGG
CTTTGATCTT  TGCTTAACAA  CAGTAACGTC  ACACGGACTA  CAGGGGAGTT  TTGTTGAAGT
TGCAAAGTCC  TGGAGCCTCC  AGAGGGCTGT  CGGCGCAGTA  GCAGCGAGCA  GCAGAGTCCG
CACGCTCCGG  CGAGGGGCAG  AAGAGCGCGA  GGGAGCGCGG  GGCAGCAGAA  GCGAGAGCCG
AGCGCGGACC  CAGCCAGGAC  CCACAGCCCT  CCCCAGCTGC  CCAGGAAGAG  CCCCA
```

Fig. 4

```
           10         20         30         40         50         60         70
    GAATTCACTG GGGAGAGCAT TCAGGAAGAT GACAACAGGA TAATAGGTCA ACAGAGTAAT AGAGAGGTCG
    CTTAAGTGAC CCCTCTCGTA AGTCCTTCTA CTGTTGTCCT ATTATCCAGT TGTCTCATTA TCTCTCCAGC 80         90        100        110        120        130        140
    CTAAAAATAA ACTCTAAGAA GTATTCAGCC AAAACTATTA TTGAGCTAAT AATGGTGGGA TCAATTTCAG
    GATTTTTATT TGAGATTCTT CATAAGTCGG TTTTGATAAT AACTCGATTA TTACCACCCT AGTTAAAGTC 150        160        170        180        190        200        210
    GGGAATATTG TGGGCAGAAG TCAGACTGTA GGAGGCTGGG GATCAAGAAG TTGAGGCAAG GAGGTTGGAC
    CCCTTATAAC ACCCGTCTTC AGTCTGACAT CCTCCGACCC CTAGTTCTTC AACTCCGTTC CTCCAACCTG 220        230        240        250        260        270        280
    AACAACTGTT TTTTCAAGTT GGTCACGTGA ACAAATCTGT GACCTTCAGC CTCCCCTCCC TCGGGTCTTG
    TTGTTGACAA AAAAGTTCAA CCAGTGCACT TGTTTAGACA CTGGAAGTCG GAGGGGAGGG AGCCCAGAAC 290        300        310        320        330        340        350
    GCTGAGCTGA TTGCAGGGCC CCTGCAGCTC TGGCACTCTC AAGTTGTATA AAACTGACAG TGCAGAAGTC
    CGACTCGACT AACGTCCCGG GGACGTCGAG ACCGTGAGAG TTCAACATAT TTTGACTGTC ACGTCTTCAG 360        370        380        390        400        410        420
    CTTGAGCCCA TTTTGGCTCT CATGATAATT TTCCTTCAGT GGAACTAAGG TTACTTGTCT AAGAACCAAA
    GAACTCGGGT AAAACCGAGA GTACTATTAA AAGGAAGTCA CCTTGATTCC AATGAACAGA TTCTTGGTTT 430        440        450        460        470        480        490
    GCCTCTGACT TGACTGATCA AAGTTCATCA CGTGCATCGA AGCCACCTAC TTGGCAGATG TAGTGAAAAG
    CGGAGACTGA ACTGACTAGT TTCAAGTAGT GCACGTAGCT TCGGTGGATG AACCGTCTAC ATCACTTTTC 500        510        520        530        540        550        560
    CTACATAGAT CTGGGCCCAG GACAGGATGC TGGGGCGTGG GAGGGGAAGA AAGCAGGTGC TAACTATATA
    GATGTATCTA GACCCGGGTC CTGTCCTACG ACCCCGCACC CTCCCCTTCT TTCGTCCACG ATTGATATAT 570        580        590        600        610        620        630
    GATAGCATGC CTATCAGAGC AGTTTTTACG TTTCCTATTT GTCTCTCAAA ACAATTTTAT AGGAATCATC
    CTATCGTACG GATAGTCTCG TCAAAAATGC AAAGGATAAA CAGAGAGTTT TGTTAAAATA TCCTTAGTAG 640        650        660        670        680        690        700
    AAAGCAATTT TATCATGGTT TCTAGACCAG GTTTGGATGT GAGGTAGGGA TTTCCACAGC TGCTTTTAGT
    TTTCGTTAAA ATAGTACCAA AGATCTGGTC CAAACCTACA CTCCATCCCT AAAGGTGTCG ACGAAAATCA 710        720        730        740        750        760        770
    TTGAAGGAAA TCTGATAAGA TGATGCAAAA GCCCTTCAGA AATGTGTAAT CCTACACACT TCAGTGATTC
    AACTTCCTTT AGACTATTCT ACTACGTTTT CGGGAAGTCT TTACACATTA GGATGTGTGA AGTCACTAAG 780        790        800        810        820        830        840
    AATTCATTGT CAAAACTTAA GGTGTTTTTA ATATTGTTAT TGTTCATTTG GTTTTTACCA ACATGTAAGG
    TTAAGTAACA GTTTTGAATT CCACAAAAAT TATAACAATA ACAAGTAAAC CAAAAATGGT TGTACATTCC 850        860        870        880        890        900        910
    AGTTGGCAAT TATTTGTTAA ACTCATGTCT TAGGCTAAAT AAATTCCAAA AAATTCAGGA TGAGAATTGT
    TCAACCGTTA ATAAACAATT TGAGTACAGA ATCCGATTTA TTTAAGGTTT TTTAAGTCCT ACTCTTAACA
```

Fig. 5A

```
      920        930        940        950        960        970        980
TTATTGCTTA ACGTGTGTCA AATTTCTTCC ATGCACATCT TTATTAGATC TTCACAGCAA CCTACAGGAT
AATAACGAAT TGCACACAGT TTAAAGAAGG TACGTGTAGA AATAATCTAG AAGTGTCGTT GGATGTCCTA 990       1000       1010       1020       1030       1040       1050
AAGCAAGACA GGTGCAAGTG CCTCCTTTGG GTATGAGGAA ACTGAGGTCT AAAGAGATGA AGTGATTTGC
TTCGTTCTGT CCACGTTCAC GGAGGAAACC CATACTCCTT TGACTCCAGA TTTCTCTACT TCACTAAACG 1060       1070       1080       1090       1100       1110       1120
CCAAGGCTCA TAGCAATTTA TTGGTAGAGC AAAGACTAGA ATTCTCTTAA CTGCAGCCTA TTTTCCCTAT
GGTTCCGAGT ATCGTTAAAT AACCATCTCG TTTCTGATCT TAAGAGAATT GACGTCGGAT AAAAGGGATA 1130       1140       1150       1160       1170       1180       1190
TCTGAACTGT TACATCAGCA TCAACAATTA TCTAATGGAT TGGAACAGTG TACACAGGCA GCTTAGCTAC
AGACTTGACA ATGTAGTCGT AGTTGTTAAT AGATTACCTA ACCTTGTCAC ATGTGTCCGT CGAATCGATG 1200       1210       1220       1230       1240       1250       1260
GTCAAGTCAC GATTTTTACT TTAACTTCAA TTCCAGAGTC TTGGCCTGAT TTCCCTCAAG ACCCTACTTA
CAGTTCAGTG CTAAAAATGA AATTGAAGTT AAGGTCTCAG AACCGGACTA AAGGGAGTTC TGGGATGAAT 1270       1280       1290       1300       1310       1320       1330
TCTTTGGCTT TGGAAAATTT ATTTTTCTTG CATTATCTTT CCAGCTAAAT TTTATTTAAT AACCATCAGC
AGAAACCGAA ACCTTTTAAA TAAAAAGAAC GTAATAGAAA GGTCGATTTA AAATAAATTA TTGGTAGTCG 1340       1350       1360       1370       1380       1390       1400
ATGCTTTTTT TGCTTTATGC CATGTAGACT TGACCTGAAA ACCTGCCAGG CTTTCATTGA GTTTAGTGAT
TACGAAAAAA ACGAAATACG GTACATCTGA ACTGGACTTT TGGACGGTCC GAAAGTAACT CAAATCACTA 1410       1420       1430       1440       1450       1460       1470
TAAAGAAGTA AAGTTCTGAG AAGCAATTAG TTGATGGGAC ACCAGTCATA AAATCAATCC AAACTTTTGT
ATTTCTTCAT TTCAAGACTC TTCGTTAATC AACTACCCTG TGGTCAGTAT TTTAGTTAGG TTTGAAAACA 1480       1490       1500       1510       1520       1530       1540
TGACATGTGT TTCTTTCTCC ATATACCAGG TTCCCGCTTC GTATTAGTAA GATTGAAATT GAAATAAGTC
ACTGTACACA AAGAAAGAGG TATATGGTCC AAGGGCGAAG CATAATCATT CTAACTTTAA CTTTATTCAG 1550       1560       1570       1580       1590       1600       1610
TATTGCTGGT GGATGAATTT GTCACTTTCC TTGAAACTGG TGAACCCAAA AAGTTAGACA GTGATAGGAA
ATAACGACCA CCTACTTAAA CAGTGAAAGG AACTTTGACC ACTTGGGTTT TTCAATCTGT CACTATCCTT 1620       1630       1640       1650       1660       1670       1680
AATACTGCCA TTGTCTGTTA AGAAGTCTAT GACATTTCAA GGCAAGAATG AATATATGGA AGAAGAAACT
TTATGACGGT AACAGACAAT TCTTCAGATA CTGTAAAGTT CCGTTCTTAC TTATATACCT TCTTCTTTGA 1690       1700       1710       1720       1730       1740       1750
TGTTTCTTCT TTACTTACAA AAAGGAAAGC CTGGAAGTGA ATGATATGGG TATAATTAAA AAAAAAAAAA
ACAAAGAAGA AATGAATGTT TTTCCTTTCG GACCTTCACT TACTATACCC ATATTAATTT TTTTTTTTT 1760       1770       1780       1790       1800       1810       1820
AAAACAAAAA ACCTTTACGT AACGTTTGC TGGGAGAGAA GACTACGAAG CACATTTTCC AGGAAGTGTG
TTTTGTTTTT TGGAAATGCA TTGCAAAACG ACCCTCTCTT CTGATGCTTC GTGTAAAAGG TCCTTCACAC
```

Fig. 5B

```
          1830       1840       1850       1860       1870       1880       1890
     GGCTGCAACG ATTGTGCGCT CTTAACTAAT CCTGAGTAAG GTGGCCACTT TGACAGTCTT CTCATGCTGC
     CCGACGTTGC TAACACGCGA GAATTGATTA GGACTCATTC CACCGGTGAA ACTGTCAGAA GAGTACGACG 1900       1910       1920       1930       1940       1950       1960
     CTCTGCCACC TTCTCTGCCA GAAGATACCA TTTCAACTTT AACACAGCAT GATCGAAACA TACAACCAAA
     GAGACGGTGG AAGAGACGGT CTTCTATGGT AAAGTTGAAA TTGTGTCGTA CTAGCTTTGT ATGTTGGTTT 1970       1980       1990       2000       2010       2020       2030
     CTTCTCCCCG ATCTGCGGCC ACTGGACTGC CCATCAGCAT GAAAATTTTT ATGTATTTAC TTACTGTTTT
     GAAGAGGGGC TAGACGCCGG TGACCTGACG GGTAGTCGTA CTTTTAAAAA TACATAAATG AATGACAAAA 2040       2050       2060       2070       2080       2090       2100
     TCTTATCACC CAGATGATTG GGTCAGCACT TTTTGCTGTG TATCTTCATA GAAGGCTGGA CAAGGTAAGA
     AGAATAGTGG GTCTACTAAC CCAGTCGTGA AAAACGACAC ATAGAAGTAT CTTCCGACCT GTTCCATTCT 2110       2120       2130       2140       2150       2160       2170
     TGAACCACAA GCCTTTATTA ACTAAATTTG GGGTCCTTAC TAATTCATAG GTTGGTTCTA CCCAAATGAT
     ACTTGGTGTT CGGAAATAAT TGATTTAAAC CCCAGGAATG ATTAAGTATC CAACCAAGAT GGGTTTACTA 2180       2190       2200       2210       2220       2230       2240
     GGATGATGGT AGAAACCAAA TAGAAGAATG GTCTTGTGGC ATAATGTTTG TTCCCTAGTC AATGAACTCT
     CCTACTACCA TCTTTGGTTT ATCTTCTTAC CAGAACACCG TATTACAAAC AAGGGATCAG TTACTTGAGA 2250       2260       2270       2280       2290       2300       2310
     CATATTCTTG TCTCTGGTTA GGATCTTGGG ATCTGGAGTC AGACTGCCTG GGCTCAAATC TTGGCTCTGC
     GTATAAGAAC AGAGACCAAT CCTAGAACCC TAGACCTCAG TCTGACGGAC CCGAGTTTAG AACCGAGACG 2320       2330       2340       2350       2360       2370       2380
     CCATACCATC TCTGTTATCC TGGGGCAAGT GCCTCAGTTT CCACATCTGA GAAATGGGGA TGGTAGTGGT
     GGTATGGTAG AGACAATAGG ACCCCGTTCA CGGAGTCAAA GGTGTAGACT CTTTACCCCT ACCATCACCA

2390
     GTCCATTTCA TAGAT
     CAGGTAAAGT ATCTA
```

Fig. 5C

```
GAGATGTATATAATTTTTTAGGAAAATCTCAAGGTTATCTTTACTTTTTCTTA
GGAAATTAACAATTTAATATTAAGAAACGGCTCGTTCTTACACGGTAGACTTA
ATACCGTAAGAACGAGCCGTTTTCGTTCTTCAGAGAAAGATTTGACAAGATTA
CCATTGGCATCCCCGTTTTATTTGGTGCCTTTCACAGAAAGGGTTGGTCTTAA
TT
```

Fig. 6

```
TCTAGAAAAT AATTCCCAAT ATTGAATCCC AAAGAATTCA ACATTTGGGC TGTCGTTTGA  61
AAGATAAGTT GAATTTGGTC ATGAAGGAAG AGAGGGGGGA TACAATTTCA GTAAAAGGTA 121
ACAGCAAGGT CCAAAGACAG TCAGGTCTTC AGTAGTATGG AGTATATTCA GAGGGAGCCA 181
AGATGTCTGA TGTGAACTAA AAAGATTGGT GGTTGGTAGG AGGAAGAGGT GTGAGAAGAG 241
GCTGTAAAGA AAAATTGAAA CTTGATTGTG ATGGACTTTA AAGGCTAGGC TATGGGACTT 301
GGACATGAAT CTGCAGGCCA GTGTTTGCAG ACTGGCGCCC ATAACTGTCT ATCACAGCAA 361
CACAGACATG TGTTGTTTGG CCTGCAGAGG TTTGGCCTGC ATGATGATTT TAAACCATCT 421
GAATTAGTAG CCATCATTTT CAAAAATCAA GAGATGCCAC ATTAAAATAT GGAATGCTGC 481
TGTTCTTGAA AATAATGAAA CATCTGGAAC ATTGAGGCCA CATTCCTGAC TGACAGCAAT 541
CAGTTGGAGC TGCGTAGTGA CTGCCCACTT TACATGGGGC ATCTGATCCC TAGTCGATTA 601
CAGCTGCCAC CACTTCCCTT TATCTCTCTA ATACCAAGCT CTTTTCACTC ATTTTTGTTA 661
CTTAAGAGAT ATTTGGGTTT GAAACCTCTG ATGCAGGTAA TTGAGGGTTA TAGAGCAGAG 721
GACAGATGCT ATCAGAGTTG TCTTTTAAGA AGAACCCTC TGTTCTTCAT TTTGTTGAAG 781
ATAGCCTGGA AGAGGGCAGC CAGGGGAGAA GTTAGGGCTG GAGCTATGAG AAAGCATAAG 841
ATGAGATGAT GGCTTCAACA TTGAGGACAG AAAGAATATT GAGATGAGAA AGTAGTCCAT 901
ATAAGCATCT ATGCAAAGGA AATAGCAGAT GTCCTCAAAT CAGCAGAGGC AACAACTCTG 961
AAAGTTTATT CATAAGCCCC TCTTTTCATC TCCAATCCAG TTCAAATGTA ATTATTTAAA 1021
TTGTTCTTCA CTCTCCTTCC TGGATCATGA ATGAGCTCCT TAAATGCAGG GTCCACAGTG 1081
TCCTATTCAT CAGTGAATTC CAAGTGCCTA GCACAGAGCC TGGCAAATAG TAAATGCTTA 1141
ACAAATATTC GTTCAGTGCA TGAATTGGAG TGATTCTCTA CTTTGCCTCA TAAGTTGAAA 1201
AAAGGTTTAT TACATACCTA AATATGCTGA ATCACAGGG CATTTGGCAA CCCCCCAAAA 1261
CCAAAACTCC CAGTTTGGAA ACAGAATTTT AATTCTGTGA AAATAAAATC CATTCATTTA 1321
TTCAAAAAAT ATTTATTAAA CAATGACCAT GTCCACACCA GGCTGAGTCC TAAGGATTCA 1381
ATGATGAACA AAAACCAACA TGATTCCTGC TCTTAGGAAA CATACAGTTC AGTGAGGAAA 1441
ACAGATTGTG AGAAGTCCTC CAACAAATAC TGGGTGCTAT TAAAATATAT TAAAAGGTGA 1501
GTGGGTGAGG GACTTGAGCT AGCCTAGGTG GTTCAGGAAG TCTTCCTGGA TGTGCTGATA 1561
TGCATAGGCA TTAACTAGAT AAATAGAGAG AAGGATGAAC CAACATTGCA GGTAGAGGGA 1621
ACAGAATATG CAAAGGCAGG AAGGATTATG GAGTCGTTGG AGGACCTGAA TAAAGGCCCA 1681
GTGTAAGTGG ATCTCAGAAA ACAGGAGGAA AGGTGTATGA GATGAGATCA GAGAGGCAGA 1741
TCATGTGGGG TATGGTTAAT GTTTTGGACT TTTCTATTAA GAGCAATGGG GAGACAGTGA 1801
CAGGACTTAA ACGGGGAAAT AATATGACCA GATTAAACTT TCTAAAAAAC CCTCTATGCA 1861
AATATATATT GAGAGTTAAT TATTGACAAA GATTCAAAGG CAACAAAGTG AGAGAGAAT 1921
AGTATTTTCA AAAAATGGTG CCAAAACAAT AGGACATCTA TATTAAAAGT TGGGTATCTG 1981
TCTACAAAAC TTAATTCAAA ATGGATCACA GACCTAAATG TAAAACTGAA AGCTATACAA 2041
CTTCTGGAAG GAAAACACAG ATGGGAATCT GTGTGATCTT GAGTTTGAAA ATGATTTATT 2101
ATATCTGACA CCATAATCCG TAAGTTAACA TAATTCATAA GTGAACAAAG TGATGAACTG 2161
GACTTCATCA GAATTTAAAA TGTTTGTGCT TCAAAAGACA CTGGTATGAT AATGAAGACA 2221
AACTACAGAT AAGATATTGT TGAATCATAT TTCTGATAAA GGAATTGTGG CTCAGAATAC 2281
ATAACTCTAA ACCCCCATAA TAAATTACAA GTAGCCCAAT TAAAAAAAAA AAAAGAGAAA 2341
AAATTTACAG TCTTCATCAA AGAAAGTATC AATTGTAAAA TAAGCACATG AAAAATGCTC 2401
TGCATCTTTA TTCATGGGGG GATGAAATAA AAATTAAATG GGAAAGACAC CTCTAATTAG 2461
AATACTAAAA TTAAAAAGAC TGACCATACC AAGTATTGGT GAAGTGGAAA TGTAAAATGA 2521
TACAATCAAC TTAGGTAGAT GATTTGGAAG TTTCTTACAA AAGTAGGTGT ATACCTACCC 2581
TGTGACTCAC CCATTCCATG GCTAAGTATT TACCTGAGAG AAATGAAAGA ATACATCCAT 2641
ACAAAGATGT TTATACAAAT ATTTATAGCA GTTTTATTTG TAGTAGCCCC AAACTGAAAA 2701
GAACCCAAAT GTCCATCAAA AGTGAATGGA TAAACAAAGC GTGGTACAGC AATGCAATAG 2761
AATACTACTT AGCAATAAAG AAGAATGAGC TAGTGATATA CATAACAGCT TAAATGTACA 2821
TCAAAGGCAT TGTGCTCAGT GAAAGATGCA AGTAAAAAAA AAAAGAGTA CATGCTGTAT 2881
AGTTCCATTG ACATAAAACT CTGGAAAGTG AAAAACAGTC TATACTGACA GAAAGCAGAT 2941
CATTGGTTGC CTGAGGAGGA GGAGTATAGG AGAGGTGGAG GGAAAATGTA CAAAGTGGCA 3001
CAATAAAAAC TTTTGGAATC ATAGATATAT TCACTATCTT GATTGAGTGA TGATTTCATG 3061
```

Fig. 8A

```
AGTGCACGTG CGTGTGTCAA AAATGATCAA TTTATGCAAC TTTAAATATG TGCAGTTTAT 3121
TGTATATATC AATTATACCT CAGTACGGCT ATTAAAAAGA AACCCTCTGG CTGCACAATG 3181
CAGAACTGAT TCTAGGAAAG AGTGGAGGGA GGATGACCAT TTACAGTGCT CCAGGTGGAA 3241
GAGAACGGTG CCTTCTGGAA GTGAACTAGG TTGGCAACAA CAGAGATGAA ATAAATGGGC 3301
AGATGTGTGA GATACTTAGG AAATAAAACC CGATGGTCAC CATTTTCCAA AGGTCAGCTC 3361
ATCCTGGCTT TCCAGAGCAA AGAGCTAGGG AAGACTTTAT TAATAAATCC CTCTTGAAGT 3421
TGCAGAGGAA GCTTATAGCA GAAACTTACT CTCAACCTGA CTAATCTGAG AGAACACCTC 3481
TGGTTCCATT TGATTACTAA AAAACTGCAA AGAACAGGAG GAGAAAGAAG AAGAAAGCTG 3541
GTACAAACAG TGAACTTATA TAATATTAAT CAATAATTGT CTCTTGTTCT TAAAAGCAAT 3601
GGGAAGAAAA TGAGATTTGA GCTGGAAGAT CAGAGTTCAA AATCCAAATA AAGTATATGG 3661
CCCTAATATG CTTATAGTAG TTAACCTTTC CTGATAATGA TATAATTGTT GACAGCACCA 3721
TCTTTAAAAT AAAATAACAT AGTAATCCTT CAGATTGTA GAAGATCTTT CCTGTTTACA 3781
AGTTTGTTCT ATACACATTA TGTCTTTTAA ATGACACACT AGCCTTCTGA GGGTAACTTA 3841
TATTGGCAAC AGTTTTCAGA TGTGGAAACT GTGAAGACAA TGTTGGTGAT GTGGAAGCAA 3901
CATAAACTTT GGAGTCTTTC AGACCCAGGT TTGAATGTCA GACTGCTTTT TATTCAGAGT 3961
AACTTCAGAG CATTATTTCT CACCTTAATT TTTTTCAGG CCTCTTTGTG TCTATGTGTC 4021
CTCTTCACTC CTGTCCATTG TTTCTTCAGT GATTTTGCC ACCTTCCTTC ACTGTTAGTG 4081
TGTAGACACA TAGTTCTCCT GGCTCTGAGA GCCTATGTTA ATTCCATTCT ACCATCCTGC 4141
CACGGCCCAC TCAATTCCTA TTGAGCAATG CTAGTTGAAA GTTGTGGTGG GATTAAATGT 4201
TGCAATGAGT ATTCAAATGA GGTTGAAGTA TCTACGCATT CTACTTACAT ATGGTGAGGT 4261
ATATTCAAGG AAGCTGTAGC CATTAAAATC TCAGGAAATA ATTTTTCACC TCCTCAGGTG 4321
AAAGGGTCTT CAGGCCTTTG TGTTCTGGAA GGTTCATTTA TAGCCATTTC CCAAATGACA 4381
ATGCGATTGA TGAGTCTAGA GTCTAGCTCA AATAGCAATG GACTGGAAGA CTAGTTTAGG 4441
TTTTACTAAT GTGGAACATA GAACAAATTA TGTCCTTGTT TCAGCCTGTT CATCTGTGAA 4501
ATAGAGCCTA TCATATCCAG TCTTCCTTGC CTTTAGGTTT GAGTTACCTT CTTTGGTCAA 4561
GGTAAGTAAA TGCCTATGAT GTTTGGCTGT GCACAAGATA AAGCTACAAC AAAGCTACAA 4621
CCCATCTTTT CTCTGTAGAA GACTCAAAAA GCAAAGAGA CCCAGGAAAA TCTCGGAATG 4681
ACTTTTGGAA CAGAGAGCCT CCCCAGAATC AGAAGTCAAG GAATTAAAC ATAGGGAAGG 4741
CCCAGGTCTC TACTGACATA AAGGAAAGAT GTTTCTTAT AGGTTTCACG TTTACATTTT 4801
CTCTCTCTTG ATCCCATTCC CACTTGCATC TGCCACCTTT ACACAGGGCT TATGGGACCT 4861
CCTCCACAAA AGAGCAGTTG CAGTAACCCA CATCATCCTC TACGCCCTGG CTGTCCATCA 4921
AGAGGCGAAA AGCAGCCCTA TATAGGTTCT ATCCTTGGAT AGTTCCAGTT GTAAAGTTTA 4981
AAATATGCGA AGGCAACTTG GAAAAGCAAG CGGCTGCATA CAAAGCAAAC GTTTACAGAG 5041
CTCTGGACAA AATTGAGCGC CTATGTGTAC ATGGCAAGTG TTTTTAGTGT TTGTGTGTTT 5101
ACCTGCTTGT CTGGGTGATT TTGCCTTTGA GAGTCTGGAG AGTAGAAGTA CTGGTTAAAG 5161
GAACTTCCAG ACAGGAAGAA GGCAGAGAAG AGGGTAGAAA TGACTCTGAT TCTTGGGGCT 5221
GAGGGTTCCT AGAGCAAATG GCACAATGCC ACGAGGCCCG ATCTATCCCT ATGACGGAAT 5281
CTAAGGTTTC AGCAAGTATC TGCTGGCTTG GTCATGGCTT GCTCCTCAGT TTGTAGGAGA 5341
CTCTCCCACT CTCCCATCTG CGCGCTCTTA TCAGTCCTGA AAAGAACCCC TGGCAGCCAG 5401
GAGCAGGTAT TCCTATCGTC CTTTTCCTCC CTCCCTCGCC CCACCCTGTT GGTTTTTAG 5461
ATTGGGCTTT GGAACCAAAT TTCCTGAGTG CTGGCCTCCA GGAAATCTGG AGCCCTGGCG 5521
CCTAAACCTT GGTTTAGGAA ACCAGGAGCT ATTCAGGAAG CAGGGGTCCT CCAGGGCTAG 5581
AGCTAGCCTC TCCTGCCCTC GCCCACGCTG CGCCAGCACT TGTTTCTCCA AAGCCACTAG 5641
GCAGGCGTTA GCGCGCGGTG AGGGGAGGGG AGAAAAGGAA AGGGGAGGGG AGGGAAAAGG 5701
AGGTGGGAAG GCAAGGAGGC CGGCCCGGTG GGGGCGGGAC CCGACTCGCA AACTGTTGCA 5761
TTTGCTCTCC ACCTCCCAGC GCCCCCTCCG AGATCCCGGG GAGCCAGCTT GCTGGGAGAG 5821
CGGGACGGTC CGGAGCAAGC CCACAGGCAG AGGAGGCGAC AGAGGGAAAA AGGGCCGAGC 5881
TAGCCGCTCC AGTGCTGTAC AGGAGCCGAA GGGACGCACC ACGCCAGCCC CAGCCCGGCT 5941
CCAGCGACAG CCAACGCCTC TTGCAGCGCG GCGGCTTCGA AGCCGCCGCC CGGAGCTGCC 6001
CTTTCCTCTT CGGTGAAGTT TTTAAAAGCT GCTAAAGACT CGGAGGAAGC AAGGAAAGTG 6061
```

Fig. 8B

```
CCTGGTAGGA CTGACGGCTG CCTTTGTCCT CCTCCTCTCC ACCCCGCCTC CCCCCACCCT 6121
GCCTTCCCCC CCTCCCCCGT CTTCTCTCCC GCAGCTGCCT CAGTCGGCTA CTCTCAGCCA 6181
ACCCCCCTCA CCACCCTTCT CCCCACCCGC CCCCCCGCCC CCGTCGCCCA GCGCTGCCAG 6241
CCCGAGTTTG CAGAGAGGTA ACTCCCTTTG GCTGCGAGCG GGCGAGCTAG CTGCACATTG 6301
CAAAGAAGGC TCTTAGGAGC CAGGCGACTG GGAGCGGCT TCAGCACTGC AGCCACGACC 6361
CGCCTGGTTA GGCTGCACGC GGAGAGAACC CTCTGTTTTC CCCCACTCTC TCTCCACCTC 6421
CTCCTGCCTT CCCCACCCCG AGTGCGGAGC CAGAGATCAA AAGATGAAAA GGCAGTCAGG 6481
TCTTCAGTAG CCAAAAAACA AAACAAACAA AAACAAAAAA CAAGAAATAA AGAAAAAGA 6541
TAATAACTCA GTTCTTATTT GCACCTACTT CAGTGGACAC TGAATTTGGA AGGTGGAGGA 6601
TTTTGTTTTT TTCTTTTAAG ATCTGGGCAT CTTTTGAATC TACCCTTCAA GTATTAAGAG 6661
ACAGACTGTG AGCCTAGCAG GGCAGATCTT GTCCACCGTG TGTCTTCTTC TGCACGAGAC 6721
TTTGAGGCTG TCAGAGCGCT TTTTGCGTGG TTGCTCCCGC AAGTTTCCTT CTCTGGAGCT 6781
TCCCGCAGGT GGGCAGCTAG CTGCAGCGAC TACCGCATCA TCACAGCCTG TTGAACTCTT 6841
CTGAGCAAGA GAAGGGGAGG CGGGGTAAGG GAAGTAGGTG GAAGATTCAG CCAAGCTCAA 6901
GGATG
```

Fig. 8C

```
                      CA GGCCCCACAA AACCTAGATC TGCCCCAGTA TAACTAAATC 1501
TGGGACCATT TATTGAGCAA TTATTATGTG CCAAGTATTG CGCTGAGTGC TTCCAGAGCA 1561
TTATCTCCTT TAACCCCAGC ATAGTATGTC AGATGCTGTT TTACAGATGA GCCAACTGAG 1621
ACCAGAGATG CTCAGTCACT TGCCCAAGGT GACATGACTG ATATGGAATA GAGTCAAGAT 1681
TTTTTTTTTT TTTTTGACA CGGAGTCTCA CTCTGTCTCC CAGGCTGGAG TGCAGAGGCG 1741
CAATCTCAGC TCACTGCAAG CTCTGCCTCC CAGGTTCACG CATTCTCCTG CCTCAGCCTC 1801
CTGAGTAGCT GGGACTACAG GCACCCGCCA CCACACCTGG CTAATTTTTT GTATTTTTAG 1861
CAGAGACAGG GTTTCACCGT GTTAGCCAGG ATGGTCTCGA TCTCCTGACC TCGTGATCTG 1921
CCTGCCTCGG CCTCCCAAAG TGATGGAATT ACAGGTGTGA GCCACCGCGA CTGGCCAGAT 1981
TCAAGATTTG AACCCAGGTC CTCTTGGTCC CAGAGGCCCC TGTTTCTCAA CTCCCTAGCA 2041
TGCATACGCA CCTGTCCCTC TAGAGGTGCC TGCTTAAGTG TGCTCAGCAC ATGGAAGCAA 2101
GTTAGAAATG CTAGGTATAC CTGTAAAGAG GTGTGGGAGA TGGGGGGGAG GGAAGAGAGA 2161
AAGAGATGCT GGTGTCCTTC ATTCTCCAGT CCCTGATAGG TGCCTTTGAT CCCTTCTTGA 2221
CCAGTATAGC TGCATTCTTG GCTGGGCAT TCCAACTAGA ACTGCCAAAT TTAGCACATA 2281
AAAATAAGGA GGCCCAGTTA AATTTGAATT TCAGATAAAC AATGAATAAT TTGTTAGTAT 2341
AAATATGTCC CATGCAATAT CTTGTTGAAA TTAAAAAAAA AAAAAAAGT CTTCCTTCCA 2401
TCCCCACCCC TACCACTAGG CCTAAGGAAT AGGGTCAGGG GCTCCAAATA GAATGTGGTT 2461
GAGAAGTGGA ATTAAGCAGG CTAATAGAAG GCAAGGGGCA AGAAGAAAC CTTGAATGCA 2521
TTGGGTGCTG GGTGCCTCCT TAAATAAGCA AGAAGGGTGC ATTTTGAAGA ATTGAGATAG 2581
AAGTCTTTTT GGGCTGGGTG CAGTTGCTCG TGGTTGTAAT TCCAGCACTT TGGGAGGCTG 2641
AGGCGGGAGG ATCACCTGAG CTTGGGAGTT CAAGACCAGC CTCACCAACG TGGAGAAACC 2701
CTGTCTTTAC TAAAAATACA AAAAATTCAG CTGGTCATGG TGGCACATGC CTGTAATCCC 2761
AGCTGCTCGG GAGGCTGAGG CAGGAGAATC ACTTGAACCA GGGAGGCAGA GGTTGTGGTG 2821
AGCAGAGATC GCGCCATTGC TCTCCAGCCT GGGCAACAAG AGCAAAAGTT CGTTTAAAAA 2881
AAAAAAAAAG TCCTTTCGAT GTGACTGTCT CCTCCCAAAT TTGTAGACCC TCTTAAGATC 2941
ATGCTTTTCA GATACTTCAA AGATTCCAGA AGATATGCCC CGGGGGTCCT GGAAGCCACA 3001
AGGTAAACAC AACACATCCC CCTCCTTGAC TATCAATTTT ACTAGAGGAT GTGGTGGGAA 3061
AACCATTATT TGATATTAAA ACAATAGGCT TGGGATGGAG TAGGATGCAA GCTCCCAGG 3121
AAGTTAGATA ACTGAGACTT AAAGGGTGTT AAGAGTGGCA GCCTAGGGAA ATTTATCCCG 3181
GACTCCGGGG GAGGGGCAG AGTCACCAGC CTCTGCATTT AGGGATTCTC CGAGGAAAAG 3241
TGTGAGAACG GCTGCAGGCA ACCCAGGCGT CCCGGCGCTA GGAGGGACGA CCCAGGCCTG 3301
CGCGAAGAGA GGGAGAAAGT GAAGCTGGGA GTTGCCGACT CCCAGACTTC GTTGGAATGC 3361
AGTTGGAGGG GGCGAGCTGG GAGCGCGCTT GCTCCCAATC ACCGGAGAAG GAGGAGGTGG 3421
AGGAGGAGGG CTGCTTGAGG AAGTATAAGA ATGAAGTTGT GAAGCTGAGA TTCCCCTCCA 3481
TTGGGACCGG AGAAACCAGG GGAGCCCCCC GGGCAGCCGC GCGCCCCTTC CCACGGGGCC 3541
CTTTACTGCG CCGCGCGCCC GGCCCCACC CCTCGCAGCA CCCCGCGCCC CGCGCCCTCC 3601
CAGCCGGGTC CAGCCGGAGC CATGG
```

Fig. 9

PROMOTERS FOR REGULATED GENE EXPRESSION

This application claims priority of U.S. Provisional Patent Application No. 60/209,549 filed Jun. 6, 2000, which is incorporated in its entirety herein by reference.

FIELD OF THE INVENTION

The present invention relates to regulatory sequences within various promoters, and to heterologous nucleic acid constructs, vectors and transformation methods employing such sequences. The invention further relates to modified promoters and their use in regulated gene expression.

REFERENCES

Albanese, et al., *Journal of Biological Chemistry* 270, 23589–23597, 1995.
Allen et al., *Science* 259, 990–3, 1993.
Arber et al., *Cancer Research* 57, 1569–1574, 1997.
Arthur M et al., *J. Bacteriol.* 174(8):2582–2591, 1992.
Aruffo et al., *Cell* 72, 291–300, 1993.
Beier et al., *Proceedings of the National Academy of Sciences (USA)* 96, 1433–1438, 1999.
Biancone et al., *International Journal of Molecular Medicine*, 3:343–53, 1999.
Boyce, et al., *J Clin Microbiol* 32, 1148–53, 1994.
Buckley, *Oncogene* 8, 2127–2133, 1993.
Buhlmann and Noelle, *Journal of Clinical Immunology*, 16:83–9, 1996.
CDC.MMWR 42:597–9, 1993.
DiSanto et al., *Nature*, 361, 541–3, 1993.
Foy et al., *Annu Rev Immunol.* 14:591–617, 1996.
Gansauge et al., *Cancer Research* 57, 1634–1637, 1997.
Gauchat et al., *FEBS Letts.* 315, 259–66, 1993.
Graf et al., *Eur. J. Immunol.*, 22, 3191–4, 1992.
Grewal and Flavell, *Immunol Rev* 153:85–106, 1996.
Haldimann, et al., *J Bacteriol.* 179(18):5903–13, 1997.
Hall et al., *Advances in Cancer Research* 68, 67–108, 1996.
Hancock et al., *Nature Medicine*, 4, 1392–6, 1998.
Handwerger, et al., *Clin Infect Dis* 16, 750–5, 1993.
Herber et al., *Oncogene* 9, 1295–1304, 1994a, 1994b.
Hinz et al., *Molecular and Cellular Biology* 19, 2690–2698, 1999.
Hollenbaugh et al., *EMBO J.*, 11, 4313–21, 1992.
Holman T R, et al., *Biochemistry* 33(15):4625–31, 1994).
Jiang et al., *Oncogene* 8, 3447–3457, 1993.
Kay et al., *PNAS*, 94:4686–91, 1997.
Kirk et al., *Science,* 94:8789–94, 1997.
Kornmann et al., *Clin. Invest.* 101, 344–352, 1998.
Korthauer et al., *Nature,* 361, 539–41, 1993.
Lander et al., *Antimicrob. Agents and Chemo.* 41:1715–1720, 1997.
Larsen et al., *Nature,* 381:434–8, 1996.
Lee et al., *Journal of Biological Chemistry* 274, 7341–7350, 1999.
MA et al., *Proc. Nat. Acad. Sci.* 84:1005–1009, 1987.
Marshall C G et al., *Biochemistry* 38(26):8485–91, 1999.
Matsumura et al., *The EMBO Journal* 18, 1367–1377, 1999.
Moellering R C Jr., *Clin Infect Dis* 14, 1173–8, 1992.
Motokura & Arnold, *Genes Chromosomes Cancer,* 7:89–95, 1993.
Murray B E, *Clin Microbiol Rev.* 3, 46–65, 1990.
Niimi et al., *J. Immunol.,* 161, 5331–7, 1998.
Ochs et al., *Res Immunol* 145(3):210–5; discussion 244–9, 1994.
Quelle et al., *Genes and Development* 7, 1559–1571, 1993.
Philipp et al., *Molecular and Cellular Biology* 14, 4032–4043, 1994.
Resnitzky et al., *Molecular and Cellular Biology* 14, 1669–1679, 1994.
Robinson, et al., *J Virol* 14:384–391, 1974.
Sattler et al., *J Virol* 32:226–233, 1979.
Schaberg D R et al., *Am J Med* 91(Suppl 3B), 72S-75S, 1991.
Sherr, *Cell* 73, 1059–1065, 1993.
Sherr, *Science* 274, 1672–1677, 1996.
Shimadzu et al., *Biochim. Biophys. Acta,* 1260, 67–72, 1995.
Shtutman et al., *Proceedings of the National Academy of Sciences (USA)* 96, 5522–5527, 1999.
Silva J C, et al., *Proc Natl Acad Sci (USA),* 95(20):11951–6, 1998.
Spriggs et al., *J. Exp. Med.,* 176:1543–50, 1992.
Stoll V S et al., *Protein Sci*7 (5):1147–55, May 1998.
Sudo et al., *Microbiol. Immunol.* 40(2) 153–159, 1996
Summers et al., *Proc. Nat. Acad. Sci. (USA)* 72:4597–4601, 1975
Tetsu et al., *Nature* 398, 422–426, 1999.
Walsh C, *Science,* 284(5413):442–3, 1999.
Wang et al., *Nature* 369, 669–671, 1994.
Watanabe et al., *Journal of Biological Chemistry* 271, 22570–22577, 1996.
Watanabe et al., *Molecular and Cellular Biology* 18, 3212–3222, 1998.
Withers et al., *Mol Cell Biol.* 11(10):4846–53, 1991.
Xiong et al, *Cell* 17;65(4):691–9, 1991.
Yan et al., *Journal of Biological Chemistry* 272, 33181–33190, 1997.
Yang et al., *Journal of Virology,* 70, 6370–7, 1996.
Zhang et al., *Cancer Research* 57, 169–175, 1997.
Zhou et al, *Oncogene* 11, 571–580, 1995.

BACKGROUND OF THE INVENTION

Gene expression in prokaryotes and eukaryotes is a highly regulated process. Inappropriate expression (over-expression or under-expression) of "normal" or "healthy" genes is associated with many diseases and disease processes. Similarly, expression of mutated genes is also associated with many diseases. Controlling the expression of these genes is one of the ways through which diseases can be treated.

All genes contain transcriptional regulatory sequences upstream and downstream from the transcription start site. Transcription factors recognize and bind to transcriptional regulatory sequences and control the production of message transcribed from the gene. Transcriptional regulatory nucleic acid sequences involved in the regulation of gene expression include promoters, enhancers, and regulatory sequences to which transcription factors or transcriptional regulatory proteins bind, which are required for initiation of transcription. Although transcriptional regulatory sequences are most frequently found just upstream of the transcription start site, they can also be found much further upstream, or on the 3' of the gene, or within the introns and exons that make up a gene.

A promoter is a region in a DNA sequence generally 1 to about 100 or 200 basepairs upstream of the transcription start site of a gene and typically contains or is adjacent to one or more transcription factor binding sites. An enhancer is a region in a DNA sequence that generally functions to increase transcription of a gene under its control. Enhancers are found upstream and/or downstream from the transcription start site. Enhancers can be located hundreds or even thousands of basepairs away from the transcription start site.

Transcription factors bind to promoters and enhancers to regulate transcription.

The sequences of numerous transcriptional regulatory sequences are known in the art, some of which can be found in the "Eukaryotic Promoter Database" developed and maintained by members of the Bioinformatics Group of the ISREC (Swiss Institute for Experimental Cancer Research), which is avalable on the Internet. However, absent a thorough analysis of the function of particular sequences found within a given promoter or enhancers, it is impossible to determine whether the particular sequences are important in regulating gene transcription. Once transcriptional regulatory sequences have been identified, they may be utilized to regulate expression of the endogenous genes and may be incorporated into heterologous nucleic acid constructs for use in regulated expression of transgenes. Accordingly, it is of interest to identify and characterize the transcriptional regulatory regions of genes. Of particular interest are the regulatory regions of genes associated with various disease conditions, examples of which are described below.

Mammalian cyclin D1 (CCND1, also named PRAD1 or BCL1) has applications to a number of cancers including but not limited to breast cancers, colon cancers and pancreatic cancers, and plays a critical role in regulating the GOES checkpoint of the cell cycle of normal mature animal cells. (See Sherr, 1996)

CD40L ligand (CD40L) (also referred to as gp39, CD154, TRAP or T-BAM) plays a critical role in T cell dependent humoral immune responses by interacting with CD40, which provides a signal needed for T cell activation and recognition of antigen-MHC complexes by the T cell receptor.

Viral induced Hepatitis B (HBV) in humans is estimated to have infected 300 million people worldwide, with a small but significant number of infected individuals developing severe pathologic consequences, including chronic hepatic insufficiency, cirrhosis, and hepatocellular carcinoma. HBV-specific promoters involved in viral replication are therefore relevant to both therapy of HBV disease and regulated gene expression which is specific to liver cells.

The vancomycin resistance enzyme VanH has been associated with the recently observed increase in the incidence of infection and colonization with vancomycin-resistant enterococci (VRE). Therefore, regulated expression of VanH is relevant to treatment of VRE.

Prostate cancer is the most frequently diagnosed cancer in males in the United States. Current treatments for metastatic prostate cancer involve targeting the androgen receptor (AR) using surgical or chemical means. Regulated expression of the androgen receptor is relevant to treatment of prostate cancer.

Her2 (human epidermal growth factor receptor2; c-erbB2, neu) is a tyrosine kinase growth factor receptor which is overexpressed by breast cancer cells, ovarian cancer cells and a variety of other cancer cells. Accordingly, regulated expression of Her-2 is relevant to modulating such overexpression.

The β-lactamase gene confers ampicillin resistance to *E. coli*. Accordingly, regulated expression of β-lactamase is relevant to modification of such antibiotic resistance.

The present invention provides the sequences of the transcriptional regulatory regions of genes associated with various disease conditions together with a functional characterization of such sequences.

SUMMARY OF THE INVENTION

The invention is directed to characterization of endogenous regulatory sites in the regulatory region of native gene promoters and their use in regulated gene expression.

In one aspect, the invention provides isolated nucleic acid sequences comprising the regulatory region of a cyclin D1 promoter, characterized by the ability to regulate expression of a gene operably linked to a cyclin D1 promoter which includes the regulatory sequence. Exemplary sequences are presented as SEQ ID NO.:5, SEQ ID NO.:6 and SEQ ID NO.:8.

In another aspect, the invention provides isolated nucleic acid sequences comprising the regulatory region of a CD40L promoter, characterized by the ability to regulate expression of a gene operably linked to a CD40L promoter which includes the regulatory sequence. Exemplary sequences are presented as SEQ ID NO.:12, SEQ ID NO.:13, SEQ ID NO.:14 and SEQ ID NO.:15.

In a further aspect, the invention provides isolated nucleic acid sequences comprising the regulatory region of an HBV promoter, characterized by the ability to regulate expression of a gene operably linked to an HBV core, preS1 or X promoter which includes the regulatory sequence. Exemplary sequences are presented as SEQ ID NO.:20 and SEQ ID NO.:21 (core promoter); SEQ ID NO.:23 or SEQ ID NO.:24 (preS1 promoter); and SEQ ID NO.:26, SEQ ID NO.:27 and SEQ ID NO.:28 (HBV X promoter).

The invention also provides isolated nucleic acid sequences comprising the regulatory region of a vancomycin-resistant enterococci (VRE) promoter, characterized by the ability to regulate expression of a gene operably linked to a VRE promoter which includes the regulatory sequence. Exemplary sequences are presented as SEQ ID NO.:32, SEQ ID NO.:33 and SEQ ID NO.:34.

The invention further provides isolated nucleic acid sequences comprising the regulatory region of an androgen receptor (AR) promoter, characterized by the ability to regulate expression of a gene operably linked to a AR promoter which includes the regulatory sequence. Exemplary sequences are presented as SEQ ID NO.:64, SEQ ID NO.:65 and SEQ ID NO.:66.

In another aspect, the invention provides isolated nucleic acid sequences comprising the regulatory region of a HER2 promoter, characterized by the ability to regulate expression of a gene operably linked to a HER2 promoter which includes the regulatory sequence. Exemplary sequences are presented as SEQ ID NO.:70, SEQ ID NO.:71 and SEQ ID NO.:72.

The invention further provides isolated nucleic acid sequences comprising the regulatory region of an androgen receptor beta lactamase (Bla) promoter, characterized by the ability to regulate expression of a gene operably linked to a Bla promoter which includes the regulatory sequence. Exemplary sequences are presented as SEQ ID NO.:77 or SEQ ID NO.:78.

In a related aspect the invention provides a vector comprising a promoter regulatory nucleic acid sequence for any one of: a cyclin D1 promoter, a CD40L promoter, three HBV promoters (core, pre-S1 and HBV-X), a vancomycin-resistant enterococci (VRE) promoter, an androgen receptor promoter, a Her2 promoter, and a β-lactamase promoter, as described above.

The vector may be an expression vector which includes the promoter regulatory sequence operably linked to a promoter and control sequences recognized by a host cell transformed with the vector; and a transgene encoding a gene product, e.g., a reporter gene.

A host cell comprising such a vector, e.g., a prokaryotic cell, a eukaryotic cell, or a mammalian cell is also provided by the invention. A host cell transformed with such a vector may be used in a method for regulating expression of a transgene and detecting the expression thereof, e.g., by exposing the cell to a cellular factor or a DNA binding compound which interacts with the promoter regulatory sequence.

BRIEF DESCRIPTION OF THE FIGURES

FIG. 1A presents the sequence of the HBV core promoter (SEQ ID NO:16).

FIG. 1B presents the sequence of the HBV pre-S1 promoter region (SEQ ID NO:22) with the sequences of various DNA response elements (HNF1, HNF3, Sp1 and TBP) indicated as underlined with sequence locations indicated in the figure.

FIG. 3 presents the sequence of the HBV X promoter region (SEQ ID NO:25) with the sequences of various DNA response elements (NF1, 2c, EF-C, NF-1 and X-PBP) indicated as underlined in the figure.

FIG. 4 presents the sequence of the wild type cyclin D1 promoter (SEQ ID NO:1) from—1745 to +155, which corresponds to nucleotides 316 to 2161 of GenBank Accession No. L09054.

FIGS. 5A to C present the sequence of the full-length human CD40L sequence (SEQ ID NO:9) numbered from nucleotide 1 to 2395, wherein nucleotides 10 to 1919 correspond to the human CD40L promoter sequence identified as −1860 to +49.

FIG. 6 presents the sequence of the wild type vanH promoter (SEQ ID NO:31).

FIGS. 8A to C present the sequence of the wild type androgen receptor promoter (SEQ ID NO:35) from −6000 to +1100.

FIG. 9 presents the sequence of the wild type Her2 promoter (SEQ ID NO:67).

DETAILED DESCRIPTION OF THE INVENTION

I. Definitions

Figure 2:
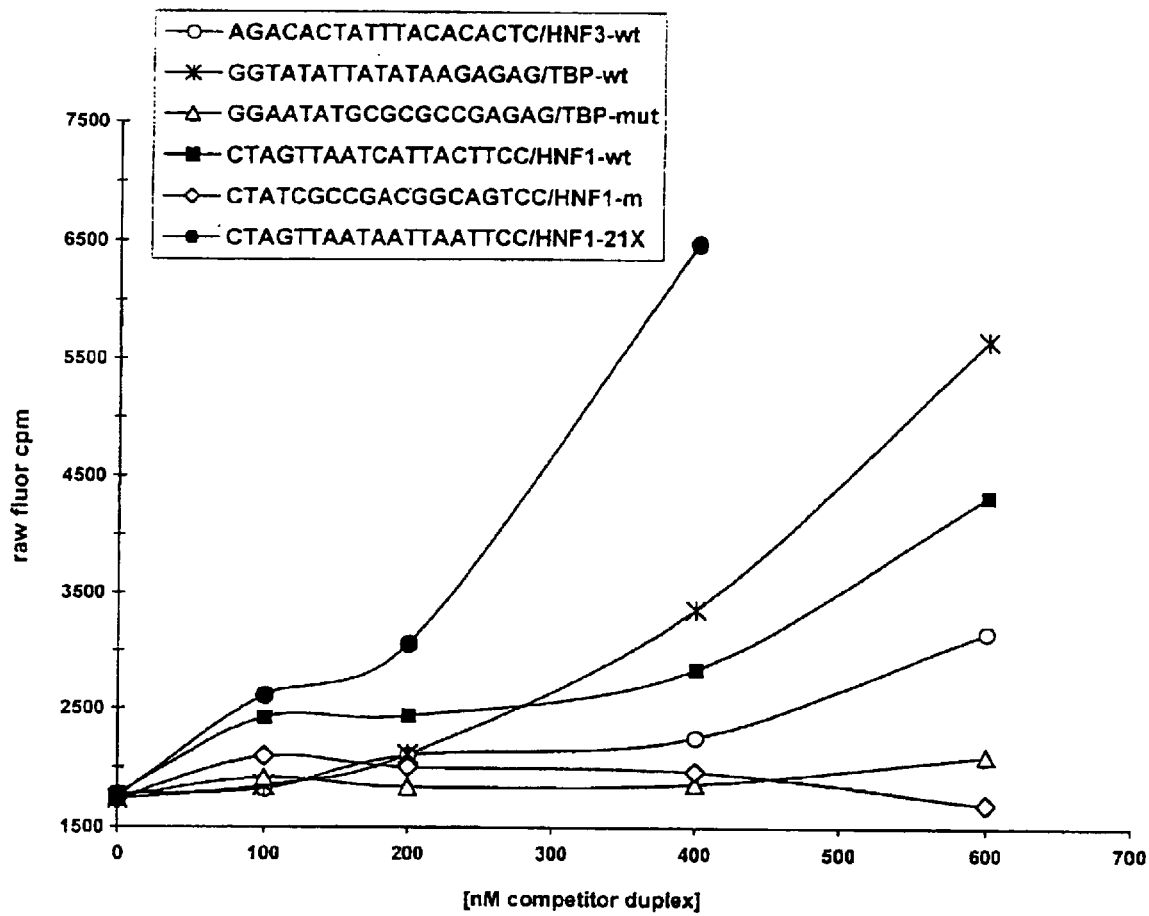
FIG. 2 depicts teh results of a hybridization stabilization assay (HSA) with various HBV preS1 promoter constructs indicating the binding preference of a test compound, the netropsin dimer, 21x, for the HNF3-wt, TBP-wt, TBP-mut, HNF-1-wt, HNF1-m and HNF1–21x sequences (SEQ ID NOS:241–246), indicated in the figure.

As used herein, the term "polynucleotide" refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically adenosine, guanosine, cytosine, thymidine, uracil and inosine. Polymeric molecules include double and single stranded ribonucleic acids (RNA) and deoxyribonucleic acids (DNA), and may include polymers having backbone modifications such as methylphosphonate linkages.

As used herein, a nucleic acid may be double stranded, single stranded, or contain portions of both double stranded or single stranded sequence. The depiction of a single strand also defines the sequence of the other strand and thus also includes the complement of the sequence.

As used herein, the term "recombinant nucleic acid" refers to a nucleic acid, originally formed in vitro, in general, by the manipulation of the nucleic acid in a form not normally found in nature.

A "heterologous nucleic acid construct" has a sequence portion that is not native to the cell in which it is expressed. Heterologous, with respect to a control sequence/coding sequence combination refers to a control sequence (i.e., promoter or enhancer) and a coding sequence or gene combination, that is not found together in nature, in other words, the promoter does not regulate the expression of the same gene in the heterologous nucleic acid construct and in nature. Generally, heterologous nucleic acid sequences are not endogenous to the cell or part of the genome in which they are present and have been added to the cell, by transfection, microinjection, electroporation, or the like. Such a heterologous nucleic acid construct may also be referred to herein as an "expression cassette".

As used herein, the term "sequence identity" means nucleic acid or amino acid sequence identity between two or more sequences, when aligned using a sequence alignment program. Sequence searches are preferably carried out using the BLASTN program when evaluating the % identity of a given nucleic acid sequence relative to nucleic acid sequences in the GenBank DNA Sequences and other public databases. The BLASTX program is preferred for searching nucleic acid sequences which have been translated in all reading frames against amino acid sequences in the GenBank Protein Sequences and other public databases. Both BLASTN and BLASTX are run using default parameters with an open gap penalty of 11.0, and an extended gap penalty of 1.0, and utilize the BLOSUM-62 matrix. [See, Altschul et al., 1997.]

The term "% homology" is used interchangeably herein with the term "% identity" and refers to the level of identity between two sequences, i.e. 70% homology means the same thing as 70% sequence identity as determined by a defined algorithm, and accordingly a homologue of a given sequence has at least about 70%, preferably about 80%, more preferably about 85%, even more preferably about 90% sequence identity over a length of the given sequence.

A preferred alignment of selected sequences in order to determine "% identity" between two or more sequences, is performed using the CLUSTAL-W program in MacVector version 6.5, operated with default parameters, including an open gap penalty of 10.0, an extended gap penalty of 0.1, and a BLOSUM 30 similarity matrix.

A nucleic acid sequence is considered to be "selectively hybridizable" to a reference nucleic acid sequence if the two sequences specifically hybridize to one another under moderate to high stringency hybridization and wash conditions. Exemplary conditions include hybridization conducted as described in the Bio-Rad Labs ZetaProbe manual (Bio-Rad Labs, Hercules, Calif.), expressly incorporated by reference herein. For example, hybridization is conducted in 1 mM EDTA, 0.25 M $Na_2HPO_4$ and 7% SDS at 60° C., followed by washing in 1 mM EDTA, 40 mM $NaPO_4$, 5% SDS, and 1 mM EDTA, 40 mM $NaPO_4$, 1% SDS. Hybridization conditions are further recited in Ausubel FM et al., 1993, expressly incorporated by reference herein.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

As used herein, the term "plasmid" refers to a circular double-stranded (ds) DNA construct used as a vector, which forms an extrachromosomal self-replicating genetic element in many bacteria and some eukaryotes.

As used herein, the term "gene" means the segment of DNA involved in producing a polypeptide, which may or may not include regions preceding and following the coding region. For example, 5' untranslated (5' UTR) or "leader" sequences and 3' UTR or "trailer" sequences, as well as intervening sequences (introns) between individual coding segments (exons), may or may not be included in the DNA segment designated as the gene.

As used herein the term "transgene" refers to the portion of a heterologous nucleic acid construct, expression cassette or vector which comprises the coding sequence for a polypeptide, wherein the gene is associated with other components, i.e., a promoter with which it is not normally associated in nature.

As used herein, the term "DNA response element" may be used interchangeably with the term "regulatory promoter sequence" and refers to the DNA binding site or sequence for a transcriptional regulatory protein, which may be the same as, overlapping, or adjacent to, a compound-binding sequence.

As used herein, the terms "compound binding sequence", "compound binding site", "ligand binding sequence", and "ligand binding site" are used interchangeably and refer to the portion of a DNA sequence with which a compound, ligand, or molecule interacts resulting in the modified binding of a transcriptional regulatory protein to its DNA binding site (or DNA response element). In some cases, the compound, ligand, or molecule may also be designated a compound or inducer. The "compound-binding sequence" or equivalent is in the vicinity of the DNA response element for transcriptional regulatory protein and may be adjacent (i.e., flanking), overlapping, or the same as the DNA binding site for a transcriptional regulatory protein.

As used herein, the term "promoter" refers to a sequence of DNA that functions to direct transcription of a gene that is operably linked thereto. The promoter may or may not include control sequences (also termed "transcriptional and translational regulatory sequences"), involved in expression of a given gene product. In general, transcriptional and translational regulatory sequences include, but are not limited to, the promoter sequence, include the DNA response element for a transcriptional regulatory protein, ribosomal binding sites, transcriptional start and stop sequences, translational start and stop sequences, and enhancer or activator sequences. The promoter may be native or non-native to the cell in which it is found.

As used herein, the terms "regulatable promoter", "inducible promoter" and "switchable promoter", are used interchangeably and refer to any promoter the activity of which is affected by a cis or trans acting factor.

A eukaryotic gene control region consists of a promoter plus regulatory DNA sequences (to which transcriptional regulatory proteins bind). As used herein, the term "regulatory promoter sequence" generally refers to a sequence within the control region of a gene and to which transcriptional regulatory proteins bind, resulting in transcriptional activation or repression. Native forms of such regulatory promoter sequences are generally located 5' to the promoter elements of the gene control region.

As used herein, the terms "transcriptional regulatory protein", "transcriptional regulatory factor" and "transcription factor" may be used interchangeably with the term "DNA-binding protein" and refer to a cytoplasmic or nuclear protein that binds a DNA response element and thereby transcriptionally regulates the expression of an associated gene or genes. Transcriptional regulatory proteins generally bind directly to a DNA response element, however in some cases binding to DNA may be indirect by way of binding to another protein which in turn binds to, or is bound to the DNA response element.

As used herein, the term "operably linked" relative to a recombinant DNA construct or vector means a nucleotide component of the recombinant DNA construct or vector is in a functional relationship with another nucleotide component of the recombinant DNA construct or vector. For example, a promoter or enhancer is operably linked to a coding sequence if it affects the transcription of the coding sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

As used herein, the term "expression" refers to the process by which a polypeptide is produced based on the information contained in a given DNA sequence. The process includes both transcription and translation.

As used herein, the term "modulated expression" refers to a change in transcription and translation, which may represent an increase or a decrease in the amount of a given gene product.

A host cell has been "transformed" by exogenous or heterologous DNA when the DNA has been introduced into the cell. Transformation may or may not result in integration (covalent incorporation) into the chromosomal DNA of the cell. For example, in eukaryotic cells such as yeast and mammalian cells, the transfected DNA may be maintained on an episomal element such as a plasmid.

As used herein, the terms "stably transformed", "stably transfected" and "transgenic" refer to cells that have a non-native (heterologous) nucleic acid sequence integrated into the genome. Stable transformation is demonstrated by the establishment of cell lines or clones comprised of a population of daughter cells containing the transfecting DNA.

In some cases, "transformation" is not stable, i.e., it is transient. In the case of transient transformation, the exogenous or heterologous DNA is expressed, however, the introduced sequence is not integrated into the genome.

As used herein, the term "co-transformed" refers to a process by which two or more recombinant DNA constructs or vectors are introduced into the same cell. "Co-transformed" may also refer to a cell into which two or more recombinant DNA constructs or vectors have been introduced.

As used herein, the term "sequence preferential binding" refers to the binding of a molecule to DNA in a manner that indicates a preference for binding to a certain DNA sequence relative to others.

As used herein, the term "sequence specific binding" refers to the binding of a molecule to DNA in a manner that indicates a strong binding preference for a particular DNA sequence.

As used herein, the term "sequence-dependent binding" refers to the binding of molecules to DNA in a manner that is dependent upon the target nucleotide sequence. Such binding may be "sequence-preferential" or "sequence-specific".

As used herein, the term "inhibit binding" relative to the effect of a given concentration of a particular compound on the binding of a transcriptional regulatory protein to its DNA response element refers to a decrease in the amount of binding of the transcriptional regulatory protein to its DNA response element relative to the amount of binding in the absence of the same concentration of the particular compound, and includes both a decrease in binding as well as a complete inhibition of binding.

As used herein, the terms "compound", "molecule", "ligand" and "inducer" are used interchangeably and refer to molecules or ligands characterized by sequence-preferential or sequence-specific binding to DNA at a sequence which is adjacent (i.e., flanking), overlapping, or the same as, the DNA binding site for a transcriptional regulatory protein.

As used herein, the terms "modulate" and "modify" are used interchangeably and refer to a change in biological activity. Modulation may relate to an increase or a decrease in biological activity, binding characteristics, or any other biological, functional, or immunological property of the molecule.

As used herein, the term "regulate gene expression" relative to a promoter of the invention means the promoter has the ability to increase or decrease the expression of, and may be used to modulate the level of expression of a gene operably linked thereto.

As used herein, the terms "native", "natural" and "wild-type" relative to a particular nucleic acid sequence, trait or phenotype refers to the form in which that nucleic acid sequence, trait or phenotype is found in nature.

As used herein, the term "exposure of said cell" relative to a cellular factor or compound which may interact with a cell that comprises a regulatory promoter sequence of the invention refers to both external and internal exposure. In the case of exposure to a cellular factor, the factor may be native (endogenous) or exogenously provided.

II. Regulated Gene Expression using Promoters of the Invention

The promoter elements of the present invention find utility in the regulated expression of genes, both native and heterologous.

In order to accomplish such regulated gene expression the regulatory components of a promoter of interest must be identified and characterized.

This is accomplished by the combination of identifying and characterizing the sequence of promoter components involved in the control of gene transcription and correlating such structural (sequence) components with a functional analysis of gene expression using the promoter.

In general, to determine if a particular DNA sequence is involved in the regulation of gene expression, a putative regulatory sequence is selected and operably linked to a reporter sequence in a heterologous nucleic acid construct which is then introduced into a cell, then the reporter activity is determined. For example, the expression of luciferase, a gene originally isolated from the firefly that emits a photon in the presence of the substrate luciferin and ATP is easily monitored using a luminometer.

In one application of such regulated gene expression, compound binding sequences, located in the vicinity of the DNA response element for a transcriptional regulatory protein are incorporated into promoter constructs and used to regulate expression of a gene under the control of a given promoter. The compound binding sequences may be native or introduced.

In another exemplary embodiment, the binding of a compound in the vicinity of (i.e., directly, adjacent to, or overlapping) the DNA response element for a transcriptional regulatory protein provides a means to modulate transcription of a native gene operably linked to the DNA response element.

The identification and characterization of the regulatory regions of a promoter and using that information to design constructs which have one or more compound binding sequences in the vicinity of the DNA response element for a given transcriptional regulatory protein provides a means to regulate expression of native genes in vivo in a cell. In such cases, providing the compound to a cell and the binding of the compound to a compound binding sequence within the regulatory region of a promoter results in regulated expression of a native gene under the control of that promoter.

In another exemplary embodiment, the binding of a compound in the vicinity of (i.e., directly to, adjacent, or overlapping) the DNA response element for a transcriptional regulatory protein provides a means to modulate transcription of a transgene operably linked thereto. Any DNA binding compound that modulates the binding of a transcriptional regulatory protein to its DNA response element can be utilized to modulate expression of a transgene under the control of a promoter based on the present invention. The presence of a native or introduced compound-binding sequence in the vicinity of the DNA response element for a transcriptional regulatory protein permits a wide selection of compounds effective to regulate the expression of genes operably linked to a promoter wherein the promoter includes the DNA response element.

It will be understood that a promoter of the invention may include a minimal promoter element and an introduced DNA response element, or the promoter itself may contain a DNA response element. In general, the DNA response element or regulatory promoter sequence refers to the sequence to which transcriptional regulatory proteins bind and may or may not be considered part of the promoter.

In some cases, the nucleic acid sequence in the vicinity of the DNA response element will include a sequence that is the preferred or specific binding site for a DNA binding compound.

In other cases, the promoter sequence in the vicinity of the DNA response element will be modified to include one or more preferred binding sequences for a DNA-binding compound resulting in a regulatable promoter construct.

For example, the promoter may include one or more compound binding sequences in the vicinity of the DNA response element, as exemplified by an 8 to 20 or more bp "AT-rich" sequence which is a preferred binding preferred binding sequence for the netropsin dimer, "21x".

A transcriptional regulatory protein/DNA response element/compound binding sequence combination together with a compound which preferentially or specifically binds to that compound binding sequence may be useful for regulated expression of a transgene under the control of any of the promoters described herein. However, in some cases, the transcriptional regulatory protein/DNA response element/compound binding sequence combination and the compound which preferentially or specifically binds to that compound binding sequence is specific to a given promoter.

Compounds for use in regulating expression of a transgene under the control of a particular promoter are generally pre-selected based on the ability to regulate the expression of a transgene under the control of a given promoter.

Exemplary pre-screening assays include, but are not limited to, DNA binding assays; protein displacement assays; DNA footprinting, etc. As set forth herein, such assays may be carried out using various techniques known in the art.

In one embodiment, compounds for use in regulating gene expression are pre-selected for DNA-binding and transcriptional regulatory protein displacement. Exemplary pre-screening assays include various forms of the Merlin™ assay, e.g., co-owned U.S. Pat. Nos. 5,306,619, 5,693,463, 5,716,780, 5,726,014, 5,744,131, 5,738,990, 5,578,444, 5,869,241, expressly incorporated reference herein.

In another embodiment, compounds are pre-selected in a nucleic acid ligand interaction assay, such as that described in PCT Publication No. WO 00/15848 (expressly incorporated by reference herein), or another nucleic acid binding assay known to those of skill in the art.

III. Promoter Isolation and Characterization

The promoters described herein were isolated and characterized employing methods generally known in the art, including, but not limited to, walking upstream from the coding sequence of a known gene to identify regulatory sequences, analysis and characterization of previously identified promoter sequences by linker scanner mutation and site directed mutagenesis.

In some cases, promoter sequences are obtained by walking upstream in a PCR-accessible genomic library (e.g., using GenomeWalker, Clontech) using primers designed based on a known coding or other sequence. Sequential upstream walks are used to generate longer DNA sequences, extended at the 5' end in order to identify regulatory sequences. The sequence obtained from a first walk is used to design primers for a second upstream walk, etc.

In other cases, the full sequence of a particular promoter for which the regulatory sequences are described herein, was known in the art. However, in such cases the characterization of the promoter was not known prior to the present invention. In other words, the present invention represents identification and characterization of sequences critical to promoter activity.

In some cases, a series of promoters were constructed by introducing mutations in one or more regions of the promoter sequence followed by evaluation of the activity profile of the mutated promoters.

IV. Promoter Activity Screening

Exemplary assays for evaluation of promoter activity include, but are not limited to, DNA binding assays useful for detection of the binding of a transcriptional regulatory protein to the DNA response element of a promoter; protein displacement assays, such as gel mobility shift assays, competitive binding assays and DNA footprinting, etc. Such assays may be carried out using various techniques known in the art.

Gel mobility shift assays may be used to determine the effect of a compound on the binding of a transcriptional regulatory protein to the DNA response element within a given promoter, based on the change in size (and corresponding mobility on a gel) of the DNA/protein complex relative to the DNA alone.

DNA footprinting may be used to characterize the DNA response element of a given promoter for a transcriptional regulatory protein based on the stability of a promoter/transcriptional regulatory protein complex to nuclease degradation. The main application of this approach has been for DNA footprinting (a method used to identify the DNA sequence to which particular transcriptional regulatory proteins bind). Various techniques for DNA footprinting are known in the art.

Competitive Hybridization-stabilization Binding Assay (HSA)

The binding preference of compounds to critical sequences in the promoters of the invention has been examined using a competitive hybridization-stabilization binding assay (HSA). In the HSA, a nucleotide sequence of interest is represented in an oligonucleotide duplex, and the duplex is tested for its ability to compete with an indicator oligonucleotide duplex which is known to bind the test molecule with a certain degree of affinity. The indicators may be rich in AT bases and labeled with either a fluorescent probe or a quencher moiety on each of the two strands. The binding of the compound to the indicator stabilizes the duplex formation allowing the fluorescence to be quenched. If the compound prefers the test sequence (competitor) more than the indicator, it is less available to stabilize the indicator duplex and thus quenching is reduced. Therefore, a higher fluorescence signal implies a higher degree of binding preference to the test sequence relative to the indicator.

In one example involving the cyclin D1 promoter, the hybridization stabilization assay employs a 12 bp DNA duplex as an indicator for binding, wherein one strand of the duplex (CTTTATTATTTT, SEQ ID NO:81) is 5' labeled with fluorescein, and the complementary strand is 5' labeled with a dabsyl quenching molecule (AAAATAATAAAG-3', SEQ ID NO:82). When the two strands are mixed together with a DNA-binding molecule, which can stabilize the duplex form, the signal from the fluorescein is quenched by the dabsyl on the complementary strand. Various cold competitor duplexes can then be added to see whether they provide preferred binding sites for the DNA-binding compound. If the competitor DNA, binds the DNA-binding molecule, the DNA-binding molecule is titrated away from the indicator duplex resulting in destabilization of the indicator duplex and as the strands separate, quenching is diminished and fluorescence increases.

Promoter-walk analysis Typically, a full promoter sequence is presented in blocks of 15 nucleotides as the competitor in a HSA. To cover the entire promoter, stretches of 15-mers are blocked in an overlapping manner so that neighboring blocks differ by two nucleotides. An increase in fluorescence in the HSA implies a preference in binding.

RNase protection The effect of a modified DNA sequence on RNA transcription may be measured directly using an assay that includes either RNase protection or Northern analysis to monitor mRNA levels. RNase protection is a method of quantitating RNA based on its ability to form a nuclease resistant hybrid with a labeled probe. With more RNA, more probe can be protected. If only part of the probe hybridizes to the RNA of interest (i.e., the probe has 5' or 3' regions that are not homologous to the RNA of interest), then only part of the probe is protected. The protected probe and the intact probe will migrate at different rates when subjected to gel electrophoresis. Protection of a fragment of a unique and predictable size indicates specificity. The probe can be either an RNA or a DNA probe.

Linker Scanning Mutagenesis is a procedure in which short sequences of a DNA (i.e. sequences 5' to a known promoter) are substituted with DNA containing one or more restrictions sites, usually using a PCR based mutagenesis approach.

Reporter Constructs

A reporter construct is generally used in a cell-based in vitro assay to confirm promoter activity and the regulated expression of a transgene by a promoter.

In one embodiment, the luciferase reporter gene is used to evaluate regulatable gene expression in vitro in cell culture. However, any reporter gene known to those of skill in the art may also be used. It is preferable that expression of the selected reporter gene be readily detected and quantitated in order to quickly evaluate numerous modified regulatory sequences. Such reporter constructs provide a means to evaluate the ability to regulate gene expression by a given promoter, e.g., by targeting with a DNA-binding compound. Once the ability of a given promoter to regulate gene expression has been demonstrated in a cell-based assay using a reporter construct, the genetic construct may be readily modified to include a transgene of interest, such as a therapeutic gene, recombinant protein-encoding gene or drug resistance gene, in place of the reporter gene. Such modifications may be made using techniques routinely employed by those of skill in the art.

V. Cyclin D1 Promoter

Cyclin D1 (CCND1) is a regulatory protein overexpressed in many carcinomas. Cyclin D1 acts by binding to and regulating the cyclin dependent kinases CDK4 and CDK6. CCND1 gene expression is low in quiescent cells (in $G_0$) but is induced as cells respond to growth factors and enter the cell cycle leading to an increase in active cyclin D1-CDK4/CDK6 complexes.

Rapid cell cycling irrespective of appropriate growth signals and failure to respond to growth inhibition signals such as contact inhibition are characteristics of cancer cells. Inappropriate expression of cyclin D1 during chromosomal inversion, translocation or amplification has been characterized in a variety of tumor cells (Hall et al., 1996; Sherr, 1996). Cyclin D1 gene overexpression is also seen in many tumors without gross chromosomal rearrangements or amplification of the cyclin D1 gene. In fact, overexpression of cyclin D1 is seen in 50% of primary breast carcinomas, in 30% of adenocarcinomas of the colon cells (Hall et al., 1996), in familial adenomatous polyposis (Zhang et al., 1997) as well as in many cases of pancreatic cancer (Gansauge et al., 1997).

In addition, transgenic mice that overexpress the cyclin D1 gene in mammary epithelium show mammary hyperplasia and develop mammary adenocarcinomas (Wang et al., 1994). Overexpression of cyclin D1 in cultured cells results in early phosphorylation of pRB retinoblastoma protein (Sherr, 1993), shortening of the G1 phase and makes these cells growth factor independent (Jiang et al., 1993; Quelle et al., 1993; Resnitzky et al., 1994). When injected into nude mice these cells produce tumors (Jiang et al., 1993).

The link between inappropriate expression of cyclin D1 and tumorigenesis indicates that cyclin D1 is a good target for therapeutic intervention. Cyclin D1 antisense molecules have been shown to reduce the neoplastic phenotype of human esophageal, colon and pancreatic cancer cells overexpressing cyclin D1 in culture as well as the ability of these cells to produce tumors in mice (Zhou et al., 1995; Arber et al., 1997; Kornmann et al., 1998). In these studies antisense technology was used to specifically inhibit cyclin D1 mRNAs.

Accordingly, regulated expression of cyclin D1 finds utility in cancer and other therapies. The present invention is based on CCND1 promoter analysis and identification of DNA response elements within the cyclin D1 promoter that are involved in regulation of gene expression, when under the control of the cyclin D1 promoter.

The human CCND1 gene has been previously cloned and sequenced (Motokura et al., 1991; Withers et al., 1991; Xiong et al., 1991). An upstream promoter sequence of the CCND1 gene has also been cloned and sequenced (Herber et al., 1994a, 1994b; Philipp et al., 1994). The CCND1 promoter sequence may be found in GenBank at Locus HUMPRDA1A (Motokura et al., 1993).

Potential Sp1, E2F, CRE, Oct1, Myc/Max, AP-1, Egr, $NF_\kappa B$, STAT5, Ets, PRAD and TCF/LEF sites have been previously identified in the cyclin D1 promoter (Motokura et al., 1993; Herber et al., 1994; Philipp et al., 1994; Hinz et al., 1999; Matsumura et al., 1999; Shtutman et al., 1999; and Tetsu et al., 1999). Several of these sites have been demonstrated to play a role in cyclin D1 regulation in various cell lines (Philipp et al, 1994; Albanese et al., 1995; Watanabe et al., 1996; Yan, et al, 1997; Watanabe et al, 1998; Beier et al., 1999; Hinz et al., 1999; Matsumura et al., 1999; Shtutman et al., 1999; and Tetsu et al., 1999).

The CRE region of the CCND1 promoter (nucleotides −52 to −45) has previously been identified as important for cyclin D1 expression in various cell types (Beier et al., 1999; Tetsu et al., 1999; Phillip et al., 1994; Lee et al., 1999). In particular, the CRE promoter element has been demonstrated to be required for basal expression of the cyclin D1 gene in MCF7 cells.

Although the prior art includes some analysis of the cyclin D1 promoter, the prior art does not indicate appropriate targets for regulated gene expression using the cyclin D1 promoter. One aspect of the present invention is directed to modulating cyclin D1 expression in cancer cells that overexpress the gene, based on particular sequences identified as targets for regulation.

Analysis of transcription factor binding sites in the cyclin D1 promoter was carried out to identify portions of the cyclin D1 promoter that can be used to regulate the expression of a gene operably linked to the cyclin D1 promoter. An extensive promoter analysis was performed in a variety of different cancer cell lines that overexpress cyclin D1 and important transcription factor binding sites were identified, as detailed in Example 1.

A 1900-bp fragment of the human cyclin D1 promoter was PCR amplified from genomic DNA and subcloned into the vector pGL3-basic (Promega) to form a reporter construct. A series of modified promoters were made and promoter activities compared to that of the full-length (−1745) cyclin D1 promoter (FIG. 4) following transfection into asynchronous MCF7 human breast carcinoma cells, which overexpress cyclin D1, in order to identify important regulatory regions of the promoter. Some constructs were further evaluated in another cyclin D1 overexpressing breast carcinoma cell line (ZR75); in a breast cell line (HMEC) that expresses cyclin D1 normally; in a cyclin D1 overexpressing colon cancer cell line (HCT116); and an overexpressing pancreatic cancer cell line (PANC-1).

The various modified promoter constructs include 5′ deletions, site-directed mutagenesis of the AP1, CRE, E2F, SP1 and Oct1 sites, and mutants prepared using linker-scanning mutagenesis of the proximal promoter generated using the QuickChange mutagenesis system.

The results provided herein indicate that the regulatory sequences presented as SEQ ID NO: 5, SEQ ID NO:6, SEQ ID NO:8 and SEQ ID NO:9 find utility in regulating the expression of autologous or heterologous genes operably linked to a cyclin D1 promoter comprising one or more of the regulatory sequences.

VI. CD40 Ligand (CD40L)

CD40 ligand or CD40L (also referred to as gp39, CD154, TRAP or T-BAM) plays a critical role in T cell dependent humoral immune responses. CD40L interacts with CD40, which is expressed on the surface of antigen presenting cells (APCs; Ochs et al., 1994; Foy et al., 1996; Grewal et al., 1996). Antigen presenting cells process antigens and present them on their surface in combination with major histocompatability complex (MHC) molecules. This provides one signal necessary for T cell activation and recognition of an antigen-MHC complex by the T cell receptor which triggers the transient expression of the membrane bound cytokine CD40L on activated CD4+ helper T cells. Interaction between CD40 and CD40L is necessary for B cell activation and isotype switching. The binding of CD40L to CD40 induces the expression of the costimulatory molecules B7.1 (CD80) and B7.2 (CD86) on APCs which in turn, bind to CD28 on T cells providing the second costimulatory signal necessary for T cell activation. Engagement of the T cell receptor by antigen-MHC in the absence of the second signal produces T cell anergy. A human genetic defect in the CD40L gene causes the X-linked immunodeficiency disorder called hyper-IgM syndrome (Allen et al., 1993; Aruffo et al., 1993; DiSanto et al., 1993; Korthauer et al., 1993). Affected individuals either fail to express CD40L or express CD40L incapable of binding to CD40 resulting in significantly reduced T cell-dependent humoral immune responses and an absence of isotype class switching.

Targeting the CD40L promoter therefore has implications to a number of autoimmune disorders, including but not limited to, multiple sclerosis (MS), systemic lupus erythematosus (SLE), graft-vs-host disease (GVHD) and rheumatoid arthritis. (See, e.g., Buhlmann et al., 1996; Biancone et al., 1999). In addition, there is evidence that inhibiting CD40L expression can contribute to long term transplantation tolerance (Larsen et al., 1996; Kirk et al., 1997; Hancock et al., 1998; Niimi et al., 1998). Further, targeting CD40L with specific monoclonal antibodies has been shown to increase the effectiveness of adenovirus vector based gene therapy (Yang et al., 1996; Kay et al., 1997).

The human CD40L gene has been cloned (Graf et al., 1992; Hollenbaugh et al., 1992; Spriggs et al., 1992; Gauchat et al., 1993; Shimadzu et al., 1995). The CD40L promoter sequence contains several potential transcription factor binding sites: AP-1 (1570 to 1577; 1867 to 1938), GMCSF (1040 to 0145; 1343 to 1350; 1689 to 1696; 1840 to 1862), α IRE (1291 to 1295; 1359 to 1366; 1397 to 1404; 1589 to 1593; 1701 to 1705; and 1803 to 1807), TCF1 (1603 to 1606; 1731 to 136), GATA-1 (1643 to 1647), CRE 2(1209 to 1216), γ INF2 (1188 to 1195), NF-IL6 (815 to 819) and $NF_\kappa B$ (737–743) as identified by sequence analysis (GenBank Accession No. D31793).

In order to characterize the CD40L promoter, the full-length human CD40L promoter from −1860 to +49 (SEQ ID NO:1) was PCR amplified and cloned into the firefly luciferase reporter plasmid pGL3-basic, as detailed in Example 2. A series of 5' CD40L promoter deletions and specific mutations were prepared, PCR amplified and cloned into the firefly luciferase reporter plasmid pGL3-basic, the authenticity of all clones verified by DNA sequencing and promoter activity of the 5' deletion constructs compared to that of the full-length (−1860) CD40L promoter following transfection into normal expanded T cells and activation with PMA and ionomycin (Example 2).

The results indicate that at least four regions of the CD40L promoter are critical to expression in activated T cells, including a site near nucleotide position −306, the specific mutation of which resulted in a 4-fold down regulation of CD40L promoter activity factor binding at the site. (See Example 2)

A second promoter region that plays a role in controlling CD40L expression is the sequence between nucleotides −230 and −211 (SEQ ID NO:13), based on deletion of the region which resulted in a 6.7-fold reduction in promoter activity.

A third region important to CD40L promoter expression in activated normal human T cells is found between −230 and −196 (SEQ ID NO:14), based on deletion of the −230 to −211 region, which resulted in an 6.7-fold downregulation of CD40L promoter activity, and site specific mutations of −220 to −215, −214 to −209, −208 to −203 or −202 to −197, which resulted in a 2.5 to 4-fold down regulation of promoter activity. A T cell-specific, sequence-specific factor was demonstrated to bind in the −206 to −201 region based on the results of in vivo footprinting analysis.

A fourth region identified in the CD40L promoter as important for expression in activated normal human T cells is found between −77 and −40 (SEQ ID NO:15) based on the expression level of deletion mutants, wherein an internal deletion of −72 to −49 or −61 to −40 resulted in a 25-fold or 40-fold downregulation respectively. In addition, specific mutations in the composite AP-1/-66 NF-AT site together with a previously unidentified site located between −48 and −54 indicates a contribution to transcriptional activation through the −48 to −54 site.

It will be appreciated that some CD40L promoter regions may bind more than one transcription factor, as further discussed in Example 2. It will further be appreciated that targeting a DNA-binding compound to a regulatory region of the CD40L promoter described herein, provides a means to inhibit CD40L promoter-mediated transcription through modulation of transcription factor-DNA interactions.

The results provided herein indicate that the regulatory sequences presented as SEQ ID NO:12, SEQ ID NO:13, SEQ ID NO:14 and SEQ ID NO:15 find utility in regulating the expression of autologous or heterologous genes operably linked to a CD40L promoter comprising one or more of the regulatory sequences.

VII. Hepatitis B (HBV)

Viral induced Hepatitis B in humans is caused by infection with HBV, which is estimated to have infected 300 million people worldwide. A small but significant portion of the infected individuals develop severe pathologic consequences, including chronic hepatic insufficiency, cirrhosis, and hepatocellular carcinoma, with one million deaths per year caused by HBV infection worldwide.

Vaccination is an effective preventive measure, however, there is no cure for the disease, and at present there is no effective treatment specific to acute hepatitis B. Currently, chronic hepatitis B is treated with interferons (i.e., interferon-alpha) and nucleoside analogs (i.e., lamivudine "3TC").

HBV was initially cloned in the 1970s (Robinson et al., 1974; Sattler et al., 1979; Summers et al., 1975). Human hepatoma cell lines (HepG2 and HuH6) have HBV stably integrated within the cellular genome. These cells can support HBV replication and release virus-like particles into the tissue culture media. See, e.g., See MA et al., 1987; Lander et al., 1997; Sudo et al., 1996.

HBV is a DNA virus which has a genome consisting of a relaxed, circular, partially duplex DNA species of 3.2 kb. Every nucleotide in the genome is within a coding region, and over half of the sequence is translated in more than one opening reading frame. Several promoters have been identified, driving expression of (a) pre-core proteins, core proteins and polymerase (core promoter); (b) large S surface protein (pre-S1 promoter); (c) medium and small S surface proteins (S promoter); and (d) X protein (X promoter). The core protein encapsulates the viral genome and polymerase, the various S surface proteins make up the protein coat, and the function of the X protein has not been determined.

Characterization of the core promoter, which directs the transcription of two greater than genome size messenger transcripts, has been described (for reviews, see Ganem D., in FIELD VIROLOGY $3^{rd}$ Ed. 1996 and Kann M. and Gerlich W., in Viral Hepatitis, $2^{nd}$ Ed). One of these mRNAs, the pregenomic transcript encodes both the core structural protein and the viral polymerase as well as template for replication of the negative strand viral DNA. The other 3.5 kb mRNA, the pre-core message, is translated and modified into the soluble viral e antigen. Binding sites for hepatocyte nuclear factors, C/EBP, and Sp1 have previously been described in the core promoter region (as reviewed in Ganem D., in FIELD VIROLOGY, $3^{rd}$ Ed. 1996 and Kann M. and Gerlich W., in VIRAL HEPATITIS, $2^{nd}$ Ed). The hepatocyte nuclear factors, HNF3 and HNF4, are believed to be important for the liver tropism of HBV. Additional transcription factor binding sites such as C/EBP and Sp1 have been described.

A characterization of three HBV promoters is provided herein; a core promoter (SEQ ID NO:16, FIG. 1A), a pre-S1 promoter (SEQ ID NO:22, FIG. 1B), and the HBV-X promoter (SEQ ID NO:25, FIG. 3).

The HBV promoters described herein find utility in regulated gene expression which is specific to liver cells.

Analysis of the effect of modification of various sequence components of the HBV core, preS1 and X promoters was carried out to identify portions of the promoters that can be used to regulate the expression of a gene operably linked to the HBV core, preS1 or X promoter, respectively, as detailed in Example 3.

Luciferase reporter activities of wild type core, X, and preS1 promoter constructs and various modifications thereof were evaluated by transient transfection experiments in cell lines of hepatic origin such as HepG2, Huh7, 22.1.5, and HepAD38.

HBV Core Promoter

Three regions of interest were identified in the linker scanning analysis of the HBV core promoter. The TATA box, HNF4 (SEQ ID NO:18) and proximal HNF3 (SEQ ID NO:17) sites were identified as the control elements most critical to core promoter activity. As further described in Example 3, three regions of the HBV core promoter, domain 5; domain 8/9 and domain 13 appear to be in the vicinity of cis-elements (HNF-4/HNF-3, HNF-3/Sp1, and the TATA box, respectively) reported in the literature. The results of expression studies presented in Table 9 suggest that domain 8 (SEQ ID NO: 19); domain 8/9-1 (SEQ ID NO:20); and domain 13 (SEQ ID NO: 21) are involved in transcriptional activation and that those sequences find utility in regulating the expression of autologous or heterologous genes operably linked to an HBV core promoter comprising SEQ ID NO:20 and/or SEQ ID NO:21.

preS1 Promoter

A luciferase reporter construct was generated using a full-length copy of the HBV genome with the preS1 promoter positioned immediately upstream of the luciferase reporter gene and site-directed mutagenesis was performed to generate four mutants in known transcription factor binding sites and linker scanner mutants. The mutagenized constructs were transiently transfected into Hep3AD38 and tested for promoter activity, as described above. As detailed in Example 3, a known transcription factor binding site, designated HNF1 was found to be critical to preS1 promoter activity.

The results provided herein indicate that the regulatory sequences presented as SEQ ID NO: 23 and SEQ ID NO:24 find utility in regulating the expression of autologous or heterologous genes operably linked to an HBV preS1 promoter comprising one or both of the regulatory sequences.

HBV X Promoter

The HBV X promoter was analyzed by deletion and linker scanning experiments similar to those described for the core promoter.

A luciferase reporter construct was constructed with a full-length copy of the HBV genome and the HBV X promoter positioned immediately upstream of a reporter coding sequence. Promoter constructs were prepared with successive blocks of 21 base pair mutations in the HBV X promoter or known transcription factor binding sites. Mutant constructs were transfected into the hepatoma-derived HepG2 and HepG2 cell lines stably transfected with HBV: 22.1.5 and HepAD38, and the expression of the luciferase reporter gene analyzed to determine HBV promoter activity, as detailed in Example 3. Mutations in domains 3, 4 and 6 as well as double mutants (domains 3+6 and domains 4+6), yielded the greatest reduction in activity. Additional HBV-X promoter reporter constructs were made with mutations in various known transcription factor binding sites and evaluated for luciferase reporter activity suggesting that domains 18 and 19 are also important for activity of the HBV X promoter.

The results provided herein indicate that the regulatory sequences presented as SEQ ID NO: 26, SEQ ID NO:27 and SEQ ID NO:28 find utility in regulating the expression of autologous or heterologous genes operably linked to an HBV X promoter comprising one or more of the regulatory sequences.

VIII. Vancomycin-Resistant Enterococci (VRE)

Recently, a rapid increase in the incidence of infection and colonization with vancomycin-resistant enterococci (VRE) has been reported. The observed resistance is of concern due to (1) the lack of effective antimicrobial therapy for VRE infections because most VRE are also resistant to drugs previously used to treat such infections, i.e., penicillin and aminoglycosides (CDC, 1993; Handwerger et al., 1993); and (2) the possibility that the vancomycin-resistant genes present in VRE can be transferred to other gram-positive microorganisms.

Although enterococci can be part of the normal flora of the gastrointestinal and female urogenital tracts, recent studies indicate that enterococci can be transmitted directly in the hospital setting. (See, e.g., Boyce, et al., 1994.) Enterococci have been recognized as a cause of nosocomial infection and some strains are resistant to multiple antimicrobial drugs. The most common enterococci-associated nosocomial infections are urinary tract infections, post-surgical infections and bacteremia (Murray, 1990; Moellering R C Jr., 1992; Schaberg et al., 1991).

Vancomycin has been used extensively to treat Enterococcus infection since the late 1970s. Recently, a rapid increase in the incidence of infection and colonization with vancomycin-resistant enterococci (VRE) has been reported.

Resistance to vancomycin and other glycopeptide antibiotics has been associated with the synthesis of a modified cell-wall precursor, terminating in D-lactate which has a lower affinity for antibiotics such as vancomycin.

Typically gram positive bacterial cell wall synthesis involves assembly, membrane transport, incorporation into the cell wall and cross linking of a pentapeptide precursor molecule as part of the process of peptidoglycan formation. Vancomycin functions by forming a complex with the peptidyl-D-ala-D-ala precursor, thereby inhibiting precursor transport by transglycosylases and incorporation into the peptidoglycan, and weakening the bacterial cell wall. Type A high-level vancomycin resistance is achieved via an operon that replaces the C-terminal D-ala with D-lac, such that vancomycin binding is inhibited (Walsh C, 1999).

The operon is controlled by a two component regulatory system that consists of a sensor protein, VanS and a cytoplasmic response regulator, VanR.

VanS is a two domain transmembrane signaling kinase which undergoes an autophosphorylation at histidine residue (H164). Phospho-VanS in the presence of ATP can undergo phosphotransfer to an aspartate residue on VanR (2). Studies have shown that phospho-VanR binds with high efficiency to $P_{vanH}$ and enhances transcription of the genes necessary for vancomycin resistance (Haldimann et al., 1997; Holman et al., 1994).

The polysystronic message that gives rise to the genes necessary for high level inducible vancomycin and teichoplanin resistance consists of vanH, A, X, Y and Z. The vancomycin resistance enzyme VanH is an alpha-ketoacid dehydrogenase that stereospecifically reduces pyruvate to D-lactate, which forms an integral part of the bacterial cell wall replacing the vancomycin target dipeptide D-alanine-D-alanine (Stoll et al., 1998; Marshall et al., 1999).

The present invention hypothesizes that a DNA binding molecule properly placed within the vanH promoter will displace phospho-VanR and shut down transcription of inducible resistance genes, thus rendering the bacteria once again sensitive to vancomycin. Although the mechanism is not part of the invention, shutting down transcription of the resistance genes is preferable to shutting down the two component regulatory system due to potential cross talk between $P_{vanH}$ and the response regulators of other two component regulatory systems (Silva et al., 1998).

It follows that regulating the expression of the vanH promoter has application to treatment of infectious disease.

DNA sequencing of the vanH promoter region from nine A type strains of VRE showed a high degree of sequence identity with the published A type regulatory region (GenBank Accession N. M97297). A modified pAM401 plasmid (ATCC) was designed containing a VRE promoter sequence upstream of the luciferase gene in a background allowing for growth and maintenance in *E. coli* and Enterococcus species. (See Example 4.)

Site directed mutagenesis of the VRE promoter region was carried out by systematically altering short 8 to 10 bp regions of the consensus promoter sequence, including the −35 consensus binding site within the phosphorylated VanR footprint (Arthur et al., 1992). In addition, 20 linker scanning mutants designated M2–M21 were generated and nucleic acid constructs containing the VRE promoter sequence upstream of the luciferase gene were subcloned into the a pRLUC parent vector and transformed into *E. coli.*

Each linker scanner promoter mutant was tested for activity, with both up- and down-regulation observed. The largest decrease was to 0% of wild type activity and the largest increase was 1737% of wild type activity. All mutants in the region reported to be footprinted by phosphorylated VanR (M2–M8) showed decreased activity. Increased activity was observed in mutants spanning −30 to +20, suggesting the possibility of a repressor binding site in this region. Mutants M8 and M9 were shown to consistently result in the highest luciferase activity of the mutants tested (Example 4).

The results provided herein indicate that the regulatory sequences presented as SEQ ID NO: 32, SEQ ID NO:33 and SEQ ID NO:34 find utility in regulating the expression of autologous or heterologous genes operably linked to a VRE promoter comprising one or more of the regulatory sequences.

IX. Androgen Receptor

Prostate cancer is the most frequently diagnosed cancer in males in the United States. The cancer is treatable if diagnosed early, however, once the cancer metastasizes virtually all patients die within 12–18 months. Current treatments for metastatic prostate cancer involve targeting the androgen receptor (AR) using surgical or chemical means. The androgen receptor (AR) directly regulates gene expression when bound to androgens such as testosterone or dihydrotesosterone (DHT) and is required for prostate maintenance. Once androgens are removed, genes regulated by the AR in the prostate are turned on or off resulting in programmed cell death or apoptosis.

The androgen receptor promoter from nucleotides −6000 to +1100 was cloned from genomic DNA by PCR using GenBank sequences for primer design. The amplified promoter sequence was subcloned into pGL3 basic (Promega) for subsequent transient transfection and evaluation of luciferase expression. A large series of deletion constructs were made and tested following transient transfection, as detailed in Example 5.

The results of luciferase expression assays in the AR+ cell line, LNCaP, following transient transfection of various deletion constructs indicate the presence of a repressor binding site between nucleotides −2000 and −200 and multiple activator sites at nucleotides −150 to −100 (homopurine stretch), −100 to −50 (SP1 site), and −50 to +1 (helix loop helix binding site).

More specifically, the results suggest that: (1) the 5' region of the homopurine region represents all of the activity from −150 to −100; (2) the region 3' of the downstream helix-loop-helix sequence contains another 2-fold of activity; and (3) the downstream helix-turn-helix site contains 1.5-fold activity.

The present invention represents the identification of regulatory sequences of the AR promoter, examples of which are presented as SEQ ID NO: 64, SEQ ID NO:65 and SEQ ID NO:66, respectively. The regulatory sequences presented as SEQ ID NO: 64, SEQ ID NO:65 and SEQ ID NO:66 find utility in regulating the expression of autologous or heterologous genes operably linked to an AR promoter comprising one or more of the regulatory sequences.

X. Her2

Her2 (human epidermal growth factor receptor2; c-erbB2, neu) is a tyrosine kinase growth factor receptor implicated in the metastatic growth of a subclass of breast cancers. Her2 overexpression occurs in up to 30% of patients with breast cancer and is associated with an especially aggressive form of the disease characterized by more rapid disease progression and shortened survival. Her2 can be overexpressed in breast cancer cells, ovarian cancer cells as well as a variety of other cancer cells. Accordingly, regulated expression of Her-2 would be useful to modulating such overexpression.

A 2000-bp fragment of the human Her2 promoter was PCR amplified from genomic DNA using the following oligonucleotides. This purified fragment was subcloned into the vector pGL3-basic (Promega) at the NcoI and HindIII sites for use in transient transfection luciferase expression assays in the breast carcinoma cell lines MCF-7 (low Her2 expression) and 2R75-1 (high Her2 expression).

The results of studies detailed in Example 6 indicate that the critical regulatory sites for the Her2 promoter lie between nucleotides −125 and −50. More specifically, sequences of interest for regulated expression of Her2 are a repressor sequence (SEQ ID NO:70) downstream of the putative TATA box from −23 to −19; a complex regulatory region (SEQ ID NO:71) which includes both an activator and a repressor component; and a putative TATA box/ets site (SEQ ID NO:72).

The regulatory sequences presented herein as SEQ ID NO:70, SEQ ID NO:71 and SEQ ID NO:72 find utility in regulating the expression of autologous or heterologous genes operably linked to a Her2 promoter comprising one or more of the regulatory sequences.

XI. Beta-lactamase (Bla) Promoter

The extensive use of beta-lactam antibiotics has resulted in significant bacterial resistance to such treatment. This resistance is generally mediated by lactamases in both gram-positive and gram-negative bacteria. More specifically, the beta-lactamase gene confers ampicillin resistance to a number of types of bacteria including *E coli*. Recently, therapeutic approaches directed to overcoming such antibiotic resistance have been developed which include the delivery of a beta-lactam antibiotic in combination with a beta-lactamase inhibitor.

Regulated expression of the beta lactamase gene provides another means to modify such antibiotic resistance. In order to determine which regions of the beta lactamase gene may be used to regulate beta lactamase expression, luciferase reporter constructs were prepared containing a beta-lactamase promoter sequence upstream of the luciferase gene.

Promoter mutants of the natural beta lactamase P3 bla promoter were generated by systematically altering the base pairs of the entire bla promoter sequence (from nucleotides −101 to +43).

Luciferase activities were measured in lysates prepared from *E. coli* XL1 Blue replicates. Mutants which exhibited significantly decreased luciferase activity included those with mutations in the −35 region (−41 to −30, M6); the −10 region (−17 to −6, M8); the start site (−5 to +7, M9); and +20 to +31 (M11). The luciferase activities of these constructs were reduced to 24%, 29%, 15% and 2% of wild type, respectively, as further described in Example 7.

Bla promoter linker scanner mutant constructs were generated by introducing 6 or 12 base pair mutations at different locations of entire bla promoter. Renilla luciferase reporter activities of the mutants measured and compared to the activity of the wild type pBla-Renilla luciferase construct.

The regulatory sequences presented herein as SEQ ID NO:77 and SEQ ID NO:78 find utility in regulating the expression of autologous or heterologous genes operably linked to a beta lactamase (bla) promoter comprising one or more of the regulatory sequences.

XII. Utility/Applications

The present invention is directed to isolation of various promoters, characterization of the promoters, and in particular characterization of regulatory elements of the promoters. The promoters described herein find utility in regulated gene expression and may function by interaction with natural cellular factors (e.g., transcriptional regulatory proteins) or by interaction with exogenously provided cellular factors or compounds.

The promoter may be a minimal or full length promoter. It will be understood that the promoter sequences described herein include minimal promoter elements alone or together with control sequences (also termed "transcriptional and translational regulatory sequences"), involved in expression of a given gene product. In general, transcriptional and translational regulatory sequences include, but are not limited to, the promoter sequence itself, the DNA response element for a transcriptional regulatory protein, ribosomal binding sites, transcriptional start and stop sequences, translational start and stop sequences, and enhancer or activator sequences.

The binding of a transcriptional regulatory protein to its corresponding DNA response element serves to regulate the expression of a gene under the control of a promoter operably linked to the promoter. Identification of sequences critical to such binding and regulation provides a framework for controlling the transcription and therefore the expression of a gene under the control of the promoter.

Accordingly, the promoter regulatory sequences described herein may be used to regulate the expression of genes operably linked to the relevant promoter. Such promoter regulatory sequences find utility in the design and construction of heterologous nucleic acid constructs and in the regulated expression of native genes.

The promoter regulatory sequences described herein may also be used in conjunction with a DNA binding compound to regulate the expression of a gene operably linked to the promoter.

In some cases, a given promoter may be regulated by a native factor, for example, the expression of a gene operably linked to a cell type-specific, developmentally regulated, or disease-specific promoter which promotes gene expression in certain tissues without affecting expression in other tissues may be regulated using the sequences described herein.

More specifically, the ability to regulate the expression of genes under the control of a cyclin D1 promoter has application to treatment of various cancers, including, but not limited to, breast cancers, colon cancers and pancreatic cancers.

Interaction between CD40 and CD40L is necessary for B cell activation and isotype switching. Therefore, regulation of the activity of the CD40L gene promoter finds utility in the treatment of various immunological disorders, such as autoimmune disease.

Regulated expression of genes under the control of the HBV-specific core, pre-S and X promoters find utility in the therapy of HBV disease and in the regulated expression of liver cell-specific genes.

Resistance to the antibiotic, vancomycin, which is used to treat Enterococcus infection has been associated with the vancomycin resistance enzyme VanH. Therefore, regulated expression of the vanH gene promoter has utility in treatment of Enterococcus infection.

Given that the androgen receptor (AR) is currently the target of numerous therapeutic strategies for treatment of prostate cancer, regulated expression of the androgen receptor gene promoter finds utility in the treatment of prostate cancer.

Her2 is a tyrosine kinase growth factor receptor implicated in the metastatic growth of a subclass of breast cancers as well as various other types of cancers. Therefore, regulated expression of the Her2 gene promoter has utility to treatment of cancer.

The β-lactamase gene confers ampicillin resistance to *E. coli*. Accordingly, regulated expression of the β-lactamase gene promoter is relevant to modulation of such antibiotic resistance.

The sequence information and functional characterization of the promoter regulatory sequences described herein can therefore be used to regulate the transcription of endogenous genes and transgenes (autologous and heterologous genes, respectively), in a variety of useful applications.

All patent and literature references cited in the present specification are hereby expressly incorporated by reference in their entirety.

While the invention has been described with reference to specific methods and embodiments, it will be appreciated that various modifications and changes may be made without departing from the invention.

Material and Methods

Luciferase Assays Cells were washed once with PBS buffer, harvested in 1 ml PBS, pelleted, and lysed with 100 µl passive lysis buffer (Promega) at room temperature for 15–20 minutes. The cell lysates were centrifuged for 5 minutes, then 10 µl of lysate is added to 100 ml of luciferase assay reagent (Promega). Assays were carried out in a luminometer (EG&G Berthold). Luciferase activity is expressed as a rate of light units. Correction for transfection efficiency and variations in harvesting were done by cotransfecting an SV40 renilla-luciferase reporter gene (PRL-SV40) or a promoterless renilla-luciferase gene (PRL-Null) and determining the activity of the renilla luciferase internal control in the same Dual Luciferase assay (Promega). After standardization with renilla luciferase activity, a relative luciferase activity was obtained, and the mean and standard deviation from triplicate wells were calculated. In general, transfections were repeated and reproduced in at least two independent experiments.

EXAMPLE 1

Cyclin D1 Promoter Analysis

The full-length human cyclin D1 promoter from −1745 to +155 (FIG. 4, SEQ ID NO:1) was PCR amplified and cloned into the firefly luciferase reporter plasmid pGL3 basic. A series of cyclin D1 5' promoter deletions were similarly constructed and cloned into pGL3-basic. Mutant promoter constructs were assayed in MCF7 cells, a second cyclin D1 overexpressing breast carcinoma cell line, ZR75; a breast cell line that expresses cyclin D1 normally, HMEC; a cyclin D1 overexpressing colon cancer cell line, HCT116; and a cyclin D1 overexpressing pancreatic cancer cell line, PANC-1.

Construction of Plasmids

A 1900-bp fragment of the human cyclin D1 promoter was PCR amplified from genomic DNA using the following oligonucleotides: 5'-GCA CGC GTG CTA GCC AGC TGG GCC CTT GT 3' (SEQ ID NO:2) and 5'-ATC CAT GGA AGC TTT GGG GCT CTT CCT GGG CA-3' (SEQ ID NO:3). This purified fragment (SEQ ID NO:1), representing nucleotides −1745 to +155 relative to the transcription start site of the cyclin D1 promoter, was subcloned into the vector pGL3-basic (Promega) at the MluI and HindIII sites to form the reporter −1745D1/LUC. A series of 5' deletions were cloned using polymerase chain reaction of the native promoter plasmid as follows: a 5' deletion to −1590, a 5' deletion to −1440, a 5' deletion to −690, a 5' deletion to −545, a 5' deletion to −390, a 5' deletion to −245, and a 5' deletion to −90, using the PCR primer having the sequence presented as 5'-GCA CGC GTG CTA GCT GGA GCC TCC AGA GGG CTG T-3' (SEQ ID NO:4).

Promoter activities for the 5' deletion constructs were compared to that of the full-length (−1745) cyclin D1 promoter following transfection into asynchronous MCF7 human breast carcinoma cells, which overexpress cyclin D1. Deletion of cyclin D1 promoter regions between −1745 and −245, in the context of the full length promoter (−1745) had little effect on basal promoter activity in MCF7 cells.

Site-directed mutagenesis of the AP1, CRE, E2F, SP1 and Oct1 sites, and linker-scanning mutagenesis of the proximal promoter were generated using the QuickChange mutagenesis system and the parent—1745D1/LUC plasmid. Restriction enzyme analysis and DNA sequencing confirmed the integrity of these constructs.

Mutation of the E2F site {Motokura & Arnold, 1993}resulted in a construct which retained 63% of wild-type activity. Mutation of the CRE element resulted in a construct that retained 32% of wild-type activity, indicating that it is important to basal cyclin D1 expression in MCF7 cells.

```
 -60                           -37       (SEQ ID NO:83)
AACAACAGTAACGTCACACGGACT

TTGTTGTCATTGCAGTGTGCCTGA
         CRE
```

In addition to MCF7 cells, mutant promoter constructs were assayed in another cyclin D1 overexpressing breast carcinoma cell line, ZR75; in a breast cell line that expresses cyclin D1 normally, HMEC; in a cyclin D1 overexpressing colon cancer cell line, HCT116; and an overexpressing pancreatic cancer cell line, PANC-1. The −1745 wild-type, the −10 deletion or various site-directed mutants of the cyclin D1 promoter were inserted into the promoter-less firefly luciferase plasmid (pGL3-basic) and co-transfected into various cells together with an SV40 promoter driven Renilla luciferase control plasmid. Firefly luciferase activity for each construct was normalized to Renilla luciferase activity and is shown relative to that of the full-length wild-type promoter (−1745).

Tissue Culture

The human breast carcinoma cell lines MCF7 and ZR75 were maintained in DMEM/F12 medium with 10% fetal bovine serum, 10 µg/ml bovine insulin and antibiotics (penicillin/streptomycin). The human colon carcinoma cell line HCT116 was maintained in McCoy's medium with 10% fetal bovine serum and pen/strep. The human pancreatic cell line PANC-1 was maintained in DMEM/F12 with 10% fetal bovine serum and pen/strep. Human mammary epithelial cells (HMEC) were maintained in Epithelial Growth Media supplemented with bovine pituitary extract (50 µg/ml), hydrocortisone (500 ng/ml), hEGF (10 ng/ml), and insulin (5 µg/ml). All lines were maintained at 37° C., 5% $CO_2$. MCF7, ZR75, HCT116 and PANC-1 cells were purchased from the American Type Culture Collection. HMEC cells were purchased from Clonetics Corp.

Transient Transfections

Cells were transiently transfected with LipofectAMINE (GIBCO Life Sciences) in triplicate in 6-well tissue culture plates (Corning, N.Y.). Equal numbers of cells ($3\times10^5$/well) were seeded in each well 24 hours prior to transfection. Prior to transfection, cells were equilibrated in 800 µl fresh medium (OptiMEM with 5% FBS and pen/strep). Cells were transfected with 5 µg of reporter plasmid containing various different cyclin D1 promoter constructs in 200 µl transfection buffer. After 4 hours incubation with the transfection solution, cells were fed with 4 ml OptiMEM with 5% FBS and pen/strep. Cells were harvested 48 hours after transfection.

ing cancer cell lines tested, as well as in HMEC cells which express normal levels of cyclin D1. The effects of mutations in various other regions of the cyclin D1 promoter are summarized in Table 2, below.

TABLE 1

Reporter Activity of Cyclin D1 Promoter Constructs

| Promoter construct | MCF7 cells (% wild-type) | HCT116 cells (% wild-type) | ZR75 cells (% wild-type) | PANC-1 cells (% wild-type) | HMEC cells (% wild-type) |
|---|---|---|---|---|---|
| −1745,(wild-type) | 100 | 100 | 100 | 100 | 100 |
| −10 | 11 ± 0.7 | 22 ± 1.6 | 21 ± 1.1 | 45 ± 1.9 | 50 ± 4.8 |
| CREbam | 32 ± 1.7 | 46 ± 3.3 | 64 ± 6.8 | 52 ± 7.5 | 50 ± 2.1 |
| 3′ CREm | 102 ± 7.1 | 86 ± 8.8 | 92 ± 6.4 | 89 ± 4.3 | 74 ± 2.1 |
| 5′ CREm | 160 ± 3.6 | 120 ± 15.6 | N/D | 99 ± 6.3 | N/D |
| CRE4C5G | 33 ± 5.0 | 69 ± 5.1 | 54 ± 8.3 | 52 ± 4.9 | N/D |
| −30- to 21 | 33 ± 2.2 | 91 ± 12.2 | 77 ± 7.0 | 46 ± 4.8 | 78 ± 4.8 |
| +1 to +9 | 37 ± 4.0 | 46 ± 4.1 | 92 ± 12.5 | 53 ± 8.3 | 74 ± 5.0 |
| cRE4C/−30 to −2 | 11 ± 1.3 | 30 ± 4.5 | 38 ± 11.4 | 40 ± 6.9 | 26 ± 1.7 |
| cRE4C/+1 to +9 | 14 ± 0.8 | 32 ± 4.2 | 43 ± 4.0 | 17 ± 3.4 | N/D |

Analysis of Cyclin D1 Promoter Elements

Tables 1 and 2, below, show a summary of the results of deletion analysis studies of the cyclin D1 promoter in MCF7 cells. Various 5′ deletions or site-directed mutations of the cyclin D1 promoter were inserted into the promoterless firefly luciferase plasmid (pGL3-basic) and co-transfected into MCF7 cells human breast carcinoma cells, which overexpress cyclin D1 (Buckley, 1993), together with an SV40 promoter driven Renilla luciferase control plasmid. The length of each construct is indicated relative to the transcriptional start site (+1). Firefly luciferase activity for each construct was normalized to Renilla luciferase activity and is shown relative to that of the full-length wild-type promoter (−1745). The data are presented as the mean+/−SEM with a minimum of two independent transfections done in triplicate. Deletion of cyclin D1 promoter regions between −1745 and −245, in the context of the full length promoter (−1745), had little effect on basal promoter activity in MCF7 cells, even though several potential transcription factor binding sites have been previously identified in that region.

Cyclin D1 promoter constructs containing a mutation of the CRE in combination with a mutation of the −30 to −21 region resulting in severely compromised promoter activity in all of the cell lines tested. In vivo footprinting experiments carried out as described below demonstrate factor binding at both the CRE and the −30 sites in HCT116 cells.

In all cell lines tested, mutation of the CRE in constructs designated as CREbam and CRE4C5G reduced basal promoter activity considerably although the strongest effect was seen in MCF7 cells. The corresponding wild type sequence is presented as SEQ ID NO:7.

Mutation of the −30 to −21 site reduced basal cyclin D1 promoter activity in some cell lines, but not others. However, in all cell lines tested, mutation of the −30 to −21 site in combination with mutation of the CRE (construct CRE4C/−30-21) reduced basal promoter activity considerably and to a greater extent than did mutation of either site alone (Table 1). This suggests that both the CRE and the −30 to −21 sites are involved in transcriptional regulation of basal cyclin D1 promoter activity in all of the overexpress-

TABLE 2

Reporter Activity of Cyclin D1 Promoter Constructs

| 5′ deletion | % WT activity |
|---|---|
| −1590 | 92 ± 0 |
| −1440 | 96 ± 13.1 |
| −690 | 79 ± 3.5 |
| −545 | 82 ± 2.4 |
| −390 | 81 ± 7.1 |
| −310 | 89 ± 4.4 |
| −245 | 78 ± 7.6 |
| −90 | 39 ± 1.2 |
| −10 | 11 ± 0.7 |

Site-directed mutagenesis of the AP1, CRE, E2F, SP1 and Oct1 sites, and linker-scanning mutagenesis of the proximal promoter was carried out to determine the effect on promoter activity. The results indicate that mutation of the E2F site (Motokura et al., 1993) resulted in a moderate decrease in activity, while mutation of the CRE element indicated that it is important to basal cyclin D1 expression in MCF7 cells.

A thorough analysis of the CCND1 promoter indicate that the CRE site at −52 is a critical site for cyclin D1 expression in HCT116 colon cancer cells, PANC-1 pancreatic cancer cells, MCF7 and ZR75 breast cancer cells and HMEC breast cells which express cyclin D1 normally. As shown in cyclin D1 Tables 3 and 4 below, mutation of bases 30 to 21 reduced basal promoter activity to 33% revealing another important and novel activator site for cyclin D1 expression in MCF7 cells. Mutation of bases +1 to +9 or +10 to +19 also reduced basal promoter activity, to 37% and 62%, respectively. A double mutant containing mutations in the CRE (SEQ ID NO:7) and the −30 to −21 site (SEQ ID NO:5) was constructed and transfected into MCF7 cells, resulted in only 11% of the activity of the full-length wild-type promoter retained in all cell lines tested. A double mutant of the CRE in combination with the +1 to +9 site (SEQ ID NO:8) reduced activity to 14%.

TABLE 3

Reporter Activity of Cyclin D1 Promoter Constructs

| Mutant Construct | Mutant Sequence | Wild Type Sequence | % Wild Type Activity |
|---|---|---|---|
| mAP1 | AAAAAAAATACGCGTGAATGGA (SEQ ID NO:84) | AAAAAAAATGAGTCAGAATGGA (SEQ ID NO:92) | 111 ± 12.8 |
| mAP1ds | TCACCAGTTCTTGGACTGT (SEQ ID NO:85) | TCAGAATGGAGATCACTGT (SEQ ID NO:93) | 79 ± 8.4 |
| mE2F | GGAATTGGATCCCATTT (SEQ ID NO:86) | GGAATTTTCGGGCNTTT (SEQ ID NO:94) | 63 ± 10.5 |
| mOCT1 | GGGGCGGGATCCTTCT (SEQ ID NO:87) | GGGGCGATTTGCTTCT (SEQ ID NO:95) | 92 ± 7.7 |
| mSP1 | TGTGCTTTTAATTAAAACCCT (SEQ ID NO:88) | TGCGCCCGCCCCCGCCCCCCT (SEQ ID NO:96) | 105 ± 5.6 |
| CREbam | CAGTGGATCCACACGG (SEQ ID NO:89) | CAGTAACGTCACACGG (SEQ ID NO:7) | 32 ± 1.7 |
| CRE4C | CAGTAAGGTCACACGG (SEQ ID NO:90) | CAGTAACGTCACACGG (SEQ ID NO:7) | 33 ± 5.0 |
| CRE4C5G | CAGTAAGCTCACACGG (SEQ ID NO:91) | CAGTAACGTCACACGG (SEQ ID NO:7) | 33 ± 5.0 |

TABLE 4

Reporter Activity of Cyclin D1 Promoter Constructs

| Construct | Mutations in −30 −21 region | % Wild Type Activity |
|---|---|---|
| WT/−1745 | GAGTTTTGTT (SEQ ID NO:5) | 100 |
| −30 −21/−1745 | TCTGGGATCC (SEQ ID NO:97) | 33 ± 2.2 |
| −30 −26/−1745 | TCTGGTTGTT (SEQ ID NO:98) | 43 ± 3.5 |
| −25 −21/−1745 | GAGTTGGCGG (SEQ ID NO:99) | 34 ± 4.7 |
| −30 −28/−1745 | TCTTTTTGTT (SEQ ID NO:100) | 33 ± 6.3 |
| −28 −23/−1745 | GATGGGATTT (SEQ ID NO:101) | 46 ± 5.1 |
| −23 −21/−1745 | GAGTTTTTCC (SEQ ID NO:102) | 138 ± 16.4 |
| 10 bp 21x/−1745 | GAGTTTTTTTTAAG (SEQ ID NO:103) | 87 ± 11.4 |
| 8 bp 21x/−1745 | GAGTTTTAAAAGAG (SEQ ID NO:104) | 85 ± 7.8 |

To examine the proximal promoter region in more detail, a series of site-specific mutations were made in 10 bp segments from −62 to +20, in the context of the full length promoter (−1745) in pGL3 basic. Luciferase activity was evaluated following transfection into MCF7 cells. The results as shown in Table 5 indicate that mutation of either the 10 bp immediately 5' of the CRE (construct 5'CREm), or of bases −20 to −11 increased promoter activity suggesting the presence of negative transcriptional regulatory sites in these regions. Site-directed mutagenesis of the −30 to −21 promoter region was carried out and constructs assayed in MCF7 cells. The assay results indicate that bases between −30 and −24 (GAGTTTT, nucleotides SEQ ID NO:6) are the most important for transcriptional activation from this site.

TABLE 5

Reporter Activity of Cyclin D1 Promoter Constructs

| Proximal promoter mutant | % wild type activity |
|---|---|
| 5'CREm | 160 ± 3.6 |
| CRE4C | 33 ± 1.8 |
| 3'CREm | 102 ± 7.1 |
| −40 −31 | 113 ± 6.8 |
| −30 −21 | 33 ± 2.2 |
| −20 −11 | 165 ± 19.1 |
| −10 −1 | 111 ± 8.8 |
| +1 +9 | 37 ± 4.0 |
| CRE4C/−30 −21 | 11 ± 1.3 |
| CRE4C/+1 +9 | 14 ± 0.8 |

The identification of sequences important for transcriptional activation suggest that it is possible to specifically regulate endogenous cyclin D1 expression in tumor cells using a regulatory sequence of the promoter.

In vivo footprinting In vivo footprinting of the cyclin D1 promoter was carried out as described in Mueller P R and Wold B, Science, 246(4931):780–786, 1989. Transcription factor binding at the CRE and in the −30 to −21 region were evaluated by in vivo footprinting using dimethyl sulfate (DMS) or UV-light in HCT116 cells. The results of these studies indicate that the CRE is protected in both serum-starved and serum-stimulated cells, consistent with the mode of action for the CRE-binding protein CREB. (See, e.g., KWOK, 1994.) The results also indicate that a protein is binding to the −30 to −21 region in HCT116 cells and that the site is protected in both serum-starved and serum-stimulated cells. The identity of the factor responsible for binding in the −30 to −21 region remains to be determined.

EXAMPLE 2

Identification Of CD40 Ligand (CD40L) Promoter Elements

The full-length human CD40L promoter from −1860 to +49 (SEQ ID NO: 9) was PCR amplified and cloned into the firefly luciferase reporter plasmid pGL3-basic. A 1920 bp element of the CD40L promoter region (from −1860 to +49, FIGS. 5A–C) was PCR-amplified from genomic DNA (Clontech), using the following primers with 5' XhoI and 3' HindIII sites to facilitate subcloning.

TTA TGA TAC CTC GAG GGG AGA GCA TTC AGG AAG ATG (SEQ ID NO:10); and

TGA ATC ACG AAG CTT TGG TAT CTT CTG GCA GAG AAG (SEQ ID NO:11).

All 5' deletions were generated in the same manner using primers containing a 3' HindIII and unique 5' XhoI sequence. Internal deletion and site directed mutants were generated using Quick Change Mutagenesis (Stratagene) as per the manufacturer's recommendations. Mutant constructs were pre-screened by restriction digest of newly modified sites, and confirmed by sequencing. Mutant constructs were purified using a Qiagen endotoxin free isolation system.

Preparation of PBMC Peripheral blood mononuclear cells (PBMC) were purified from buffy coats by Ficoll-Hypaque centrifugation, washed 3 times in Dulbecco's phosphate buffered saline without calcium and magnesium, resuspended at $5 \times 10^6$ cells/ml in RPMI 1640 media (Gibco BRL), 15% FCS (Gibco BRL) and supplemented with 2 mM L-glutamine (Gibco BRL), 1x Penicillin/Streptomycin (Gibco BRL) and 10% IL-2 (Hemagen Diagnostics), then plated in 12-well plates at 2 mls/well. PBMC were then stimulated with TSST-1 (Toxin Technologies) at a final concentration of 50 ng/ml. Cells were cultured at $3-3.8 \times 10^6$ cells/ml, cultured for one week, then subjected to Ficoll-Hypaque centrifugation, and plated in 12-well plates at 3 mls/well at $3 \times 10^6$ cells/ml. Peripheral blood CD4+ T cells were isolated by depletion with CD8+ magnetic microbeads following the manufacturer's protocol (Milteny Biotec) at week two or week three. Following depletion, the peripheral blood CD4+ T cells were stimulated with irradiated allogeneic whole peripheral blood mononuclear cells and TSST-1. Approximately one week later the cells were stimulated again and transfected twenty hours later.

PBMCs were resuspended at $2 \times 10^7$ cells/ml in complete media and 250 μls of the cell suspension transfected with 25 μg of a reporter construct and 0.25 μg of a co-reporter expressing Renilla luciferase (pRLSV40; Promega) at 250 Volts and 960 microfarads using a Gene Pulser 11 (BioRad). Electroporated cells were plated, allowed to rest for 2 hours at 37° C., then activated with PMA (at a final concentration of 25 ng/ml) and ionomycin (at a final concentration of 1.5 μM; Sigma). Nine hours post-activation cells were harvested, washed twice in phosphate buffered saline, lysed in 50 μl of reporter lysis buffer (Promega) and 20 μl of each lysate was assayed for luminescence in an EG&G Berthold Lumat LB9507 luminometer according to the manufacturer's instructions using the Promega's Dual-Luciferase Reporter Assay System.

Analysis of CD40L Promoter Elements A series of 5' CD40L promoter deletions were PCR amplified and cloned into the firefly luciferase reporter plasmid pGL3-basic and the authenticity of all clones verified by DNA sequencing. Promoter activities for the 5' deletion constructs were compared to that of the full-length (−1860) CD40L promoter following transfection into normal expanded T cells and activation with PMA and ionomycin.

Table 6 below, shows the promoter activity of various deletion mutants in activated T cells, some of which affect known transcription factor consensus sites including potential NF-AT and GATA-3 binding sites, as described by Shimadzu et al., 1995.

TABLE 6

Activity of the CD40L promoter with 5' Deletions

| 5' Deletions | % Wild Type Activity |
| --- | --- |
| −1860 | 100% |
| to −1220 | 77% |
| to −951 | 91% |
| to −523 | 111% |
| to −280 | 47% ± 12% |
| to −248 | 25% ± 6.7 |
| to −160 | 53% |
| to −87 | 45% |
| to −60 | 10% ± 1.1% |
| to −26 | 4% |

The results indicate that (1) deletion of CD40L promoter regions between −1860 and −523 had little or no effect on promoter activity; (2) deletion of the CD40L promoter to −427 resulted in slightly elevated promoter activity suggesting that the region may contain a negative regulatory element; and (3) deletion of the promoter to −280, further to −248, still further to −60 and still further to −26 reduces activity relative to the wild-type promoter suggesting the presence of activator sites between −427 and −280, between −280 and −248, between −87 and −60, and between −87 and −26.

A series of internal deletions were made within the context of the full-length −1860 promoter in pGL3-basic to address the possibility that deletion of large promoter regions may remove both positive and negative regulatory elements, and thereby result in cooperative effects. The various deleted CD40L promoter sequences were cloned into the promoter-less firefly luciferase reporter plasmid (pGL3-basic) and co-transfected into expanded T cells together with the SV40 driven Renilla luciferase control plasmid (pRLSV40). Firefly luciferase activity for each construct was normalized to Renilla luciferase activity and reported relative to that of the full-length promoter (−1860), with the length of each 5' deletion construct indicated relative to the transcriptional start site. All internal deletion clones were verified by DNA sequencing. The internal deletion promoter constructs were then transfected into expanded cultures of T cells and activities were compared to that of the −1860 promoter construct following activation with PMA and ionomycin. The results presented as the mean+/−standard error of the mean, for a minimum of 2 independent transfections done in triplicate are provided in Table 7, below.

TABLE 7

Internal Deletions of CD40L and Promoter Activity

| Deletion | % Wild Type Activity | Nucleotide Coordinates |
| --- | --- | --- |
| −930 to −752 | 125% | 941–1119 |
| −730 to −524 | 77% | 1141–1347 |
| −503 to −428 | 71% | 1368–1443 |
| −406 to −301 | 36% | 1465–1570 |
| −320 to −291 | 34% ± 3.5% | 1551–1580 |
| −300 to −281 | 50% ± 18% | 1571–1590 |
| −280 to −231 | 37% | 1591–1640 |
| −230 to −211 | 15% ± 3.7% | 1641–1660 |

TABLE 7-continued

Internal Deletions of CD40L and Promoter Activity

| Deletion | % Wild Type Activity | Nucleotide Coordinates |
|---|---|---|
| −230 to −110 | 13% ± 2.2 | 1641–1761 |
| −87 to −68 | 26% ± 3% | 1784–1803 |
| −160 to −60 | 20% ± 6.2% | 1711–1811 |
| −72 to −49 | 4% ± 1.7% | 1799–1822 |
| −61 to −40 | 2.5% ± 0.7% | 1810–1834 |
| −40 to +9 | 26% | 1831–1880 |
| +9 to +29 | 14% ± 2.7 | 1880–1900 |

Internal deletions which resulted in reduced promoter activity include: (1) the −406 to −301 region, 3-fold reduction in activity relative to wild type; (2) the −320 to −291 region, 3-fold reduction in activity relative to wild type; (3) the −300 to −281 region, 2-fold reduction in activity relative to wild type; (4) the −280 to −231 region, 3-fold reduction in activity relative to wild type; (5) the −230 to −211 region, 6 to 7-fold reduction in activity relative to wild type; (6) the sequence immediately upstream of the −66 NF-AT site (deletion −87 to −68), 4-fold reduction in activity relative to wild type; (7) the −72 to −49 region, 25-fold reduction in activity relative to wild type; (8) the −61 to −40 region, 40-fold reduction in activity relative to wild type; and (9) the +9 to +29 region (downstream of the transcriptional start site), 14% reduction in activity relative to wild type.

In addition, various site-specific mutants constructed within the context of the full-length CD40L promoter (−1860 to +49) in pGL3-basic were co-transfected into normal expanded T cells together with the pRLSV40 control plasmid. Firefly luciferase activity for each construct was normalized to Renilla luciferase activity relative to that of the full-length wild-type promoter (Table 8). In the table, the positions of known transcription factor binding sites are indicated and numbered relative to the transcriptional start site (+1) with data presented as the mean+/−standard error of the mean for a minimum of 2 independent transfections done in triplicate.

TABLE 8

Site Specific Mutations and Promoter Activity

| Mutation | Wild Type Sequence | % Wild Type Activity |
|---|---|---|
| −1194 NFkB | GGGATTTCC | 83% |
| −760 NF-AT | TTTTCC | 91% |
| −599 NF-AT | GGAAAA | 100% ± 0% |
| −306 | TTGTCACTTTC (SEQ ID NO:105) | 24% ± 4% |
| −269 GATA-3 | GTGATA | 67% |
| −264 NF-AT | GGAAAA | 73% ± 25% |
| −66 NF-AT | TTTTCC | 32% ± 4% |
| −37 to −29 TFIIB | GTGCGCT | 53% ± 19% |
| −30 to −25 TATA | CTTAAC | 47% ± 12% |
| −220 to −214 | GGCAAG | 26% ± 3.5% |
| −214 to −208 | AATGAA | 31% ± 6.9% |
| −208 to −202 | TATATG | 38% ± 9.9% |
| −202 to −196 | GAAGAA | 36% ± 4 |
| −220 to −208 | GGCAAGAATGAA (SEQ ID NO:106) | 18% ± 2.6 |
| −72 to −66 | AGCACA | 49% ± 48% |
| −66 to −60 | TTTTCC | 31% ± 5.8 |
| −60 to −54 | AGGAAG | 42% ± 2 |
| −54 to −48 | TGTGGG | 19% ± 3.8 |
| −48 to −42 | CTGCAA | 50% ± 6% |
| −72 to −60 | AGCACATTTTCC (SEQ ID NO:107) | 10% ± 1.8% |
| −66 to −54 | TTTTCCAGGAAG (SEQ ID NO:108) | 7% ± 1.8% |
| −66 to −60 and −54 to −48 | TTTTCC TGTGGG (SEQ ID NO:109) | 14% ± 2.2% |
| −66 to −60 and −48 to −42 | TTTTCC CTGCAA (SEQ ID NO:110) | 15% |
| −54 to −42 | TGTGGCTGCAA (SEQ ID NO:111) | 20% ± 5.5% |
| −66 to −48 | TTTTCCAGGAAGTGTGGG (SEQ ID NO:112) | 11% ± 1.5% |
| −72 to −60 and −54 to −48 | AGCACATTTTCC TGTGGG (SEQ ID NO:113) | 8% ± 1.4% |
| −66 to −60 and −54 to −42 | TTTTCC TGTGGGCTGCAA (SEQ ID NO:114) | 5% ± 15% |

The results show that at least 4 regions of the CD40L promoter are critical to expression in activated T cells, as indicated by the levels of luciferase reporter expression and DNA footprinting studies. The regions of the CD40L promoter suggested by these results to be critical to expression in activated T cells include: (1) the site in the vicinity of nucleotide −306 (SEQ ID NO:12), the specific mutation of which results in a 4-fold down regulation of CD40L promoter activity; (2) the region between −230 and −196 (SEQ ID NO:14), based on deletion of the −230 to −211 region (SEQ ID NO:13), which resulted in an 6 to 7-fold down-regulation of CD40L promoter activity, and site specific mutations of −220 to −214, −214 to −208, −208 to −202 or −202 to −197, which resulted in a 2.5 to 4-fold down regulation of promoter activity; and (3) the region between −77 and −40 (SEQ ID NO:15), based on the expression level of deletion mutants, wherein an internal deletion of −72 to −49 or −61 to −40 resulted in a 25-fold or 40-fold down-regulation respectively. In addition, specific mutations in the composite AP-1/−66 NF-AT site together with a previously unidentified site located between −48 and −54 indicates a contribution to transcriptional activation through the −48 to −54 site. (See Tables 7 and 8)

It will be appreciated that some CD40L promoter regions may bind more than one transcription factor, and targeting a DNA-binding compound to the regulatory region of the CD40L promoter, described above, provides a means to inhibit CD40L promoter-mediated transcription through modulation of transcription factor-DNA interactions.

EXAMPLE 3

Hepatitis B (HBV)

A linearized unit-length HBV genomic fragment was prepared from an HBV plasmid containing 1.3 copies of a viral genomic sequence such that either the core, the preS1 or the X promoter was at the extreme 3' end. This fragment, when cloned into a reporter construct directionally, placed the promoter element immediately upstream of the reporter coding sequence in order to drive its expression. Luciferase reporter activities of these wild type core, X, and preS1 promoter constructs were evaluated by transient transfection experiments in cell lines of hepatic origin such as HepG2, Huh7, 22.1.5, and HepAD38. Subsequent mutant promoter constructs, prepared by site-directed mutations or linker scanner mutation, were prepared from these wild type clones using mutagenesis methods known in the art.

HBV Core Promoter

A luciferase reporter construct was constructed with a linearized full-length copy of the HBV genome, with the core promoter positioned immediately upstream and driving the expression of the reporter. Mutagenic primers containing blocks of 15 nucleotides of targeted sequence mutation were designed to generate a series of linker scanner mutant promoter reporter clones using either a Morph™ (5'Prime to 3'Prime, Boulder, Colo.) or a QuikChange™ (Stratagene, La Jolla, Calif.) mutagenesis protocol.

Targeted segments of the promoter found to be resistant to mutagenesis were further sub-divided into smaller blocks of mutations consisting of 7–8 nucleotides. This series of linker scanner clones spanned the entire length of the core promoter segment. Mutagenic primers were also used to construct site-directed mutant constructs of known transcription factor binding sites including the hepatocyte nuclear factor sites, HNF3 and HNF4.

To determine potential critical regulatory elements in the core promoter, linker scanner analysis was performed using the series of systemic mutation clones constructed. Each linker scanner mutant construct was evaluated for promoter activity in transient transfection experiments based on luciferase reporter activity in the hepatoma-derived cell lines HepG2 and HuH7. The HBV stably-transfected cell lines, 22.1.5 and HepAD38, were also used in the linker scanner analysis. An increase or decrease in relative luciferase reporter activity relative to the wild type indicated the presence of potential control elements critical to regulation of gene transcription.

Three regions of interest were identified in the linker scanning analysis. Mutations in domains 5, 8/9, and 13 resulted in 4–10 fold decrease in promoter activity (Table 9). All 3 regions align with cis-elements previously reported in the literature. Domain 5 contains sequences corresponding to a HNF4 transcription factor binding site (AGGACTCTTGGA SEQ ID NO:18). Domains 8/9 contain sequences corresponding to a HNF3 transcription factor binding site (proximal, HNF3-2, GACTGTTTGTTT, SEQ ID NO:17). Both of these protein factor sites have been described as important activation elements for the HBV core promoter. Domain 13 mutations abolish the TATA box sequence (CATAAA) of the promoter. A second HNF3 site (HNF3-1, domain 6) has been reported upstream of the one located in domains 8/9. However, mutation of this distal HNF3 site did not show any effects in promoter activity.

TABLE 9

Reporter Analysis of Linker Scanner Mutation Clones of the HBV Core Promoter

| Domain | Nucleotide Coordinates[1] | Linker Scanner Sequence | Wild Type Sequence | Percent Wild Type | |
|---|---|---|---|---|---|
| | | | | HepG2 | HepAD3 |
| 1 | 1601–1615 | TACATGATATCTTCT (SEQ ID NO:115) | GCACGTCGCATGGAG (SEQ ID NO:129) | | |
| 2 | 1616–1630 | CAAGAATTCCCATAA (SEQ ID NO:116) | ACCACCGTGAACGCC (SEQ ID NO:130) | 88 | 147 |
| 3 | 1631–1645 | ACAACCCGCGGTAAA (SEQ ID NO:117) | CACCAAATATTGCCC (SEQ ID NO:131) | 79 | 65 |
| 4 | 1646–1660 | CCTTGAGGCACGCGT (SEQ ID NO:118) | AAGGTCTTAGATAAG (SEQ ID NO:132) | 28 | 38 |
| 5–1 | 1661–1668 | CTCTAGAG | AGGACTCT | 34 | 10 |
| 5–2 | 1668–1675 | GGTCTAGA | TTGGACTC | 22 | 18 |
| 6 | 1676–1690 | GACGTCCGTGACCAT (SEQ ID NO:119) | TCAGCAATGTCAACG (SEQ ID NO:133) | 91 | 128 |
| 7 | 1691–1705 | CAATCAAGATCTTAC (SEQ ID NO:120) | ACCGACCTTGAGGCA (SEQ ID NO:134) | 76 | 93 |
| 8 | 1706–1720 | GCAGGACCCTCGAG (SEQ ID NO:121) | TACTTCAAAGACTGT (SEQ ID NO:19) | 7 | 9 |
| 9–1 | 1721–1728 | GGTGCACC | TTGTTTAA | 14 | 11 |
| 9–2 | 1728–1735 | CTAGTGTT | AAGACTGG | 24 | 17 |

TABLE 9-continued

Reporter Analysis of Linker Scanner Mutation Clones of the HBV Core Promoter

| Domain | Nucleotide Coordinates[1] | Linker Scanner Sequence | Wild Type Sequence | Percent Wild Type | |
|---|---|---|---|---|---|
| 10 | 1736–1750 | TCTTCTAGATTTTCT (SEQ ID NO:122) | GAGGAGTTGGGGAG (SEQ ID NO:135) | 22 | 22 |
| 11 | 1751–1765 | TCTCGGCTTGGCCAT (SEQ ID NO:123) | GAGATTAGGTTAAAG (SEQ ID NO:136) | 24 | 26 |
| 12-1 | 1766–1773 | TGCGCATG | GTCTTTGT | 103 | 103 |
| 12-2 | 1771–1780 | GTGCACCTTC (SEQ ID NO:124) | TGTACTAGGA (SEQ ID NO:137) | 37 | 36 |
| 13 | 1781–1795 | TTAGTGCTTAAGCCC (SEQ ID NO:125) | GGCTGTAGGCATAAA (SEQ ID NO:21) | 16 | 14 |
| 14 | 1796–1810 | GCTCGAGTATACAAC (SEQ ID NO:126) | TTGGTCTGCGCACCA (SEQ ID NO:138) | 37 | 68 |
| 15 | 1811–1825 | TACAACGTACCCGGG (SEQ ID NO:127) | GCACCATGCAACTTT (SEQ ID NO:139) | 129 | 185 |
| 16 | 1826–1840 | GGACAAGCTTAAGCC (SEQ ID NO:128) | TTCACCTCTGCCTAA (SEQ ID NO:140) | 229 | 247 |

[1]HBV ayw strain

The mutation of several additional regions, as shown in Table 10 showed a reduction in promoter activity of more than 4-fold. These regions, domain 5; domain 8/9 (HNF3 transcription factor binding site); and domain 13 (CATAA box) appear to align with the cis-elements (HNF-4/HNF-3, HNF-3/Sp1, and TATA box, respectively) reported in the literature, with the proximal HNF-3 site indicated as one critical element. The results of expression studies presented in Table 9 suggest that domain 8 (SEQ ID NO: 19); domain 8/9-1 (SEQ ID NO:20); and domain 13 (SEQ ID NO: 21) are involved in transcriptional activation.

TABLE 10

Reporter Analysis of Site-Directed Mutants of HNF3 and HNF4 Sites of the HBV Core Promoter

| | Nucleotide Coordinates (HBV ayw Strain) | Site-Directed Mutant Sequence | Percent Wild Type HepAD38 |
|---|---|---|---|
| Distal HNF3 | 1680–1691 | CCAGGGCCCCGA (SEQ ID NO:141) | 102 |
| Proximal HNF3 | 1715–1726 | GCCGCGGTCTGT (SEQ ID NO:142) | 33 |
| HNF4 | 1661–1672 | CGTCCGCGGTGA (SEQ ID NO:143) | 29 |

Following identification of the TATA box and the HNF4 and proximal HNF3 sites as the control elements most critical for core promoter activity, transcriptional activation as a result of the binding of the TATA binding protein (TBP) and the HNF transcription factors were further studied. It will be appreciated that failure of these protein factors to bind would result in down-regulation of the promoter.

Small DNA-binding compounds were utilized to test their ability to alter the transcription level from wild type and engineered HBV core promoters, either by interference and/or displacement of protein factor binding to its cognate nucleotide binding sequences, as further described in co-owned U.S. Ser. No. 09/518,297, filed Mar. 3, 2000. The results suggested that a compound binding site may be engineered into a promoter and thereby serve as a means for regulated gene expression of a coding sequence operably linked thereto.

preS1 promoter A luciferase reporter construct was generated containing a full-length copy of the HBV genome with the preS1 promoter positioned immediately upstream of the luciferase reporter gene. Using a wild type luciferase reporter clone, PreSpLuc, as a template, site-directed mutagenesis was performed using a Morph™ (5'Prim→3'Prime, Boulder, Colo.) method to generate four mutants in known transcription factor binding sites and eight 15 bp linker scanner mutants. The mutagenized constructs were transiently transfected into Hep3AD38 and tested for promoter activity, as described above. Table 11 shows the results of the mutation analysis and the ability of the mutated promoters to drive luciferase expression.

TABLE 11

PreS1 Promoter Activity of Mutants

| Construct | Coordinate | Mutated Sequence | % Wild type Activity |
|---|---|---|---|
| HNF1 | 2720–2732 | 5' TCGCGAACGGCAG (SEQ ID NO:144) | 6 |
| HNF3 | 2744–2755 | 5' ACAGCGCGCACA (SEQ ID NO:144) | 40 |
| Sp1 | 2765–2774 | 5' CGATATCTGC (SEQ ID NO:145) | 48 |
| TBP | 2778–2784 | 5' GCGCGCC (SEQ ID NO:146) | 34 |
| Domain 1 | 2702–2716 | 5' GCGGCGAACTGCACG (SEQ ID NO:147) | 182 |

TABLE 11-continued

PreS1 Promoter Activity of Mutants

| Construct | Coordinate | Mutated Sequence | % Wild type Activity |
|---|---|---|---|
| Domain 2 | 2717–2731 | 5' AGCCGCGGGACGGCA (SEQ ID NO:148) | 8 |
| Domain 3 | 2732–2746 | 5' GGAACCCAGCTGACA (SEQ ID NO:149) | 62 |
| Domain 4 | 2747–2761 | 5' GCGCGCACACAGAGC (SEQ ID NO:150) | 103 |
| Domain 5 | 2762–2776 | 5' GTCTGCAGTTTGCGC (SEQ ID NO:151) | 115 |
| Domain 6 | 2777–2791 | 5' GGCGCGCCTCTCTCC (SEQ ID NO:152) | 34 |
| Domain 7 | 2792–2806 | 5' CAGCTGACGCTATAA (SEQ ID NO:153) | 53 |
| Domain 8 | 2807–2821 | 5' GACGGGCCCTTTGAG (SEQ ID NO:154) | 55 |

Among known transcription factor binding sites, the HNF1 site appears to be the most critical to preS1 promoter activity, as evidenced by the activity of the HNF1 mutant (16-fold reduction in activity). The domain 2 site (SEQ ID NO: 23) overlaps the HNF1 site and a domain 2 mutant showed a 13-fold reduction in activity. A domain 6 mutant showed a 3-fold reduction in activity suggesting that the domain 6 site (SEQ ID NO: 24) is also involved in transcriptional activation. Mutation of the HNF3, Sp1 and TBP binding sites resulted in a 2 to 3-fold reduction in reporter activity. In constructs with double mutations in HNF1 and TBP sites, there was no further reduction in reporter activity. In contrast, in Sp1 double mutants with either HNF3 or TBP, there was a further reduction relative to the reporter activity observed for the constructs with a mutation in HNF3, Sp1, or TBP alone.

To further map the HNF1 site, four serial 4 bp mutants with a 1 bp overlap were constructed and tested for promoter activity in luciferase reporter constructs (Table 12).

TABLE 12

HNF1 Linker-Scanning Mutagenesis

| Construct | HNF1 sequence | % Wild type Activity |
|---|---|---|
| Wild type | GTTAATCATTACT (SEQ ID NO:155) | 100 |
| HNF1-A | TCGCATCATTAC (SEQ ID NO:156) | 4 |
| HNF1-B | GTTCCGAATTAC (SEQ ID NO:157) | 3 |
| HNF1-C | GTTAATACGGAC (SEQ ID NO:158) | 4 |
| HNF1-D | GTTAATCATGCAG (SEQ ID NO:159) | 5 |

A series of point mutations spanning the HNF1 binding site were carried out and the mutants tested for luciferase expression following transient transfection. Four of seven mutants retained 14–42% of wild type activity as shown in Table 13, below.

TABLE 13

Mutants In The HNF1 Site Of The PreS1 Promoter

| | | Relative Luciferase Activity (%) | | |
|---|---|---|---|---|
| Consensus | *GTT AAT NAT TAA C* | | | |
| Wild type | GTT AAT CAT TAC TT (SEQ ID NO:161) | 100 | 100 | 100 |
| mHNF1 | TCG CAG ACG GCA GT (SEQ ID NO:162) | 5 | 5 | 5 |
| HNF1–4A | GTT GAT CAT TAC TT (SEQ ID NO:163) | – | 5 | – |
| HNF1–5A | GTT ACT CAT TAC TT (SEQ ID NO:164) | 42 | 30 | – |
| HNF1–5B | GTT AGT CAT TAC TT (SEQ ID NO:165) | 20 | – | – |
| HNF1–6A | GTT AAG CAT TAC TT (SEQ ID NO:166) | – | 6 | – |
| HNF1–6B | GTT AAC CAT TAC TT (SEQ ID NO:167) | 29 | – | – |
| HNF1–9A | GTT AAT CAG TAC TT (SEQ ID NO:168) | – | 3 | – |
| HNF1–9B | GTT AAT CAC TAC TT (SEQ ID NO:169) | 14 | – | – |
| HNF1–5A6B | GTT ACC CAT TAC TT (SEQ ID NO:170) | – | – | 9 |
| HNF1–5A9B | GTT ACT CAC TAC TT (SEQ ID NO:171) | – | – | 4 |

A fluorescence-based assay for characterization of ligands with DNA binding properties was carried out, the results of which are shown in FIG. 2. A Hybridization Stabilization assay (HSA) was carried out using a 5'-fluorescent-labeled ssDNA and a 3'-Dabsyl labeled complementary strand of DNA. The oligonucleotides were designed to remain single stranded at room temperature until the ligand binds and duplexes the two strands resulting in quenching of the fluorescent signal. The direct binding of the ligand can then be unquenched by the presence of a more preferred sequence duplex. If a duplex does not have a preferential site for the particular ligand then the signal remains quenched. FIG. 2 shows the results of a study where six different duplexes were tested against a particular ligand using a fluorescence-based assay for characterization of ligands with DNA binding properties. A Hybridization Stabilization assay (HSA) was carried out using a 5'-fluorescent-labeled ssDNA and a 3'-Dabsyl labeled complementary strand of DNA. The oligonucleotides were designed to remain single stranded at room temperature until the ligand binds and duplexes the two strands resulting in quenching of the fluorescent signal. The direct binding of the ligand can then be unquenched by the presence of a more preferred sequence duplex. If a duplex does not have a preferential site for the particular ligand then the signal remains quenched. FIG. 2 shows the reporter coding sequence. Promoter constructs were prepared with successive blocks of 21 base pair mutated sequences from the HBV X promoter or known transcription factor binding sites.

Mutant constructs were transfected into the hepatoma-derived cell-line HepG2, HepG2 and cell lines stably transfected with HBV: 22.1.5 and HepAD38, and the expression of the luciferase reporter gene analyzed to determine HBV promoter activity. As indicated in Table 14, mutations in domains 3, 4 and 6 resulted in 28–51% of wild type activity when tested in 3 different cell lines.

TABLE 14

Linker Scanning Mutants of X Promoter

| Construct | Coordinate | Mutated Sequence | % Wild Type Activity (HepG2) | % Wild Type Activity (2.2.15) | % Wild-Type Activity (HepAD38) |
|---|---|---|---|---|---|
| Domain 1 | 1083–1103 | 5' CCTACTTCGCGACAGGGAGAT (SEQ ID NO:172) | 110(343/103) | 172/75 | 230/100 |
| Domain 2 | 1104–1124 | 5' AACCAGGGCCCTTATGGGAGT (SEQ ID NO:173) | 95/98 | 69 | 58 |
| Domain 3 | 1125–1145 | 5' GTGCCCATCGCGAGTCCAAGG (SEQ ID NO:174) | 33/38 | 51 | 40 |
| Domain 4 | 1146–1166 | 5' GCAAAATGGGATATCACCATT (SEQ ID NO:175) | 59/36 | 51 | 45 |
| Domain 5 | 1167–1187 | 5' AACTGCAGTGTAACCTGTGGG (SEQ ID NO:176) | 113/105 | 83 | 119 |
| Domain 6 | 1188–1208 | 5' TACAGATATCAAAAACAGTTA (SEQ ID NO:177) | 33/40 | 28 | 33 |
| Domain 7 | 1209–1229 | 5' GTTTTAGGATATCGTTTAACG (SEQ ID NO:178) | 81/85 | 71 | 66 |
| Domain 8 | 1230–1250 | 5' ACTATACGGATATCCCAAGGG (SEQ ID NO:179) | 41/47 | 64 | 47 |
| Domain 9 | 1251–1271 | 5' GATTACAAGAGATATCGAACG (SEQ ID NO:180) | 48(56/39) | 80/49 | 72/32 |
| Domain 10 | 1272–1292 | 5' CAGTATTCCAGAAGATATCAG (SEQ ID NO:181) | 51/50 | 62 | 70 |
| Domain 11 | 1293–1313 | 5' GTGGGGAAGATATCACTTGAG (SEQ ID NO:182) | 117/168 | 124 | 152 |
| Domain 12 | 1314–1334 | 5' TTCTACCCACGGCGATATCAG (SEQ ID NO:183) | 128 | — | — |
| Domain 23 | 1335–1355 | 5' TCGCCAGAGTCGCGAAGCGAA (SEQ ID NO:184) | 102/100 | 110 | 85 | results of a study where six different duplexes were tested against a particular ligand. In the study, fluorescent and dabsyl labeled oligos at 25 nM and 35 nM were duplexed with the 21X ligand at 75 nM. Various other duplexes were then added from 0 to 600 nM to determine the sequence binding preference of the ligand. Reactions were in 225 μl of 10 mM HEPES pH 7.2, 50 mM NaCl, 0.1 mM EDTA and equilibrated at room temperature overnight.

The sequence that allows for the greatest fluorescence recovery is considered to be a preferred sequence for the ligand. The observed order of binding preferences for 21x was: HNF1-21X>TBP wild type>HNF1 wild type>HNF3 wild type>TBP mutant>HNF1 mutant (FIG. 2). These results are consistent with the fact that in both the TBP and HNF1 mutant oligos, the majority of A/T bases were changed to G/C bases.

HBV X Promoter

The HBV X promoter was analyzed by deletion and linker-scanning experiments similar to those described for the core promoter.

A luciferase reporter construct was constructed with a full-length copy of the HBV genome and the HBV X promoter (FIG. 3) positioned immediately upstream of a The wild type sequence for domains 3 through 6, are as follows:

Domain 3:  TGTAAACAATACCTGAACCTT  (SEQ ID NO:26)

Domain 4:  TACCCCGTTGCCCGGCAACGG  (SEQ ID NO:27)

Domain 6:  GCTGACGCAACCCCCACTGGC  (SEQ ID NO:28)

Two double mutants (domains 3+6 and domains 4+6), yielded a 7 to 9-fold reduction in activity relative to wild type controls when evaluated in the HepAD38 cell line (Table 15).

TABLE 15

Double Mutants of X Promoter

| Mutant Clones | % Wild Type Activity |
|---|---|
| M3 + M4 | 43 |
| M3 + M6 | 14 |
| M4 + M6 | 11 |

Additional HBV-X promoter reporter constructs were made with mutations in various known transcription factor binding sites (Gustin K et al., *Virology* 193, 653–660, 1993; Guo W et al., *J. Virol.*, 1991; Nakamura I et al., *Virology* 191, 533–540, 1992), and evaluated for luciferase reporter activity. The results of those studies which are presented in Table 16 suggest that the EF-C and E factor binding sites are important to activity of the HBV X promoter.

TABLE 16

Mutants of Transcription Factor Binding Sites of X Promoter

| Domain | Coordinate | Mutated Sequence | % WT Activity (HepG2) | % WT Activity (2.2.15) | % WT Activity (HepAD38) |
|---|---|---|---|---|---|
| NF1 | 1100–1119 | CTCGCCAACTTACAAGGCCT (SEQ ID NO:185) | 109/109 | 119 | 93 |
| 2C | 1119–1134 | TTTCTGTGTAAACAAT (SEQ ID NO:186) | 97/89 | 74 | 56 |
| EF-C | 1148–1168 | CCCCGTTGCCCGGCAACGGCC (SEQ ID NO:187) | 46/44 | 36 | 28 |
| E | 1180–1202 | CTGACGCAACCCCC (SEQ ID NO:188) | 47/39 | 53 | 39 |
| NF1 | 1209–1229 | TGGGGCTTGGTCATGGGCCA (SEQ ID NO:189) | 88/95 | 80 | 78 |
| NF1 | 1216–1236 | TGGTCATGGGCCATCAGCGC (SEQ ID NO:190) | 74/77 | 110 | 71 |
| X-PBP | 1229–1245 | ATCAGCGCATGCGTGGAA (SEQ ID NO:191) | 56/61 | 69 | 48 |

Given that all HBV-X promoter reporter constructs contained the entire HBV genome, two additional constructs were made: X enhancer/promoter reporter (XpLuc200, Table 17), and the entire HBV genome without X enhancer/promoter-reporter Xp(–) Luc3000, Table 17), to exclude the possibility that there is read-through from other HBV promoters. The XpLuc200 construct was made by amplifying a clone from each of domain 3, 4, and 18 with the forward and reverse primers (SEQ ID NO:29) and (SEQ ID NO:30), respectively, followed by cloning into the pGL3 Basic vector. The "Xp(–) Luc3000" construct was made by subjecting the wild type construct XpLuc (29-1-5) to site-directed mutagenesis by Morph™ method. All "XpLuc200" constructs, 3.6, 4.9, 18.13, and 29-1-5, showed approximately 1.5 to 2 fold promoter activity relative to that of each full-length construct, while the Xp(–) Luc3000 construct (29-1-5(-Xp)) showed no promoter activity. These results support the conclusion that the reporter activity presented in Tables 14 and 16 reflect an effect on the HBV X promoter alone, and is not due to upstream HBV promoters (Sp, preSp or Cp).

TABLE 17

XpLuc200 and Xp(–)Luc3000 Constructs

| | Presence of promoters | | | | Proximal promoter |
|---|---|---|---|---|---|
| Construct | Cp | PreS1p | Sp | Enh1/Xp | of reporter gene |
| XpLuc200 | – | – | – | + | Xp |
| Xp(–)Luc3000 | + | + | + | – | Sp |

EXAMPLE 4

Vancomycin-Resistant Enterococci (VRE)

A modified pAM401 plasmid (ATCC) was designed containing a VRE promoter sequence upstream of the luciferase gene in a background allowing for growth and maintenance in *E. coli* and Enterococcus species. The vanH promoter (SEQ ID NO:31) was PCR amplified from VRE strain CSUC4 with NcoI and SalI sites added to it. The pAM401 plasmid was cut using XbaI and SalI and triple ligated to the firefly luciferase gene isolated from pGL3 basic (Promega) by cutting XbaI to NcoI and incorporating the vanH promoter into the construct.

Transformants were screened by restriction analysis following PCR amplification and the resulting plasmids electroporated into L-threonine treated Enterococcus strain CSUC-4.

Site directed mutagenesis of the VRE promoter region was carried out by systematically altering short 8 to 10 bp regions of the consensus promoter sequence, including the –35 consensus binding site within the phosphorylated VanR footprint (Arthur et al., 1992).

Figure 7:
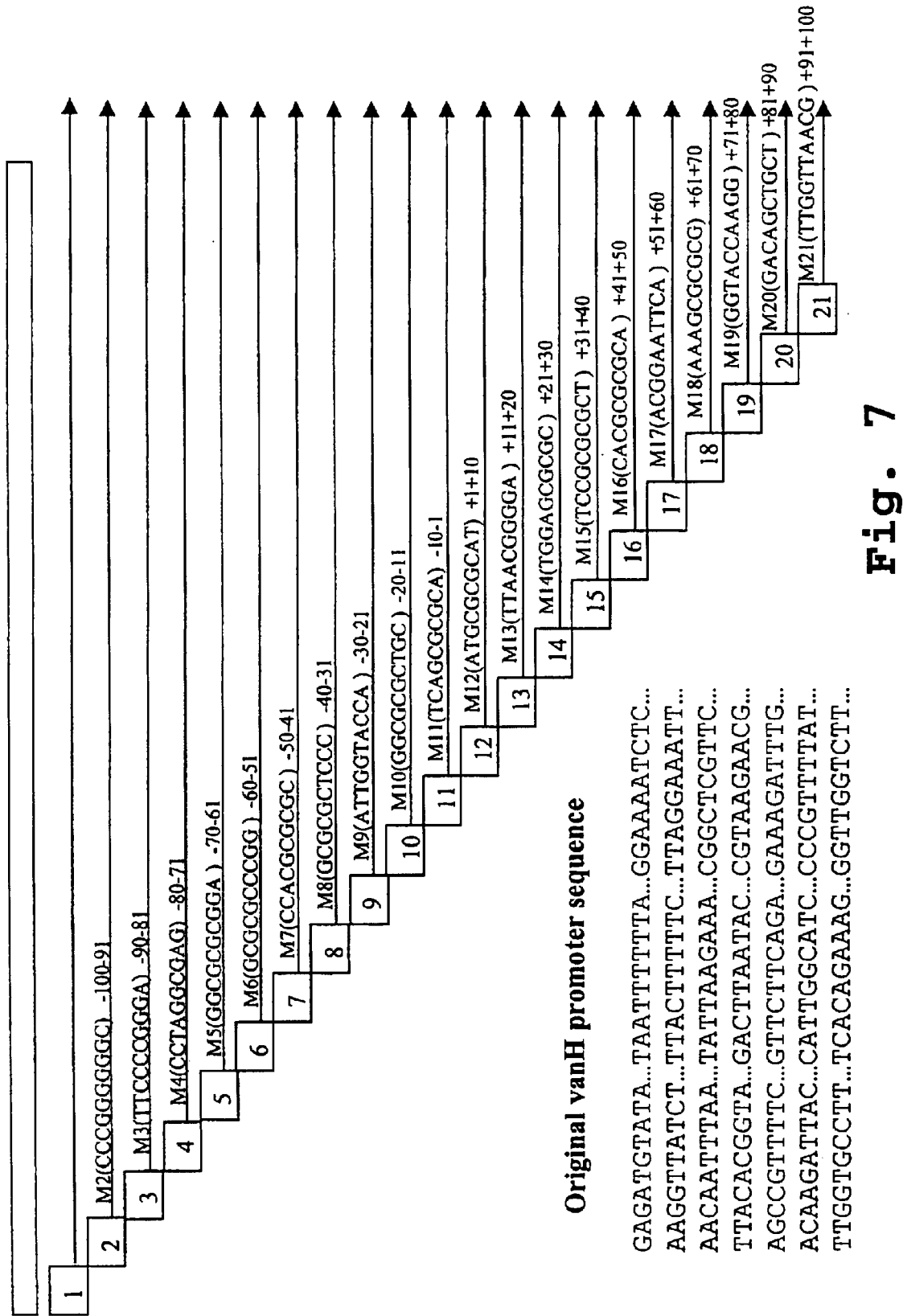
FIG. 7 presents the sequences of vanH promoter mutants M2–M21 (SEQ ID NO:79 and 192–210), wherein each group of 10 nucleotides in the original vanH promoter sequence (SEQ ID NO:31) shown in the figure was replaced with the mutant sequence, e.g., in M2 the CCCGGGGGGC (SEQ ID NO:79) sequence was inserted in place of the wild type TAATTTTTA (SEQ ID NO:80) sequence.

20 linker scanning mutant designated M2–M21 were generated an nucleic acid constructs containing the VRE promoter sequence upstream of the luciferase gene were subcloned into the a pRLUC parent vector and transformed into *E. coil*. FIG. 7 presents the sequences of vanH promoter mutants M2–M21, wherein each group of 10 nucleotides in the original vanH promoter sequence shown in the figure was replaced with the mutant sequence, e.g., in M2 the CCCGGGGGGC sequence (SEQ ID NO:79) was inserted in place of the wild type TAATTTTTTA sequence (SEQ ID NO:80). The position of the mutations and corresponding luciferase activity is shown in Table 18.

The luciferase expression of selected promoter mutants was analyzed in 3 clinical strains of Enterococcus to ascertain if the effect of modified promoter elements on expression is consistent between strains. CSUC-4, the initial strain assayed, UCD-3 and UL-178 were used in the analysis. The M9 clone consistently resulted in the highest luciferase activity of the mutants tested. Among the other mutants M8 also had a consistent effect on induction. (See Table 18.)

TABLE 18 vanH Promoter Mutants And Reporter Activity

| Construct | Coordinate | Mutated Sequence | % Wild Type Activity (UCD3) | % Wild Type Activity (UL17) | % Wild Type Activity (CSUC4) |
|---|---|---|---|---|---|
| M2 | −100 to −91 | CCCGGGGGGC (SEQ ID NO:79) | 120.4 | 53.6 | 10.7 |
| M3 | −90 to −81 | TTCCCCGGGA (SEQ ID NO:192) | 108.7 | 38.7 | 10.3 |
| M4 | −80 to −71 | CCTAGGCGAG (SEQ ID NO:193) | — | — | 0.4 |
| M5 | −70 to −61 | GGCGCGCGGA (SEQ ID NO:194) | — | — | 1.6 |
| M6 | −60 to −51 | GCGCGCCCGG (SEQ ID NO:195) | 36.5 | 10.3 | 0.4 |
| M7 | −50 to −41 | CCACGCGCGC (SEQ ID NO:196) | 45.5 | 18.9 | 1.8 |
| M8 | −40 to −31 | GCGGGCTCCC (SEQ ID NO:197) | 0.1 | 0.0 | 1.3 |
| M9 | −30 to −21 | ATTGGTACCA (SEQ ID NO:198) | 152.5 | 100.9 | 1202 |
| M10 | −20 to −11 | GGCGCGCTGC (SEQ ID NO:199) | — | — | 32.6 |
| M11 | −10 to −1 | TCAGCGCGCA (SEQ ID NO:200) | 1.3 | — | 1405 |
| M12 | +1 to +10 | ATGCGCGCAT (SEQ ID NO:201) | — | — | 1737 |
| M13 | +11 to +20 | TTAACGGGGA (SEQ ID NO:202) | — | — | 770.7 |
| M14 | +21 to +30 | TGGAGCGCGC (SEQ ID NO:203) | — | — | 115.2 |
| M15 | +31 to +40 | TCCGCGCGCT (SEQ ID NO:204) | — | — | 50.6 |
| M16 | +41 to +50 | CACGCGCGCA (SEQ ID NO:205) | — | — | 23.6 |
| M17 | +51 to +60 | ACGGAATTCA (SEQ ID NO:206) | — | — | 2.4 |
| M18 | +61 to +70 | AAAGCGCGCG (SEQ ID NO:207) | — | — | 76.3 |
| M19 | +71 to +80 | GGTACCAAGG (SEQ ID NO:208) | — | — | 57.3 |
| M20 | +81 to +90 | GACAGCTGCT (SEQ ID NO:209) | — | — | 0.0 |
| M21 | +91 to +100 | TTGGTTAACG (SEQ ID NO:210) | — | — | 12.6 |

Each linker scanner promoter mutant was tested for activity, with both up- and down-regulation observed. The largest decrease was to 0% of wild type activity and the largest increase was 1737% of wild type activity. All mutants in the region reported to be footprinted by phosphorylated VanR (M2–M8) showed decreased activity. Increased activity was observed in mutants spanning nucleotides −30 to +20 (M9–M13), suggesting the possibility of a repressor binding site in this region. Of particular interest are putative activator sequences which correspond to M6 (SEQ ID NO:32) and M8 (SEQ ID NO:33), and a putative repressor sequence which corresponds to M12 (SEQ ID NO:34).

EXAMPLE 5

Androgen Receptor

The androgen receptor promoter from nucleotides −6000 to +1100 (FIGS. 8A–C, SEQ ID NO:35), was cloned from genomic DNA by PCR using GenBank sequences and subcloned into pGL3 basic (Promega) for subsequent transient transfection.

A large series of deletion constructs were made and tested in the androgen dependent prostate cell line, LNCaP, following transient transfection.

The deletion constructs were made using the following PCR primer pairs: for the −6000+1 construct (SEQ ID NO:36) and (SEQ ID NO:37); for the −4000+1 construct (SEQ ID NO:38) and (SEQ ID NO:39); for the −2000+1 construct (SEQ ID NO:40) and (SEQ ID NO:41); for the −2000+1100 construct (SEQ ID NO:42) and (SEQ ID NO:43); for the −200+1 construct (SEQ ID NO:44) and (SEQ ID NO:45); for the −200+100 construct (SEQ ID NO:46) and (SEQ ID NO:47); for the −400+1 construct (SEQ ID NO:48) and (SEQ ID NO:49); for the −300+1 construct (SEQ ID NO:50) and (SEQ ID NO:51); for the −150+1 construct (SEQ ID NO:52) and (SEQ ID NO:53); for the −100+1 construct (SEQ ID NO:54) and (SEQ ID NO:55); for the −50+1 construct (SEQ ID NO:56) and (SEQ ID NO:57); for the −200+125 construct (SEQ ID NO:58) and (SEQ ID NO:59); for the −200+71 construct (SEQ ID NO:60) and (SEQ ID NO:61); and for the −200+50 construct (SEQ ID NO:62) and (SEQ ID NO:63).

The following deletion constructs were tested for luciferase activity with the results in parentheses presented as % of the −200+1 control: −6000+1 (38%), −4000+1 (31%), −2000+1 (45%), −400+1 (93%), −300+1 (100%), −200+1 (100%), −150+1 (109%), −100+1 (62%), −50+1 (28%), −2000+1100 (100%), −200+1100 (459%), +1+1100 (114%), −200+200 (562%), −200+150 (474%), −200+125 (314%), −200+100 (168%), −200+71 (153%) −200+50 (87%) and basic promoter construct (5%).

The results of transient transfection assays in the AR+ cell line LNCaP illustrate a repressor, and multiple activator sites at nucleotides −150 to −100 (homopurine stretch), −100 to −50 (SP1 site), and −50 to +1 (helix loop helix binding site).

The results indicate that: (1) the untranslated region (UTR) from +1 to +1100 contains two critical regions for optimal activity, sites between +125 and +100 and between +71 and +50; (2) a repressor site may exist between −2000 and −400; and (3) the activity of the proximal promoter region is derived from sequences between −150 and −100 (approximately 2-fold) and between −100 and −50 (an additional 2–3 fold) and −50 to +1 (an additional 4–5 fold).

Additional site specific mutants were generated as follows: delta HP, a 40 bp internal deletion of the homopurine stretch, delta HP (5'), delta HP (3'), HLH-us, SPI, HLH-ds, the 3'10 bp of HLH-ds (HLH-3), the 5'10 bp of HLH-ds (HLH-5) and a double mutant of delta HP and HLH-ds (delta HP/HLH-ds) all in the context of the 200+1 construct. The results of transient transfection studies in LNCaP cells expressed as % of the −200+1 control are presented in Table 19.

TABLE 19

Luciferase activity of Promoter constructs

| Promoter Construct | Luciferase Expression (% of control) |
| --- | --- |
| −200 +1 (control) | 100 |
| delta HP | 40 |
| delta HP (5') | 41 |
| delta HP (3') | 89 |

TABLE 19-continued

Luciferase activity of Promoter constructs

| Promoter Construct | Luciferase Expression (% of control) |
| --- | --- |
| HLH-ds | 63 |
| delta HP/HLH-ds | 40 |
| HLH-us | 88 |
| SP1 | 111 |
| HLH-3 | 42 |
| HLH-5 | 136 |

These results suggest that: (1) the 5' portion of the homopurine region represents all of the activity from −150 to −100; (2) the region 3' of the downstream helix-loop-helix sequence contains another 2-fold of activity; and (3) the downstream helix-turn-helix site contains 1.5-fold activity.

Of particular interest are the HLH-ds and HLH-3 deletion mutants and the 5' HP mutant, which resulted in a significant decrease in luciferase activity indicating the presence of an activator site. The corresponding wild type sequences for these mutants are presented as SEQ ID NO: 64, SEQ ID NO:65 and SEQ ID NO:66, respectively.

EXAMPLE 6

Her2

A 2000-bp fragment of the human Her2 promoter (FIG. 9, SEQ ID NO:67) was PCR amplified from genomic DNA using the following oligonucleotides:

```
5'-GCA CGC GTA AGC TTC AGG CCC CAC AAA ACC TA-3'    (SEQ ID NO:68) and
5'-CGC TCG AGC CAT GGC TCC GGC TGG ACC CGG CTG GG-3' (SEQ ID NO:69).
```

This purified fragment was subcloned into the vector pGL3-basic (Promega) at the NcoI and HindIII sites for use in transient transfection assays in breast carcinoma cell lines MCF-7 (low HER2 expression) and MDA-MB-453 (high HER2 expression).

In addition, several deletion constructs were made in a Her2 luciferase reporter containing a 2 kb promoter fragment cloned into pGL3-Basic. The reporters were transiently transfected into the MCF7 and ZR75 cell lines. Table 20 shows the reporter activity for each promoter construct with the modified sequence portion indicated as underlined. The results indicate that the critical regulatory sites for the Her2 promoter lie between nucleotides −125 and −50.

TABLE 20

Luciferase Reporter Activity of Various Her2 Promoter Constructs in MCF7 and ZR75 Cells

| Construct | Sequence (modification presented as underlined) | % Wild Type Activity (MCF7/ZR75) |
| --- | --- | --- |
| Her2 wild type | GAGCTGGGAGCGCGCTTGCTCCCAATCACCGGAGAAGGA (SEQ ID NO:211) | 100/100 |
| 100 to 85 | GATGGATCCTATATACCGCTCCCAATCACCGGAGAAGGA (SEQ ID NO:212) | 22/33 |
| 80 to 65 | GAGCTGGGAGCGCGCTTGCTCCAGGATCCATTCACCTGA (SEQ ID NO:213) | 30/29 |

TABLE 20-continued

Luciferase Reporter Activity of Various Her2 Promoter Constructs in MCF7 and ZR75 Cells

| Construct | Sequence (modification presented as underlined) | % Wild Type Activity (MCF7/ZR75) |
|---|---|---|
| 90 to 75 | GAGCTGGGAGCGATGGATCCAAACCGAACCGGAGAAGGA (SEQ ID NO:214) | 9/12 |
| 87 to 79 | GAGCTGGGAGCGCGCGGATCCAATATCACCGGAGAAGGA (SEQ ID NO:215) | 16/12 |
| 84 to 76 | GAGCTGGGAGCGCGCTTGAGGATCCGAACCGGAGAAGGA (SEQ ID NO:216) | 18/23 |
| 84 to 78 | GAGCTGGGAGCGCGCTTTAGATCTATCACCGGAGAAGGA (SEQ ID NO:217) | /17 |
| 81 to 76 | GAGCTGGGAGCGCGCTAAGCTTCAATCACCGGAGAAGGA (SEQ ID NO:218) | /23 |
| 90 to 82 | GAGCTGGGAGCAATGGATCCACCAATCACCGGAGAAGGA (SEQ ID NO:219) | 505/434 |
| 84 to 81 | GAGCTGGGAGCGCGCTTTAGACCAATCACCGGAGAAGGA (SEQ ID NO:220) | 306/297 |
| 93 to 85 | GAGCTGGGATAGGATCCTCTCCCAATCACCGGAGAAGGA (SEQ ID NO:221) | 41/62 |
| 81 to 73 | GAGCTGGGAGCGCGCTTGCTCAAGGATCCAGAGGAAGGA (SEQ ID NO:222) | 70/71 |
| 93 to 88 | GAGCGGATCCCGCGCTTGCTCCCAATCACCGGAGAAGGA (SEQ ID NO:223) | /46 |
| 87 to 82 | GAGCTGGGAGGGATCCTGCTCCCAATCACCGGAGAAGGA (SEQ ID NO:224) | /72 |
| 75 to 70 | GAGCTGGGAGCGCGCTTGCTCCAAGCTTCCGGAGAAGGA (SEQ ID NO:225) | /132 |
| 75 to 70 | GAGCTGGGAGCGCGCTTGCTCCGGATCCCCGGAGAAGGA (SEQ ID NO:226) | 60/60 |

To further delineate the critical site(s), a series of linker scanner Her2 luciferase reporter mutants was made from nucleotides −130 through −55. The constructs designated 10085, 9075, 8065, and 7055 (indicating the bases mutated; e.g., 10085 indicates that bases from −100 through −85 were mutated, etc.) were tested in transient transfections in ZR75 and MCF7 cells with the results presented in Table 23 as % activity relative to the wild type promoter.

The results clearly implicate the −90 to −75 region as critical to the activity of the Her2 promoter.

Mutations were made in various regions of the Her2 promoter, including an AT-rich region around and including a putative TATA box (TB, "TATAAGA"), a putative TATA box (T5B, CTTGAGGAAGG<u>ATCC</u>GAATGAAGTTGT, SEQ ID NO:227), an AT stretch downstream of the putative TATA box (T3B, CTTGAGGAAGTATAA<u>TCC</u>GGAAGTTGT, SEQ ID NO:228), a putative ets site (EP), a double mutant of the AT-rich region around and including the putative TATA box (TATA/Ets, CTT<u>TCGATCGGATCCGCC</u>GGAAGTTGT, SEQ ID NO:229), and the putative ets site (TBEP, "GAGGAA") as well as a deletion to −215. Sequence modifications are indicated as underlined.

Luciferase reporter constructs were prepared with the various Her2 promoter sequences immediately upstream of the reporter coding sequence. The reporters were transiently transfected into MCF7 and ZR75 cells and the resulting luciferase expression reported as the % of wild type (Table 21).

TABLE 21

Luciferase Reporter Activity of Various Her2 Promoter Constructs

| Promoter Construct | % WT Activity MCF7 cells | % WT Activity ZR75 cells |
|---|---|---|
| Basic | 3.3 | 2.1 |
| Wild type | 100 | 100 |
| −215 | 143 | 195 |
| TB | 796 | 432 |
| T5B (TATA) | 64 | 44 |
| T3B | 521 | 351 |
| EP (ets) | 69 | 62 |
| TBEP | 843 | 449 |

The data suggest that sequences upstream of nucleotide −215 are not critical for regulation. As shown in Table 21, mutating the TATA box or the ets site causes a modest decrease in transcription, suggesting that a repressor site lies just downstream of the TATA box. The sequence near the putative TATA box and putative ets site is shown below.

```
CTGCTTGAGGAAGTATAAGAATGAAGTTGT       (SEQ ID NO:230)
     ets   TATA box
```

An additional deletion construct, −50, was made in a Her2 reporter containing a 2 kb promoter fragment cloned into pGL3-Basic and compared to the −215 deletion. The reporters were transiently transfected into MCF7 and ZR75 cells line. The results indicate that critical regulatory sites for the Her2 promoter lie in the −215 to −50 region.

Several additional deletion constructs were made in a Her2 luciferase reporter containing a 2 kb promoter fragment cloned into pGL3-Basic. The reporters were transiently transfected into MCF7 and ZR75 cells line. The results presented in Table 22 (expressed as % wild type luciferase activity), indicate that the region of the Her2 promoter between −125 and −50 contains critical regulatory sites.

TABLE 22

Luciferase Reporter Activity of HER2 Deletion Constructs

| Her2 promoter construct | MCF7 cells | ZR75 cells |
|---|---|---|
| Basic | 6.1 | 4.1 |
| Wild type | 100 | 100 |
| deletion of 5' end to −215 | 215 | 167 |
| deletion of 5' end to −150 | 58 | 41 |
| deletion of 5' end to −125 | 65 | 40 |
| deletion of 5' end to −100 | 27 | 16 |
| deletion of 5' end to −50 | 4.8 | 3.7 |

Further experiments were carried out to determine if the sequences identified as important in ZR-75 and MCF-7 cells are also important in other breast cancer cell lines. Two cell lines SKBR-3 (SK) and BT-474 (BT), were selected which overexpress Her2 at higher levels than do either ZR-75 or MCF-7 cells. A summary of the data from 3 transient transfections is presented below in Table 23, together with the results of parallel studies done in ZR-75 cells (ZR).

TABLE 23

Luciferase Reporter Activity of Her2 Mutants in BT-474 and SKBR-3 Cells

| | Transfection 1 | | | Transfection 2 | | | Transfection 3 | | |
|---|---|---|---|---|---|---|---|---|---|
| Reporter | SK | BT | ZR | SK | BT | SK | BT | ZR |
| Her2 WT | 100 | 100 | 100 | 100 | 100 | 100 | 100 | 100 |
| Basic | 0.8 | 3.2 | 2.0 | 0.6 | 2.8 | 0.5 | 3.5 | 2.1 |
| 9082-1 | 150 | 293 | 416 | 269 | 243 | 177 | 296 | 337 |
| 8481-3 | 295 | 286 | 406 | 159 | 220 | 197 | 251 | 305 |
| TATAB-3 | 446 | 1014 | 881 | 733 | 961 | 500 | 718 | 608 |
| 8478-10 | 49 | 40 | 19.5 | 41 | 52 | 23 | 52 | 27 |
| CATb-21 | 27 | 69 | 52 | 25 | 76 | 20 | 72 | 59 |
| 9075-8 | | 10 | 30 | 10 | 9 | 39 | | |
| −50-3 | 3 | 6 | 4 | 2 | 7.5 | | | |
| −100-3 | 10 | 21 | 21 | 9 | 25 | | | |
| −150-10 | 19 | 45 | 48 | 16 | 51 | | | |

The comparative results of luciferase expression assays in the 3 cell lines suggest the following: (1) the Her2 promoter is 4–5 fold stronger in SKBR-3 cells than in BT-474 cells and 3–4 fold stronger than in ZR75-1 cells; (2) the TATA-Bam mutation results in less up-regulation in SKBR-3 cells than in the other two cell lines; (3) the CCAAT box is more important in SKBR-3 (4–5 fold decrease) than in either ZR75-1 (2-fold down) or BT-474 (less than 2-fold down) cells and (4) the CCAAT box may be an appropriate target for regulation of Her2.

Based on the results provided above, sequences of interest for regulated expression of Her2 are a repressor sequence "GAATGAAGTT" (SEQ ID NO:70) downstream of the putative TATA box at −23 to −19; the complex regulatory region "CGCTTGCTCCCAATC" (SEQ ID NO:71), which has both activator and repressor components and the TATA box/ets site, "GAGGAAGGTATAA" (SEQ ID NO:72), wherein the ets sequence is "GAGGAAG" and the TATA box sequence is "TATAA".

EXAMPLE 7

Beta-lactamase (Bla) Promoter

The natural beta-lactamase promoter P3 (SEQ ID NO:73), shown below, lies near the coding sequence of beta-lactamase (bla), initiating transcription at 35 bases 5' to the ATG translation initiation codon. The P3 promoter contains a Pribnow box (GACAATA) at the −10 region and a −35 consensus sequence, TTCAAA. The −35, −10, start site and ribosome binding site, respectively in the 5' to 3' order, are indicated as underlined, below.

GACGTCAGGTGGCACTTTTCGGGGAAAT-GTGCGCGGAACCCCTATTTGTTTATTTTT CTAATACA<u>TTCAAA</u>TATGTATCCGCTCATGA <u>GACAATA</u>ACCCTGATAAATGCTTCAATA ATA TTGAAAA<u>AGGA</u>AGAGT (natural beta-lactamase promoter P3, SEQ ID NO:73)

Renilla luciferase reporter constructs were prepared in the pACYC177 vector, wherein the wild type beta-lactamase promoter driven Renilla luciferase construct was designated pBla-rluc. The control promoter-less construct was designated pNull-rluc, and the luciferase negative construct designated pBla-bla.

Bla promoter mutants (designated "M#") of the natural P3 bla promoter were generated by systematically altering the base pairs of the entire bla promoter sequence (from nucleotides −101 to +43). In general, mutants were generated by introducing 6 to 12 base pair mutations at different locations of entire Bla promoter by Quick Change, by replacing purines with pyrimidines and vice versa and incorporating restriction sites in the sequence.

Luciferase activities of various Bla mutants were measured in lysates prepared from E. coli XL1 Blue replicates and compared to that of wild type pBla-rluc. Mutants which exhibited significantly decreased luciferase activity include the −35 region (−41 to −30, M6); the −10 region (−17 to −6, M8); the start site (−5 to +7, M9); and +20 to +31 (M11) which exhibited luciferase activities which were reduced to 24%, 29%, 15% and 2% of wild type, respectively, as shown in Table 24, below.

TABLE 24

Sequences of Bla Promoter Mutants and Luciferase Reporter Activity

| Mutant | Location | Wild Type Sequence | Mutated Sequence | Luciferase Activity (% Wild Type) |
|---|---|---|---|---|
| M6 | −41 to −30 | AATACATTCAAA (SEQ ID NO:75) | CCGGCCGGACCC (SEQ ID NO:231) | 24% |
| M21 | −35 to −30 | TTCAAA | GGACCC | 28% |
| M8 | −17 to −6 | CATGAGACAATA (SEQ ID NO:76) | ACGCGTCACCGC (SEQ ID NO:232) | 29% |
| M30 | −8 to −3 | TAACC | CGCCAA | 24% |
| M9 | −5 to +7 | ACCCTGATAAAT (SEQ ID NO:77) | CAAAGTCGACCG (SEQ ID NO:233) | 15% |
| M11 | +20 to +31 | TTGAAAAGGAA (SEQ ID NO:78) | GGGCCCCCTTCC (SEQ ID NO:234) | 2% |

Luciferase activity of mutants M6 (−41 to −30; SEQ ID NO:75) and M21 (−35 to −30) revealed that the −35 region is critical to promoter activity, as indicated by a reduction in luciferase activity to 24% and 28%, respectively. Luciferase activity of mutant M8 (−17 to −6; SEQ ID NO:76) and M30 (−8 to −3) revealed that the −10 pribnow box region is also critical, as indicated by a reduction in luciferase activity to 29% or 24%. Two additional regions important for luciferase activity are the start region (M9; SEQ ID NO:77) and the ribosome binding site region (M11; SEQ ID NO:78), as indicated by a reduction in luciferase activity to 15% and 2%, respectively.

The sequence of the −101 to +35 region of a modified BlaMT promoter (SEQ ID NO:74) is presented below with lower case letters indicating mutations relative to the natural P3 Bla promoter sequence.

GACGTCAGGTGGCACTTTTCGGGGAAAT-GTGCGCGGAACCCCTATcTGTTTgTTCTTc TAgAcACATTCAcAcATGTATCCGCTCAT-GAGACAATAACCCTGATAAATGCTTCAATgAcATTGAgAAAGGAAGAGT (modified BlaMT promoter, SEQ ID NO:74)

TABLE 25

Sequences of pBlaMT and Mutant pBlaMT Constructs

| Mutants | Sequence(−35 to +7 of BlaMT promoter) |
|---|---|
| PblaMT | TTCACACATGTATCCGCTCATGAGACAATAACCCTGATAAAT (SEQ ID NO:235) |
| pBlaMT(−35) | TTtAaAtATGTATCCGCTCATGAGACAATAACCCTGATAAAT (SEQ ID NO:236) |
| pBlaMT(−10) | TTCACACATGTATCCGCTCATGAGAtAATAAttCTGATAAAT (SEQ ID NO:237) |
| pBlaMT(−10p) | TTCACACATGTATCCGCTCATGAGACAATAACCCTGATgAAT (SEQ ID NO:238) |
| pBlaMT(−10/+1) | TTCACACATGTATCCGCTCATGAGACAATAAtttTGAcgAAT (SEQ ID NO:239) |
| pBlaMT (+1) | TTCACACATGTATCCGCTCATGAGACAATAACttTtATAAAT (SEQ ID NO:240) |

Table 25 depicts the location and sequence of various mutant BlaMT promoter constructs. Lower case letters indicate the mutations relative to the pBlaMT sequence and underlined sequences indicate the location of potential compound binding sites. As detailed in co-owned PCT Publication No. WO 00/52179 (expressly incorporated by reference herein), when a sequence immediately downstream of the start site in various pBlaMT mutant constructs [e.g., pBlaMT, pBlaMT(+1), pBlaMT(−35) and pBlaMT(−10)] was targeted by a DNA binding compound, the activity of each promoter was up-regulated.

The data presented herein provides an analysis of the regulatory regions of various promoters and shows that once the regulatory region of a promoter is identified, it can be targeted by both cellular factors (native or exogenously provided) and by compounds in order to effect regulated expression of a coding sequence operably linked thereto.

TABLE 26

Sequence Listing Table

| DESCRIPTION | SEQ ID NO |
|---|---|
| cyclin D1 promoter −1745 to +155 (wild-type, FIG. 4) | 1 |
| cyclin D1 primer for PCR amplification of promoter from genomic DNA 5'-GCA CGC GTG CTA GCC AGC TGG GCC GCC CTT GT-3' | 2 |
| cyclin D1 primer for PCR amplification of promoter from genomic DNA 5'-ATC CAT GGA AGC TTT GGG GCT CTT CCT GGG CA-3' | 3 |
| cyclin D1 Primer for PCR cloning of 5' deletions: 5'-GCA CGC GTG CTA GCT GGA GCC TCC AGA GGG CTG T-3' | 4 |
| cyclin D1 −30-21 wild type sequence: GAGTTTTGTT | 5 |
| cyclin D1 −30-24 wild type sequence: GAGTTTT | 6 |
| cyclin D1 CRE wild type sequence: CAGTAACGTCACACGG | 7 |
| cyclin D1 (+1 to +9) wild type sequence: CCTCCAGAGG | 8 |
| CD40L promoter (human, full-length) −1860 to +49 (FIGS. 5A–C) | 9 |

TABLE 26-continued

Sequence Listing Table

| DESCRIPTION | SEQ ID NO |
|---|---|
| CD40L, D1 primer for PCR amplification of promoter from genomic DNA 5'-TTA TGA TAC CTC GAG GGG AGA GCA TTC AGG AAG ATG-3' | 10 |
| CD40L, D1 primer for PCR amplification of promoter from genomic DNA 5'-TGA ATC ACG AAG CTT TGG TAT CTT CTG CCA GAG AAG-3' | 11 |
| CD40L site between -320 and -297: GAT GAA TTT GTC ACT TTC CTT GAA | 12 |
| CD40L site between -230 and -211: GAC ATT TCA AGG CAA GAA TG | 13 |
| CD40L site between -230 and -196: ACA TTT CAA GGC AAG AAT GAA TAT ATG GAA GAA GA | 14 |
| CD40L site between -77 and -40: TACGA AGCACATTTTCCAGGAAGTGTGGGCTGCAACG | 15 |
| HBV core promoter sequence (FIG. 1A) | 16 |
| HBV core promoter proximal, HNF3-2 site: GACTGTTTGTTT | 17 |
| HBV core promoter HNF4 transcription factor binding site: AGGACTCTTGGA | 18 |
| HBV core promoter domain 8 wild type sequence: TACTTCAAAGACTGT | 19 |
| HBV core promoter domain 8 and 9-1 wild type sequence: TACTTCAAAGACTGTTTGTTTAA | 20 |
| HBV core promoter domain 13 wild type sequence: GGCTGTAGGCATAAA | 21 |
| HBV pre-S1 promoter sequence (FIG. 1B) | 22 |
| HBV pre-S1 promoter domain 2 wild type sequence: CTA GTT AAT CAT TAC | 23 |
| HBV pre-S1 promoter domain 6 wild type sequence: TTA TAT AAG AGA GAA | 24 |
| HBV-X promoter sequence (FIG. 3) | 25 |
| HBV-X promoter domain 3 wild type sequence: TGTAAACAATACCTGAACCTT | 26 |
| HBV-X promoter domain 6 wild type sequence GCTGACGCAACCCCCACTGGC | 28 |
| Forward primer for construction of XpLuc200 CACCGAAGCTTAAGCAGGCTTTCACTTTCTCG | 29 |
| Reverse primer for construction of XpLuc200 CAGTACCGGAATGCCAAGCTTCGATG | 30 |
| vanH promoter sequence (FIG. 6) GAGATGTATATAATTTTTTAGGAAAATCTCAAGGTTATCTTTACTTTTTCTTAGG AAATTAACAATTTAATATTAAGAAACGGCTCGTTCTTACACGGTAGACTTAATAC CGTAAGAACGAGCCGTTTTCGTTCTTCAGAGAAAGATTTGACAAGATTACCATT GGCATCCCCGTTTTATTTGGTGCCTTTCACAGAAAGGGTTGGTCTTAATT | 31 |
| vanH wild type promoter sequence corresponding to M6: TTAGGAAATT | 32 |
| vanH wild type promoter sequence corresponding to M8: TATTAAGAAA | 33 |
| vanH wild type promoter sequence corresponding to M12: CGTAAGAACG | 34 |
| Androgen receptor (AR) promoter sequence from -6000 to +1100 (FIGS. 8A–C) | 35 |
| AR: forward PCR primer for construction of -6000+1 deletion construct CACGCGTGGTACCTCTAGAAAATAATTCCCAATATTGAATCCC | 36 |
| AR: reverse PCR primer for construction of -6000+1 deletion construct AGCTGGCTCCCCGGGATCTCGGAGGGGCGC | 37 |
| AR: forward PCR primer for construction of -4000+1 deletion construct CACGCGTGGTACCAGACAGTGACAGGACTTAAACGGGGAAAT | 38 |
| AR: reverse PCR primer for construction of -4000+1 deletion construct AGCTGGCTCCCCGGGA | 39 |
| AR: forward PCR primer for construction of -2000+1 deletion construct CACGCGTGGTACCTATACACATTATGTCTTTTAAATGAC | 40 |
| AR: reverse PCR primer for construction of -2000+1 deletion construct AGCTGGCTCCCCGGGATCTCGGAGGGGCGC | 41 |
| AR: forward PCR primer for construction of -2000+1100 deletion construct CACGCGTGGTACCTATACACATTATGTCTTTTAAATGAC | 42 |
| AR: reverse PCR primer for construction of -2000+1100 deletion construct CCGCCATGGTGAGCTTGGCTGAATCTTCCA | 43 |
| AR: forward PCR primer for construction of -200+1 deletion construct CCGGGTACCTGCCCTCGCCCACGCTGCGCC | 44 |
| AR: reverse PCR primer for construction of -200+1 deletion construct AGCTGGCTCCCCGGGATCTCGGAGGGGCGC | 45 |
| AR: forward PCR primer for construction of -200+100 deletion construct CCGGGTACCTGCCCTCGCCCACGCTGCGCC | 46 |
| AR: reverse PCR primer for construction of -200+100 deletion construct AGCTGGCTCCCCGGGATCTCGGAGGGGCGC | 47 |
| AR: forward PCR primer for construction of -400+1 deletion construct: CAGAACATTTCTCTATCGATAGGTACCGAGCAGGTATTCCTATCGTCCTTTTCC | 48 |
| AR: reverse PCR primer for construction of -400+1 deletion construct: GGAAAAGGACGATAGGAATACCTGCTCGGTACCTATCGATAGAGAAATGTTCTG | 49 |
| AR: forward PCR primer for construction of -300+1 deletion construct: CAGAACATTTCTCTATCGATAGGTACCAAATCTGGAGCCCTGGCGCCTAAACCT | 50 |
| AR: reverse PCR primer for construction of -300+1 deletion construct: AGGTTTAGGCGCCAGGGCTGCAGATTTGGTACCTATCGATAGAGAAATGTTCTG | 51 |
| AR: forward PCR primer for construction of -150+1 deletion construct: CAGAACATTTCTCTATCGATAGGTACCGGCGTTAGCGCGCGGTGAGGGGAG | 52 |
| AR: forward PCR primer for construction of -100+1 deletion construct: | |

TABLE 26-continued

Sequence Listing Table

| DESCRIPTION | SEQ ID NO |
|---|---|
| CAGAACATTTCTCTATCGATAGGTACCGGGAAAAGGAGGTGGGAAGGCAAGG AGGCC | |
| AR: reverse PCR primer for construction of -100+1 deletion construct: GGCCTCCTTGCCTTCCCACCTCCTTTTCCCGGTACCTATCGATAGAGAAATGT TCTG | 55 |
| AR: forward PCR primer for construction of -50+1 deletion construct: CAGAACATTTCTCTATCGATAGGTACCCTCGCAAACTGTTGCATTTGCTCTCC ACCTCCC | 56 |
| AR: reverse PCR primer for construction of -50+1 deletion construct: GGGAGGTGGAGAGCAAATGCAACAGTTTGCGAGGGTACCTATCGATAGAGAA ATGTTCTG | 57 |
| AR: forward PCR primer for construction of -200+125 deletion construct: CCAGTGCTGTACAGGAGCCGAAGGGACGCACCCCATGGAAGACGCCAAAAA CATAAAGAAAGGCC | 58 |
| AR: reverse PCR primer for construction of -200+125 deletion construct: CCTTTCTTTATGTTTTTGGCGTCTTCCATGGGGTGCGTCCCTTCGGCTCCTGT ACAGCACTGG | 59 |
| AR: forward PCR primer for construction of -200+71 deletion construct: CCACAGGCAGAGGAGGCGACAGAGGGCCATGGAAGACGCCAAAAACATAAA GAAAGGCC | 60 |
| AR: reverse PCR primer for construction of -200+71 deletion construct: CCTTTCTTTATGTTTTTGGCGTCTTCCATGGCCCTCTGTCGCCTCCTCTGCCT GTGG | 61 |
| AR: forward PCR primer for construction of -200+50 deletion construct: GGGAGAGCGGGACGGTCCGGAGCAAGCCCACCATGGAAGACGCCAAAAACA TAAAGAAAGGCC | 62 |
| AR: reverse PCR primer for construction of -200+50 deletion construct: GGCCTTTCTTTATGTTTTTGGCGTCTTCCATGGTGGGCTTGCTCCGGACCGTC CCGCTCTCCC | 63 |
| AR wild type HLH-ds sequence: TGTTGCATTTGCTCTCC | 64 |
| AR wild type HLH-3 sequence: GCTCTCCACCTCCCAG | 65 |
| AR wild type 5' HP sequence: GGTGAGGGGAGGGGAGAAAAGGAAA | 66 |
| Her2 promoter sequence (FIG. 9) | 67 |
| PCR primer for amplification of a 2000-bp fragment of the human Her2 promoter 5'-GCA CGC GTA AGC TTC AGG CCC CAC AAA ACC TA-3' | 68 |
| PCR primer for amplification of a 2000-bp fragment of the human Her2 promoter 5'-CGC TCG AGC CAT GGC TCG GCT GGA GCG GGT GG-3' | 69 |
| Her2 wild type repressor sequence downstream of the putative TATA box: GAATGAAGTT | 70 |
| Her2 wild type complex regulatory region: CGCTTGGTCCCAATC | 71 |
| Her2 wild type TATA box/ets site: GAGGAAGGTATAA | 72 |
| natural beta-lactamase promoter P3 GACGTCAGGTGGCACTTTTCGGGGAAATGTGCGCGGAACCCCTATTTGTTTA TTTTTCTAATACATTCAAATATGTATCCGCTCATGAACAATAACCCTGATAAAT GCTTCAATAATA TTGAAAAAGGAAGAGT | 73 |
| modified beta-lactamase promoter (BlaMT) promoter: GACGTCAGGTGGCACTTTTCGGGGAAATGTGCGCGGAACCCCTATcTGTTTgT TCTTcTAgAcACATTCAcAcATGTATCCGCTCATGAGACAATAACCCTGATAAAT GCTTCAATgAcATTGAgAAAGGAAGAGT | 74 |
| beta-lactamase promoter wild type sequence for the -35 region (-41 to -30, M6): AATACATTCAAA | 75 |
| beta-lactamase promoter wild type sequence for the -10 region (-17 to -6, M8): CATGAGACAATA | 76 |
| beta-lactamase promoter wild type sequence for the start site (-5 to +7, M9): ACCCTGATAAAT | 77 |
| beta-lactamase promoter wild type sequence for the +20 to +31 site (M11): TTGAAAAAGGAA | 78 |

It is claimed:

1. An isolated nucleic acid regulatory sequence for a cyclin D1 promoter, said regulatory sequence represented by SEQ ID NO:5 and characterized by the ability to regulate expression of a gene operably linked to a cyclin D1 promoter containing said regulatory sequence.

* * * * *

SEQUENCE LISTING

<160> NUMBER OF SEQ ID NOS: 78

<210> SEQ ID NO 1
<211> LENGTH: 1903
<212> TYPE: DNA
<213> ORGANISM: Homo sapiens

<400> SEQUENCE: 1

```
cagctgggcc gcccttgtgc gcgggctgat gctctgaggc ttggctatgc gggggccaac        60
gcgattgtgg gtgctcgggg agtgggggggg ggcacgaccg taggtgctcc ctgctgggcc      120
aacccatcgc tccccatgcg gaatccgggg gtaattaccc ccccaggacc cggaatatta       180
gtaatcctaa ttcccggcgg gggagggggc gcgggaggaa ttcaccctga aggtgggggg       240
tgggggggggt cgcatcttgc tgtgagcacc ctggcgaagg ggagagggct ttttctatca      300
gttttctttg agcttttact gttaagaggg tacggtggtt tgatgacact gaactatatt      360
caaaaggaag taaatgaaca gttttcttaa tttgggcag gtactgtaaa aataaaaaca        420
aaagttaaga cagtaaaatg tcctttatt ttttaatgca ccaaagagac agaacctgta        480
atttttaaaaa ctgtgtatt taatttacat ctgcttaagt ttgcgataat attggggacc      540
ctctcatgta accacgaaca cctatcgatt ttgctaaaaa tcagatcagt acactcgttt      600
gtttaattga taattgttct gaattatgcc ggctcctgcc agcccctca cgctcacgaa        660
ttcagtccca gggcaaattc taaaggtgaa gggacgtcta cacccccaac aaaaccaatt      720
aggaacttcg gtggtcttgt cccaggcaga ggggactaat atttccagca atttaatttc      780
ttttttaatt aaaaaaaatg agtcagaatg gagatcactg tttctcagct ttccattcag      840
aggtgtgttt ctcccggtta aattgccggc acgggaaggg aggggtgca gttgggacc         900
cccgcaagga ccgactggtc aaggtaggaa ggcagcccga agagtctcca ggctagaagg      960
acaagatgaa ggaaatgctg gccaccatct tgggctgctg ctggaatttt cgggcattta     1020
ttttatttta ttttttgagc gagcgcatgc taagctgaaa tcccttaac ttttagggtt      1080
accccctggg gcatttgcaa cgacgcccct gtgcgccgga atgaaacttg cacagggggtt    1140
gtgtgcccgg tcctccccgt ccttgcatgc taaattagtt cttgcaattt acacgtgtta     1200
atgaaaatga aagaagatgc agtcgctgag attctttggc cgtctgtccg cccgtgggtg     1260
ccctcgtggc gttcttggaa atgcgcccat tctgccggct tggatatggg gtgtcgccgc     1320
gccccagtca ccccttctcg tggtctcccc aggctgcgtg ctgtgccggc cttcctagtt     1380
gtcccctact gcagagccac ctccacctca cccctaaat cccgggggac ccactcgagg      1440
cggacgggggc cccctgcacc cctcttccct ggcggggaga aaggctgcag cggggcgatt     1500
tgcatttcta tgaaaaccgg actacagggg caactccgcc gcagggcagg cgcggcgcct     1560
cagggatggc ttttgggctc tgcccctcgc tgctcccggc gtttggcgcc gcgccccct      1620
cccctgcgc ccgccccgc ccccctcccg ctcccattct ctgccgggct ttgatctttg      1680
cttaacaaca gtaacgtcac acggactaca ggggagtttt gttgaagttg caaagtcctg     1740
gagcctccag agggctgtcg gcgcagtagc agcgagcagc agagtccgca cgctccggcg     1800
aggggcagaa gagcgcgagg gagcgcgggg cagcagaagc gagagccgag cgcggaccca     1860
gccaggaccc acagccctcc ccagctgccc aggaagagcc cca                       1903
```

<210> SEQ ID NO 2
<211> LENGTH: 32
<212> TYPE: DNA
<213> ORGANISM: Artificial Sequence
<220> FEATURE:
<223> OTHER INFORMATION: primer

<400> SEQUENCE: 2

```
gcacgcgtgc tagccagctg ggccgcccctt gt                                     32
```

```
<210> SEQ ID NO 3
<211> LENGTH: 32
<212> TYPE: DNA
<213> ORGANISM: Artificial Sequence
<220> FEATURE:
<223> OTHER INFORMATION: primer

<400> SEQUENCE: 3
atccatggaa gctttggggc tcttcctggg ca                              32

<210> SEQ ID NO 4
<211> LENGTH: 34
<212> TYPE: DNA
<213> ORGANISM: Artificial Sequence
<220> FEATURE:
<223> OTHER INFORMATION: primer

<400> SEQUENCE: 4
gcacgcgtgc tagctggagc ctccagaggg ctgt                            34

<210> SEQ ID NO 5
<211> LENGTH: 10
<212> TYPE: DNA
<213> ORGANISM: Homo sapiens

<400> SEQUENCE: 5
gagttttgtt                                                       10

<210> SEQ ID NO 6
<211> LENGTH: 7
<212> TYPE: DNA
<213> ORGANISM: Homo sapiens

<400> SEQUENCE: 6 gagtttt                                                           7

<210> SEQ ID NO 7
<211> LENGTH: 16
<212> TYPE: DNA
<213> ORGANISM: Homo sapiens

<400> SEQUENCE: 7
cagtaacgtc acacgg                                                16

<210> SEQ ID NO 8
<211> LENGTH: 10
<212> TYPE: DNA
<213> ORGANISM: Homo sapiens

<400> SEQUENCE: 8
cctccagagg                                                       10

<210> SEQ ID NO 9
<211> LENGTH: 2395
<212> TYPE: DNA
<213> ORGANISM: Homo sapiens

<400> SEQUENCE: 9
gaattcactg gggagagcat tcaggaagat gacaacagga taataggtca acagagtaat      60
agagaggtcg ctaaaaataa actctaagaa gtattcagcc aaaactatta ttgagctaat     120
aatggtggga tcaatttcag gggaatattg tgggcagaag tcagactgta ggaggctggg     180
gatcaagaag ttgaggcaag gaggttggac aacaactgtt ttttcaagtt ggtcacgtga     240
```

-continued

```
acaaatctgt gaccttcagc ctcccctccc tcgggtcttg gctgagctga ttgcagggcc      300
cctgcagctc tggcactctc aagttgtata aaactgacag tgcagaagtc cttgagccca      360
ttttggctct catgataatt ttccttcagt ggaactaagg ttacttgtct aagaaccaaa      420
gcctctgact tgactgatca agttcatca cgtgcatcga agccacctac ttggcagatg       480
tagtgaaaag ctacatagat ctgggcccag gacaggatgc tggggcgtgg gaggggaaga     540
aagcaggtgc taactatata gatagcatgc ctatcagagc agttttacg tttcctattt       600
gtctctcaaa acaattttat aggaatcatc aaagcaattt tatcatggtt tctagaccag      660
gtttggatgt gaggtaggga tttccacagc tgcttttagt ttgaaggaaa tctgataaga      720
tgatgcaaaa gcccttcaga aatgtgtaat cctacacact tcagtgattc aattcattgt      780
caaaacttaa ggtgttttta atattgttat tgttcatttg gttttaccaa acatgtaagg      840
agttggcaat tatttgttaa actcatgtct taggctaaat aaattccaaa aaattcagga     900
tgagaattgt ttattgctta acgtgtgtca aatttcttcc atgcacatct ttattagatc     960
ttcacagcaa cctacaggat aagcaagaca ggtgcaagtg cctcctttgg gtatgaggaa     1020
actgaggtct aaagagatga agtgatttgc ccaaggctca tagcaattta ttggtagagc     1080
aaagactaga attctcttaa ctgcagccta ttttccctat tctgaactgt tacatcagca     1140
tcaacaatta tctaatggat tggaacagtg tacacaggca gcttagctac gtcaagtcac     1200
gattttact ttaacttcaa ttccagagtc ttggcctgat ttccctcaag accctactta       1260
tctttggctt tggaaaattt attttttcttg cattatcttt ccagctaaat tttatttaat      1320
aaccatcagc atgcttttt tgctttatgc catgtagact tgacctgaaa acctgccagg        1380
ctttcattga gtttagtgat taagaagta aagttctgag aagcaattag ttgatgggac        1440
accagtcata aaatcaatcc aaacttttgt tgacatgtgt ttctttctcc atataccagg      1500
ttcccgcttc gtattagtaa gattgaaatt gaaataagtc tattgctggt ggatgaattt       1560
gtcactttcc ttgaaactgg tgaacccaaa aagttagaca gtgataggaa aatactgcca      1620
ttgtctgtta agaagtctat gacatttcaa ggcaagaatg aatatatgga agaagaaact     1680
tgtttcttct ttacttacaa aaaggaaagc ctggaagtga atgatatggg tataattaaa     1740
aaaaaaaaa aaaacaaaaa acctttacgt aacgttttgc tgggagagaa gactacgaag      1800
cacattttcc aggaagtgtg ggctgcaacg attgtgcgct cttaactaat cctgagtaag      1860
gtggccactt tgacagtctt ctcatgctgc ctctgccacc ttctctgcca gaagatacca     1920
tttcaacttt aacacagcat gatcgaaaca tacaaccaaa cttctcccg atctgcggcc       1980
actggactgc ccatcagcat gaaaattttt atgtatttac ttactgtttt tcttatcacc      2040
cagatgattg ggtcagcact ttttgctgtg tatcttcata gaaggctgga caaggtaaga     2100
tgaaccacaa gcctttatta actaaatttg gggtccttac taattcatag gttggttcta      2160
cccaaatgat ggatgatggt agaaaccaaa tagaagaatg gtcttgtggc ataatgtttg     2220
ttccctagtc aatgaactct catattcttg tctctggtta ggatcttggg atctggagtc     2280
agactgcctg ggctcaaatc ttggctctgc ccataccatc tctgttatcc tggggcaagt     2340
gcctcagttt ccacatctga gaaatgggga tggtagtggt gtccatttca tagat          2395
```

<210> SEQ ID NO 10
<211> LENGTH: 36
<212> TYPE: DNA
<213> ORGANISM: Artificial Sequence
<220> FEATURE:
<223> OTHER INFORMATION: primer

```
<400> SEQUENCE: 10
ttatgatacc tcgaggggag agcattcagg aagatg                                36

<210> SEQ ID NO 11
<211> LENGTH: 36
<212> TYPE: DNA
<213> ORGANISM: Artificial Sequence
<220> FEATURE:
<223> OTHER INFORMATION: primer

<400> SEQUENCE: 11
tgaatcacga agctttggta tcttctggca gagaag                                36

<210> SEQ ID NO 12
<211> LENGTH: 24
<212> TYPE: DNA
<213> ORGANISM: Homo sapiens

<400> SEQUENCE: 12
gatgaatttg tcactttcct tgaa                                             24

<210> SEQ ID NO 13
<211> LENGTH: 20
<212> TYPE: DNA
<213> ORGANISM: Homo sapiens

<400> SEQUENCE: 13
gacatttcaa ggcaagaatg                                                  20

<210> SEQ ID NO 14
<211> LENGTH: 35
<212> TYPE: DNA
<213> ORGANISM: Homo sapiens

<400> SEQUENCE: 14
acatttcaag gcaagaatga atatatggaa gaaga                                 35

<210> SEQ ID NO 15
<211> LENGTH: 37
<212> TYPE: DNA
<213> ORGANISM: Homo sapiens

<400> SEQUENCE: 15
tacgaagcac attttccagg aagtgtgggc tgcaacg                               37

<210> SEQ ID NO 16
<211> LENGTH: 250
<212> TYPE: DNA
<213> ORGANISM: Hepatitis B virus

<400> SEQUENCE: 16
gcacgtcgca tggagaccac cgtgaacgcc caccaaatat tgcccaaggt cttacataag      60
aggactcttg gactctcagc aatgtcaacg accgaccttg aggcatactt caaagactgt     120
ttgtttaaag actgggagga gttgggggag gagattaggt taaaggtctt tgtactagga     180
ggctgtaggc ataaattggt ctgcgcacca gcaccatgca acttttttcac ctctgcctaa    240 tcatctcttg                                                            250

<210> SEQ ID NO 17
<211> LENGTH: 12
<212> TYPE: DNA
```

```
<213> ORGANISM: Hepatitis B virus

<400> SEQUENCE: 17
gactgtttgt tt                                                          12

<210> SEQ ID NO 18
<211> LENGTH: 12
<212> TYPE: DNA
<213> ORGANISM: Hepatitis B virus

<400> SEQUENCE: 18
aggactcttg ga                                                          12

<210> SEQ ID NO 19
<211> LENGTH: 15
<212> TYPE: DNA
<213> ORGANISM: Hepatitis B virus

<400> SEQUENCE: 19
tacttcaaag actgt                                                       15

<210> SEQ ID NO 20
<211> LENGTH: 23
<212> TYPE: DNA
<213> ORGANISM: Hepatitis B virus

<400> SEQUENCE: 20
tacttcaaag actgtttgtt taa                                              23

<210> SEQ ID NO 21
<211> LENGTH: 15
<212> TYPE: DNA
<213> ORGANISM: Hepatitis B virus

<400> SEQUENCE: 21
ggctgtaggc ataaa                                                       15

<210> SEQ ID NO 22
<211> LENGTH: 156
<212> TYPE: DNA
<213> ORGANISM: Hepatitis B virus

<400> SEQUENCE: 22
ttattatcca gaacatctag ttaatcatta cttccaaact agacactatt tacacactct      60
atggaaggcg ggtatattat ataagagaga acaacacat agcgcctcat tttgtgggtc      120
accatattct tgggaacaag atctacagca tggggc                               156

<210> SEQ ID NO 23
<211> LENGTH: 15
<212> TYPE: DNA
<213> ORGANISM: Hepatitis B virus

<400> SEQUENCE: 23
ctagttaatc attac                                                       15

<210> SEQ ID NO 24
<211> LENGTH: 15
<212> TYPE: DNA
<213> ORGANISM: Hepatitis B virus

<400> SEQUENCE: 24
ttatataaga gagaa                                                       15
```

-continued

<210> SEQ ID NO 25
<211> LENGTH: 306
<212> TYPE: DNA
<213> ORGANISM: Hepatitis B virus

<400> SEQUENCE: 25
ctaagcaggc tttcactttc tcgccaactt acaaggcctt tctgtgtaaa caatacctga      60
acctttaccc cgttgcccgg caacggccag gtctgtgcca agtgtttgct gacgcaaccc     120
ccactggctg gggcttggtc atgggccatc agcgcatgcg tggaaccttt tcggctcctc     180
tgccgatcca tactgcggaa ctcctagccg cttgttttgc tcgcagcagg tctggagcaa     240
acattatcgg gactgataac tctgttgtcc tatcccgcaa atatacatcg tttccatggc     300
tgctag                                                                306

<210> SEQ ID NO 26
<211> LENGTH: 21
<212> TYPE: DNA
<213> ORGANISM: Hepatitis B virus

<400> SEQUENCE: 26
tgtaaacaat acctgaacct t                                                21

<210> SEQ ID NO 27
<211> LENGTH: 21
<212> TYPE: DNA
<213> ORGANISM: Hepatitis B virus

<400> SEQUENCE: 27
taccccgttg cccggcaacg g                                                21

<210> SEQ ID NO 28
<211> LENGTH: 21
<212> TYPE: DNA
<213> ORGANISM: Hepatitis B virus

<400> SEQUENCE: 28
gctgacgcaa cccccactgg c                                                21

<210> SEQ ID NO 29
<211> LENGTH: 32
<212> TYPE: DNA
<213> ORGANISM: Artificial Sequence
<220> FEATURE:
<223> OTHER INFORMATION: primer

<400> SEQUENCE: 29
caccgaagct taagcaggct ttcactttct cg                                    32

<210> SEQ ID NO 30
<211> LENGTH: 26
<212> TYPE: DNA
<213> ORGANISM: Artificial Sequence
<220> FEATURE:
<223> OTHER INFORMATION: primer

<400> SEQUENCE: 30
cagtaccgga atgccaagct tcgatg                                           26

<210> SEQ ID NO 31
<211> LENGTH: 214
<212> TYPE: DNA

<213> ORGANISM: Vancomycin resistant enterococcus

<400> SEQUENCE: 31

| | | | | |
|---|---|---|---|---|
| gagatgtata | taattttta | ggaaaatctc | aaggttatct | ttactttttc | ttaggaaatt | 60 |
| aacaatttaa | tattaagaaa | cggctcgttc | ttacacggta | gacttaatac | cgtaagaacg | 120 |
| agccgttttc | gttcttcaga | gaaagatttg | acaagattac | cattggcatc | cccgttttat | 180 |
| ttggtgcctt | tcacagaaag | ggttggtctt | aatt | | | 214 |

<210> SEQ ID NO 32
<211> LENGTH: 10
<212> TYPE: DNA
<213> ORGANISM: Vancomycin resistant enterococcus

<400> SEQUENCE: 32
ttaggaaatt                                                                10

<210> SEQ ID NO 33
<211> LENGTH: 10
<212> TYPE: DNA
<213> ORGANISM: Vancomycin resistant enterococcus

<400> SEQUENCE: 33
tattaagaaa                                                                10

<210> SEQ ID NO 34
<211> LENGTH: 10
<212> TYPE: DNA
<213> ORGANISM: Vancomycin resistant enterococcus

<400> SEQUENCE: 34
cgtaagaacg                                                                10

<210> SEQ ID NO 35
<211> LENGTH: 6905
<212> TYPE: DNA
<213> ORGANISM: Artificial Sequence
<220> FEATURE:
<223> OTHER INFORMATION: promoter

<400> SEQUENCE: 35

| | | | | | | |
|---|---|---|---|---|---|---|
| tctagaaaat | aattcccaat | attgaatccc | aaagaattca | acatttgggc | tgtcgtttga | 60 |
| aagataagtt | gaatttggtc | atgaaggaag | agaggggga | tacaatttca | gtaaaggta | 120 |
| acagcaaggt | ccaaagacag | tcaggtcttc | agtagtatgg | agtatattca | gagggagcca | 180 |
| agatgtctga | tgtgaactaa | aaagattggt | ggttggtagg | aggaagaggt | gtgagaagag | 240 |
| gctgtaaaga | aaaattgaaa | cttgattgtg | atggacttta | aaggctaggc | tatgggactt | 300 |
| ggacatgaat | ctgcaggcca | gtgtttgcag | actggcgccc | ataactgtct | atcacagcaa | 360 |
| cacagacatg | tgttgtttgg | cctgcagagg | tttggcctgc | atgatgattt | taaaccatct | 420 |
| gaattagtag | ccatcatttt | caaaaatcaa | gagatgccac | attaaaatat | ggaatgctgc | 480 |
| tgttcttgaa | ataatgaaa | catctggaac | attgaggcca | cattcctgac | tgacagcaat | 540 |
| cagttggagc | tgcgtagtga | ctgcccactt | tacatgggc | atctgatccc | tagtcgatta | 600 |
| cagctgccac | cacttccctt | tatctctcta | ataccaagct | cttttcactc | attttttgtta | 660 |
| cttaagagat | atttgggttt | gaaacctctg | atgcaggtaa | ttgagggtta | tagagcagag | 720 |
| gacagatgct | atcagagttg | tcttttaaga | agaaccctc | tgttcttcat | tttgttgaag | 780 |
| atagcctgga | agagggcagc | caggggagaa | gttagggctg | gagctatgag | aaagcataag | 840 |

-continued

```
atgagatgat ggcttcaaca ttgaggacag aaagaatatt gagatgagaa agtagtccat    900
ataagcatct atgcaaagga aatagcagat gtcctcaaat cagcagaggc aacaactctg    960
aaagtttatt cataagcccc tcttttcatc tccaatccag ttcaaatgta attatttaaa   1020
ttgttcttca ctctccttcc tggatcatga atgagctcct taaatgcagg gtccacagtg   1080
tcctattcat cagtgaattc caagtgccta gcacagagcc tggcaaatag taaatgctta   1140
acaaatattc gttcagtgca tgaattggag tgattctcta ctttgcctca taagttgaaa   1200
aaaggtttat tacatacctaa atatgctga atcacaggg catttggcaa ccccccaaaa    1260
ccaaaactcc cagtttggaa acagaatttt aattctgtga aaataaaatc cattcattta   1320
ttcaaaaaat atttattaaa caatgaccat gtccacacca ggctgagtcc taaggattca   1380
atgatgaaca aaaccaaca tgattcctgc tcttaggaaa catacagttc agtgaggaaa    1440
acagattgtg agaagtcctc caacaaatac tgggtgctat taaatatat taaaaggtga    1500
gtgggtgagg gacttgagct agcctaggtg gttcaggaag tcttcctgga tgtgctgata   1560
tgcataggca ttaactagat aaatagagag aaggatgaac caacattgca ggtagaggga   1620
acagaatatg caaggcagg aaggattatg gagtcgttgg aggacctgaa taaaggccca    1680
gtgtaagtgg atctcagaaa acaggaggaa aggtgtatga gatgagatca gagaggcaga   1740
tcatgtgggg tatggttaat gttttggact tttctattaa gagcaatggg gagacagtga   1800
caggacttaa acgggaaat aatatgacca gattaaactt tctaaaaaac cctctatgca    1860
aatatatatt gagagttaat tattgacaaa gattcaaagg caacaaagtg gagagagaat   1920
agtatttca aaaatggtg ccaaaacaat aggacatcta tattaaaagt tgggtatctg     1980
tctacaaaac ttaattcaaa atggatcaca gacctaaatg taaaactgaa agctatacaa   2040
cttctggaag gaaaacacag atgggaatct gtgtgatctt gagtttgaaa atgatttatt   2100
atatctgaca ccataatccg taagttaaca taattcataa gtgaacaaag tgatgaactg   2160
gacttcatca gaatttaaaa tgtttgtgct tcaaaagaca ctggtatgat aatgaagaca   2220
aactacagat aagatattgt tgaatcatat ttctgataaa ggaattgtgg ctcagaatac   2280
ataactctaa accccataa taaattacaa gtagcccaat taaaaaaaa aaagagaaa     2340
aaatttacag tcttcatcaa agaaagtatc aattgtaaaa taagcacatg aaaaatgctc   2400
tgcatcttta ttcatggggg gatgaaataa aaattaaatg ggaaagacac ctctaattag   2460
aatactaaaa ttaaaagac tgaccatacc aagtattggt gaagtggaaa tgtaaaatga   2520
tacaatcaac ttaggtagat gatttggaag tttcttacaa aagtaggtgt atacctaccc   2580
tgtgactcac ccattccatg gctaagtatt tacctgagag aaatgaaaga atacatccat   2640
acaaagatgt ttatacaaat atttatagca gttttatttg tagtagcccc aaactgaaaa   2700
gaacccaaat gtccatcaaa agtgaatgga taaacaaagc gtggtacagc aatgcaatag   2760
aatactactt agcaataaag aagaatgagc tagtgatata cataacagct taaatgtaca   2820
tcaaaggcat tgtgctcagt gaaagatgca agtaaaaaaa aaaagagta catgctgtat    2880
agttccattg acataaaact ctggaaagtg aaaacagtc tatactgaca gaaagcagat    2940
cattggttgc ctgaggagga ggagtatagg agaggtggag ggaaaatgta caaagtggca   3000
caataaaaac ttttggaatc atagatatat tcactatctt gattgagtga tgatttcatg   3060
agtgcacgtg cgtgtgtcaa aaatgatcaa tttatgcaac tttaaatatg tgcagtttat   3120
tgtatatatc aattatacct cagtacggct attaaaaaga aaccctctgg ctgcacaatg   3180
```

-continued

```
cagaactgat tctaggaaag agtggaggga ggatgaccat ttacagtgct ccaggtggaa    3240
gagaacggtg ccttctggaa gtgaactagg ttggcaacaa cagagatgaa ataaatgggc    3300
agatgtgtga gatacttagg aaataaaacc cgatggtcac cattttccaa aggtcagctc    3360
atcctggctt tccagagcaa agagctaggg aagactttat taataaatcc ctcttgaagt    3420
tgcagaggaa gcttatagca gaaacttact ctcaacctga ctaatctgag agaacacctc    3480
tggttccatt tgattactaa aaaactgcaa agaacaggag gagaaagaag aagaaagctg    3540
gtacaaacag tgaacttata taatattaat caataattgt ctcttgttct taaaagcaat    3600
gggaagaaaa tgagatttga gctggaagat cagagttcaa aatccaaata aagtatatgg    3660
ccctaatatg cttatagtag ttaacctttc ctgataatga tataattgtt gacagcacca    3720
tctttaaaat aaaataacat agtaatcctt cagatttgta aagatctttt cctgtttaca    3780
agtttgttct atacacatta tgtcttttaa atgacacact agccttctga gggtaactta    3840
tattggcaac agttttcaga tgtggaaact gtgaagacaa tgttggtgat gtggaagcaa    3900
cataaacttt ggagtctttc agacccaggt ttgaatgtca gactgctttt tattcagagt    3960
aacttcagag cattatttct caccttaatt tttttttcagg cctctttgtg tctatgtgtc    4020
ctcttcactc ctgtccattg tttcttcagt gattttttgcc accttccttc actgttagtg    4080
tgtagacaca tagttctcct ggctctgaga gcctatgtta attccattct accatcctgc    4140
cacggcccac tcaattccta ttgagcaatg ctagttgaaa gttgtggtgg gattaaatgt    4200
tgcaatgagt attcaaatga ggttgaagta tctacgcatt ctacttacat atggtgaggt    4260
atattcaagg aagctgtagc cattaaaatc tcaggaaata attttttcacc tcctcaggtg    4320 aaagggtctt caggcctttg tgttctggaa ggttcattta tagccatttc ccaaaatgaca    4380 atgcgattga tgagtctaga gtctagctca aatagcaatg gactggaaga ctagtttagg    4440
ttttactaat gtggaacata gaacaaatta tgtccttgtt tcagcctgtt catctgtgaa    4500
atagagccta tcatatccag tcttccttgc ctttaggttt gagttacctt ctttggtcaa    4560
ggtaagtaaa tgcctatgat gtttggctgt gcacaagata aagctacaac aaagctacaa    4620
cccatctttt ctctgtagaa gactcaaaaa gcaaaagaga cccaggaaaa tctcggaatg    4680
acttttggaa cagagagcct ccccagaatc agaagtcaag gaatttaaac atagggaagg    4740
cccaggtctc tactgacata aaggaaagat gttttcttat aggtttcacg tttacatttt    4800
ctctctcttg atcccattcc cacttgcatc tgccacctttt acacagggct tatgggacct    4860
cctccacaaa agagcagttg cagtaaccca catcatcctc tacgccctgg ctgtccatca    4920
agaggcgaaa agcagcccta tataggttct atccttggat agttccagtt gtaaagttta    4980
aaatatgcga aggcaacttg gaaaagcaag cggctgcata caaagcaaac gtttacagag    5040
ctctggacaa aattgagcgc ctatgtgtac atggcaagtg ttttttagtgt ttgtgtgttt    5100 acctgcttgt ctgggtgatt tgcctttga gagtctggag agtagaagta ctggttaaag    5160
gaacttccag acaggaagaa ggcagagaag agggtagaaa tgactctgat tcttggggct    5220
gagggttcct agagcaaatg gcacaatgcc acgaggcccg atctatccct atgacgaat    5280 ctaaggtttc agcaagtatc tgctggcttg gtcatggctt gctcctcagt ttgtaggaga    5340
ctctcccact ctcccatctg cgcgctctta tcagtcctga aaagaacccc tggcagccag    5400
gagcaggtat tcctatcgtc cttttcctcc ctccctcgcc ccaccctgtt ggtttttag    5460 attgggcttt ggaccaaaat ttcctgagtg ctggcctcca ggaaatctgg agccctggcg    5520
cctaaacctt ggtttaggaa accaggagct attcaggaag caggggtcct ccagggctag    5580
```

```
agctagcctc tcctgccctc gcccacgctg cgccagcact tgtttctcca aagccactag    5640
gcaggcgtta gcgcgcggtg aggggagggg agaaaaggaa aggggagggg agggaaaagg    5700
aggtgggaag gcaaggaggc cggcccggtg ggggcgggac ccgactcgca aactgttgca    5760
tttgctctcc acctcccagc gcccctccg agatcccggg gagccagctt gctgggagag     5820
cgggacggtc cggagcaagc ccacaggcag aggaggcgac agagggaaaa agggccgagc    5880
tagccgctcc agtgctgtac aggagccgaa gggacgcacc acgccagccc cagcccggct    5940
ccagcgacag ccaacgcctc ttgcagcgcg cggcttcga agccgccgcc cggagctgcc     6000
ctttcctctt cggtgaagtt tttaaaagct gctaaagact cggaggaagc aaggaaagtg    6060
cctggtagga ctgacggctg cctttgtcct cctcctctcc accccgcctc ccccaccct    6120 gccttcccccc cctccccgt cttctctccc gcagctgcct cagtcggcta ctctcagcca    6180 accccccctca ccaccttct ccccaccgc cccccgccc ccgtcgccca cgctgccag      6240 cccgagtttg cagagaggta actccctttg gctgcgagcg ggcgagctag ctgcacattg    6300
caaagaaggc tcttaggagc caggcgactg gggagcggct tcagcactgc agccacgacc    6360
cgcctggtta ggctgcacgc ggagagaacc ctctgttttc ccccactctc tctccacctc    6420
ctcctgcctt ccccacccg agtgcggagc cagagatcaa aagatgaaaa ggcagtcagg    6480
tcttcagtag ccaaaaaaca aacaaacaa aacaaaaaa caagaaataa agaaaaaga      6540 taataactca gttcttattt gcacctactt cagtggacac tgaatttgga aggtggagga    6600
ttttgttttt ttcttttaag atctgggcat cttttgaatc tacccttcaa gtattaagag    6660
acagactgtg agcctagcag ggcagatctt gtccaccgtg tgtcttcttc tgcacgagac    6720
tttgaggctg tcagagcgct ttttgcgtgg ttgctcccgc aagtttcctt ctctggagct    6780
tcccgcaggt gggcagctag ctgcagcgac taccgcatca tcacagcctg ttgaactctt    6840
ctgagcaaga gaaggggagg cggggtaagg gaagtaggtg gaagattcag ccaagctcaa    6900
ggatg                                                                6905
```

<210> SEQ ID NO 36
<211> LENGTH: 43
<212> TYPE: DNA
<213> ORGANISM: Artificial Sequence
<220> FEATURE:
<223> OTHER INFORMATION: primer

<400> SEQUENCE: 36

```
cacgcgtggt acctctagaa ataattccc aatattgaat ccc                       43
```

<210> SEQ ID NO 37
<211> LENGTH: 30
<212> TYPE: DNA
<213> ORGANISM: Artificial Sequence
<220> FEATURE:
<223> OTHER INFORMATION: primer

<400> SEQUENCE: 37

```
agctggctcc ccgggatctc ggaggggcgc                                     30
```

<210> SEQ ID NO 38
<211> LENGTH: 42
<212> TYPE: DNA
<213> ORGANISM: Artificial Sequence
<220> FEATURE:
<223> OTHER INFORMATION: primer

```
<400> SEQUENCE: 38
cacgcgtggt accagacagt gacaggactt aaacggggaa at          42

<210> SEQ ID NO 39
<211> LENGTH: 16
<212> TYPE: DNA
<213> ORGANISM: Artificial Sequence
<220> FEATURE:
<223> OTHER INFORMATION: primer

<400> SEQUENCE: 39
agctggctcc ccggga                                       16

<210> SEQ ID NO 40
<211> LENGTH: 39
<212> TYPE: DNA
<213> ORGANISM: Artificial Sequence
<220> FEATURE:
<223> OTHER INFORMATION: primer

<400> SEQUENCE: 40
cacgcgtggt acctatacac attatgtctt ttaaatgac              39

<210> SEQ ID NO 41
<211> LENGTH: 30
<212> TYPE: DNA
<213> ORGANISM: Artificial Sequence
<220> FEATURE:
<223> OTHER INFORMATION: primer

<400> SEQUENCE: 41
agctggctcc ccgggatctc ggaggggcgc                        30

<210> SEQ ID NO 42
<211> LENGTH: 39
<212> TYPE: DNA
<213> ORGANISM: Artificial Sequence
<220> FEATURE:
<223> OTHER INFORMATION: primer

<400> SEQUENCE: 42
cacgcgtggt acctatacac attatgtctt ttaaatgac              39

<210> SEQ ID NO 43
<211> LENGTH: 30
<212> TYPE: DNA
<213> ORGANISM: Artificial Sequence
<220> FEATURE:
<223> OTHER INFORMATION: primer

<400> SEQUENCE: 43
ccgccatggt gagcttggct gaatcttcca                        30

<210> SEQ ID NO 44
<211> LENGTH: 30
<212> TYPE: DNA
<213> ORGANISM: Artificial Sequence
<220> FEATURE:
<223> OTHER INFORMATION: primer

<400> SEQUENCE: 44
ccgggtacct gccctcgccc acgctgcgcc                        30

<210> SEQ ID NO 45
<211> LENGTH: 30
```

<212> TYPE: DNA
<213> ORGANISM: Artificial Sequence
<220> FEATURE:
<223> OTHER INFORMATION: primer

<400> SEQUENCE: 45
agctggctcc ccgggatctc ggaggggcgc                               30

<210> SEQ ID NO 46
<211> LENGTH: 30
<212> TYPE: DNA
<213> ORGANISM: Artificial Sequence
<220> FEATURE:
<223> OTHER INFORMATION: primer

<400> SEQUENCE: 46
ccgggtacct gccctcgccc acgctgcgcc                               30

<210> SEQ ID NO 47
<211> LENGTH: 30
<212> TYPE: DNA
<213> ORGANISM: Artificial Sequence
<220> FEATURE:
<223> OTHER INFORMATION: primer

<400> SEQUENCE: 47
agctggctcc ccgggatctc ggaggggcgc                               30

<210> SEQ ID NO 48
<211> LENGTH: 54
<212> TYPE: DNA
<213> ORGANISM: Artificial Sequence
<220> FEATURE:
<223> OTHER INFORMATION: primer

<400> SEQUENCE: 48
cagaacattt ctctatcgat aggtaccgag caggtattcc tatcgtcctt ttcc    54

<210> SEQ ID NO 49
<211> LENGTH: 54
<212> TYPE: DNA
<213> ORGANISM: Artificial Sequence
<220> FEATURE:
<223> OTHER INFORMATION: primer

<400> SEQUENCE: 49
ggaaaaggac gataggaata cctgctcggt acctatcgat agagaaatgt tctg    54

<210> SEQ ID NO 50
<211> LENGTH: 54
<212> TYPE: DNA
<213> ORGANISM: Artificial Sequence
<220> FEATURE:
<223> OTHER INFORMATION: primer

<400> SEQUENCE: 50
cagaacattt ctctatcgat aggtaccaaa tctggagccc tggcgcctaa acct    54

<210> SEQ ID NO 51
<211> LENGTH: 54
<212> TYPE: DNA
<213> ORGANISM: Artificial Sequence
<220> FEATURE:
<223> OTHER INFORMATION: primer

<400> SEQUENCE: 51

```
aggtttaggc gccagggctc cagatttggt acctatcgat agagaaatgt tctg         54
```

<210> SEQ ID NO 52
<211> LENGTH: 51
<212> TYPE: DNA
<213> ORGANISM: Artificial Sequence
<220> FEATURE:
<223> OTHER INFORMATION: primer

<400> SEQUENCE: 52

```
cagaacattt ctctatcgat aggtaccggc gttagcgcgc ggtgagggga g            51
```

<210> SEQ ID NO 53
<211> LENGTH: 51
<212> TYPE: DNA
<213> ORGANISM: Artificial Sequence
<220> FEATURE:
<223> OTHER INFORMATION: primer

<400> SEQUENCE: 53

```
tctccctcac cgcgcgctaa cgccggtacc tatcgataga gaaatgttct g            51
```

<210> SEQ ID NO 54
<211> LENGTH: 57
<212> TYPE: DNA
<213> ORGANISM: Artificial Sequence
<220> FEATURE:
<223> OTHER INFORMATION: primer

<400> SEQUENCE: 54

```
cagaacattt ctctatcgat aggtaccggg aaaaggaggt gggaaggcaa ggaggcc      57
```

<210> SEQ ID NO 55
<211> LENGTH: 57
<212> TYPE: DNA
<213> ORGANISM: Artificial Sequence
<220> FEATURE:
<223> OTHER INFORMATION: primer

<400> SEQUENCE: 55

```
ggcctccttg ccttcccacc tccttttccc ggtacctatc gatagagaaa tgttctg      57
```

<210> SEQ ID NO 56
<211> LENGTH: 60
<212> TYPE: DNA
<213> ORGANISM: Artificial Sequence
<220> FEATURE:
<223> OTHER INFORMATION: primer

<400> SEQUENCE: 56

```
cagaacattt ctctatcgat aggtaccctc gcaaactgtt gcatttgctc tccacctccc   60
```

<210> SEQ ID NO 57
<211> LENGTH: 60
<212> TYPE: DNA
<213> ORGANISM: Artificial Sequence
<220> FEATURE:
<223> OTHER INFORMATION: primer

<400> SEQUENCE: 57

```
gggaggtgga gagcaaatgc aacagtttgc gagggtacct atcgatagag aaatgttctg   60
```

<210> SEQ ID NO 58
<211> LENGTH: 65
<212> TYPE: DNA
<213> ORGANISM: Artificial Sequence

```
<220> FEATURE:
<223> OTHER INFORMATION: primer

<400> SEQUENCE: 58
ccagtgctgt acaggagccg aagggacgca ccccatggaa gacgccaaaa acataaagaa    60
aggcc                                                                65

<210> SEQ ID NO 59
<211> LENGTH: 63
<212> TYPE: DNA
<213> ORGANISM: Artificial Sequence
<220> FEATURE:
<223> OTHER INFORMATION: primer

<400> SEQUENCE: 59
cctttcttta tgttttggc gtcttccatg gggtgcgtcc cttcggctcc tgtacagcac     60
tgg                                                                  63

<210> SEQ ID NO 60
<211> LENGTH: 59
<212> TYPE: DNA
<213> ORGANISM: Artificial Sequence
<220> FEATURE:
<223> OTHER INFORMATION: primer

<400> SEQUENCE: 60
ccacaggcag aggaggcgac agagggccat ggaagacgcc aaaaacataa agaaaggcc     59

<210> SEQ ID NO 61
<211> LENGTH: 57
<212> TYPE: DNA
<213> ORGANISM: Artificial Sequence
<220> FEATURE:
<223> OTHER INFORMATION: primer

<400> SEQUENCE: 61
cctttcttta tgttttggc gtcttccatg gccctctgtc gcctcctctg cctgtgg       57

<210> SEQ ID NO 62
<211> LENGTH: 63
<212> TYPE: DNA
<213> ORGANISM: Artificial Sequence
<220> FEATURE:
<223> OTHER INFORMATION: primer

<400> SEQUENCE: 62
gggagagcgg gacggtccgg agcaagccca ccatggaaga cgccaaaaac ataaagaaag    60
gcc                                                                  63

<210> SEQ ID NO 63
<211> LENGTH: 63
<212> TYPE: DNA
<213> ORGANISM: Artificial Sequence
<220> FEATURE:
<223> OTHER INFORMATION: primer

<400> SEQUENCE: 63
ggcctttctt tatgttttg gcgtcttcca tggtgggctt gctccggacc gtcccgctct    60
ccc                                                                  63

<210> SEQ ID NO 64
<211> LENGTH: 17
<212> TYPE: DNA
```

<210> SEQ ID NO 65
<211> LENGTH: 16
<212> TYPE: DNA
<213> ORGANISM: Homo sapiens

<400> SEQUENCE: 65
gctctccacc tcccag                                                  16

<210> SEQ ID NO 66
<211> LENGTH: 25
<212> TYPE: DNA
<213> ORGANISM: Homo sapiens

<400> SEQUENCE: 66
ggtgagggga ggggagaaaa ggaaa                                        25

<210> SEQ ID NO 67
<211> LENGTH: 2167
<212> TYPE: DNA
<213> ORGANISM: Homo sapiens

<400> SEQUENCE: 67
caggccccac aaaacctaga tctgccccag tataactaaa tctgggacca tttattgagc    60
aattattatg tgccaagtat tgcgctgagt gcttccagag cattatctcc tttaacccca   120
gcatagtatg tcagatgctg ttttacagat gagccaactg agaccagaga tgctcagtca   180
cttgcccaag gtgacatgac tgatatggaa tagagtcaag attttttttt ttttttttga   240
cacggagtct cactctgtct cccaggctgg agtgcagagg cgcaatctca gctcactgca   300
agctctgcct cccaggttca cgcattctcc tgcctcagcc tcctgagtag ctgggactac   360
aggcacccgc caccacacct ggctaatttt ttgtattttt agcagagaca gggtttcacc   420
gtgttagcca ggatggtctc gatctcctga cctcgtgatc tgcctgcctc ggcctcccaa   480
agtgatggaa ttacaggtgt gagccaccgc gactggccag attcaagatt tgaacccagg   540
tcctcttggt cccagaggcc cctgtttctc aactccctag catgcatacg cacctgtccc   600
tctagaggtg cctgcttaag tgtgctcagc acatggaagc aagttagaaa tgctaggtat   660
acctgtaaag aggtgtggga gatgggggggg agggaagaga gaaagagatg ctggtgtcct   720
tcattctcca gtccctgata ggtgcctttg atcccttctt gaccagtata gctgcattct   780
tggctggggc attccaacta gaactgccaa atttagcaca taaaaataag gaggcccagt   840
taaatttgaa tttcagataa acaatgaata atttgttagt ataaatatgt cccatgcaat   900
atcttgttga aattaaaaaa aaaaaaaaaa gtcttccttc catccccacc cctaccacta   960
ggcctaagga atagggtcag gggctccaaa tagaatgtgg ttgagaagtg gaattaagca  1020
ggctaataga aggcaagggg caaagaagaa accttgaatg cattgggtgc tgggtgcctc  1080
cttaaataag caagaagggt gcattttgaa gaattgagat agaagtcttt ttgggctggg  1140
tgcagttgct cgtggtttgta attccagcac tttgggaggc tgaggcggga ggatcacctg  1200
agcttgggag ttcaagacca gcctcaccaa cgtggagaaa ccctgtcttt actaaaaata  1260
caaaaaattc agctggtcat ggtggcacat gcctgtaatc ccagctgctc gggaggctga  1320
ggcaggagaa tcacttgaac cagggaggca gaggttgtgg tgagcagaga tcgcgccatt  1380

```
gctctccagc ctgggcaaca agagcaaaag ttcgtttaaa aaaaaaaaaa agtcctttcg    1440
atgtgactgt ctcctcccaa atttgtagac cctcttaaga tcatgctttt cagatacttc    1500
aaagattcca gaagatatgc cccggggtc ctggaagcca aaggtaaac acaacacatc       1560 cccctccttg actatcaatt ttactagagg atgtggtggg aaaaccatta tttgatatta    1620
aaacaatagg cttgggatgg agtaggatgc aagctcccca ggaagttaga taactgagac    1680
ttaaagggtg ttaagagtgg cagcctaggg aaatttatcc cggactccgg gggagggggc    1740
agagtcacca gcctctgcat ttagggattc tccgaggaaa agtgtgagaa cggctgcagg    1800
caacccaggc gtcccggcgc taggagggac gacccaggcc tgcgcgaaga gagggagaaa    1860
gtgaagctgg gagttgccga ctcccagact tcgttggaat gcagttggag ggggcgagct    1920
gggagcgcgc ttgctcccaa tcaccggaga aggaggaggt ggaggaggag ggctgcttga    1980
ggaagtataa gaatgaagtt gtgaagctga gattcccctc cattgggacc ggagaaacca    2040
ggggagcccc ccgggcagcc gcgcgcccct tcccacgggg cccttactg cgccgcgcgc     2100 ccggccccca ccctcgcag caccccgcgc cccgcgccct cccagccggg tccagccgga     2160
gccatgg                                                              2167

<210> SEQ ID NO 68
<211> LENGTH: 32
<212> TYPE: DNA
<213> ORGANISM: Artificial Sequence
<220> FEATURE:
<223> OTHER INFORMATION: primer

<400> SEQUENCE: 68
gcacgcgtaa gcttcaggcc ccacaaaacc ta                                    32

<210> SEQ ID NO 69
<211> LENGTH: 35
<212> TYPE: DNA
<213> ORGANISM: Artificial Sequence
<220> FEATURE:
<223> OTHER INFORMATION: primer

<400> SEQUENCE: 69
cgctcgagcc atggctccgg ctggacccgg ctggg                                 35

<210> SEQ ID NO 70
<211> LENGTH: 10
<212> TYPE: DNA
<213> ORGANISM: Homo sapiens

<400> SEQUENCE: 70
gaatgaagtt                                                             10

<210> SEQ ID NO 71
<211> LENGTH: 15
<212> TYPE: DNA
<213> ORGANISM: Homo sapiens

<400> SEQUENCE: 71
cgcttgctcc caatc                                                       15

<210> SEQ ID NO 72
<211> LENGTH: 13
<212> TYPE: DNA
<213> ORGANISM: Homo sapiens
```

```
<400> SEQUENCE: 72
gaggaaggta taa                                                        13

<210> SEQ ID NO 73
<211> LENGTH: 135
<212> TYPE: DNA
<213> ORGANISM: Escherichia coli

<400> SEQUENCE: 73
gacgtcaggt ggcacttttc ggggaaatgt gcgcggaacc cctatttgtt tatttttcta    60
atacattcaa atatgtatcc gctcatgaga caataaccct gataaatgct tcaataatat   120
tgaaaaagga agagt                                                    135

<210> SEQ ID NO 74
<211> LENGTH: 136
<212> TYPE: DNA
<213> ORGANISM: Escherichia coli

<400> SEQUENCE: 74
gacgtcaggt ggcacttttc ggggaaatgt gcgcggaacc cctatctgtt tgttcttcta    60
gacacattca cacatgtatc cgctcatgag acaataaccc tgataaatgc ttcaatgaca   120
ttgagaaagg aagagt                                                   136

<210> SEQ ID NO 75
<211> LENGTH: 12
<212> TYPE: DNA
<213> ORGANISM: Escherichia coli

<400> SEQUENCE: 75
aatacattca aa                                                         12

<210> SEQ ID NO 76
<211> LENGTH: 12
<212> TYPE: DNA
<213> ORGANISM: Escherichia coli

<400> SEQUENCE: 76
catgagacaa ta                                                         12

<210> SEQ ID NO 77
<211> LENGTH: 12
<212> TYPE: DNA
<213> ORGANISM: Escherichia coli

<400> SEQUENCE: 77
accctgataa at                                                         12

<210> SEQ ID NO 78
<211> LENGTH: 12
<212> TYPE: DNA
<213> ORGANISM: Escherichia coli

<400> SEQUENCE: 78
ttgaaaaagg aa                                                         12
```